US008658783B2

(12) United States Patent
Bhanot et al.

(10) Patent No.: US 8,658,783 B2
(45) Date of Patent: Feb. 25, 2014

(54) ANTISENSE MODULATION OF PTP1B EXPRESSION

(75) Inventors: Sanjay Bhanot, Carlsbad, CA (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/446,763

(22) Filed: Apr. 13, 2012

(65) Prior Publication Data

US 2012/0289580 A1 Nov. 15, 2012

Related U.S. Application Data

(60) Provisional application No. 61/474,981, filed on Apr. 13, 2011.

(51) Int. Cl.
*C07H 21/04* (2006.01)
*C07H 21/02* (2006.01)
*A61K 48/00* (2006.01)

(52) U.S. Cl.
USPC ..... 536/24.5; 536/23.1; 536/24.3; 536/24.31; 536/24.33; 514/44

(58) Field of Classification Search
None
See application file for complete search history.

(56) References Cited

U.S. PATENT DOCUMENTS

| | | | |
|---|---|---|---|
| 5,726,027 A | 3/1998 | Olefsky | |
| 5,801,154 A | 9/1998 | Baracchini et al. | |
| 6,261,840 B1 | 7/2001 | Cowsert et al. | |
| 6,261,849 B1 | 7/2001 | Lee | |
| 6,506,559 B1 | 1/2003 | Fire et al. | |
| 6,582,908 B2 | 6/2003 | Fodor et al. | |
| 6,602,857 B1 | 8/2003 | Cowsert et al. | |
| 7,179,796 B2 | 2/2007 | Cowsert et al. | |
| 7,427,672 B2 | 9/2008 | Imanishi et al. | |
| 7,563,884 B2 | 7/2009 | Cowsert et al. | |
| 7,687,616 B1 | 3/2010 | Bentwich et al. | |
| 7,834,170 B2 | 11/2010 | Khvorova et al. | |
| 8,017,760 B2 | 9/2011 | Bhanot et al. | |
| 8,039,608 B1 | 10/2011 | Bentwich | |
| 2001/0053519 A1 | 12/2001 | Fodor et al. | |
| 2002/0055479 A1* | 5/2002 | Cowsert et al. ............... | 514/44 |
| 2002/0198203 A1 | 12/2002 | Vitou et al. | |
| 2003/0108883 A1 | 6/2003 | Rondinone et al. | |
| 2003/0220282 A1 | 11/2003 | Cowsert et al. | |
| 2003/0228597 A1 | 12/2003 | Cowsert et al. | |
| 2004/0005618 A1 | 1/2004 | Yu et al. | |
| 2004/0009946 A1 | 1/2004 | Lewis et al. | |
| 2004/0019001 A1 | 1/2004 | McSwiggen | |
| 2005/0070497 A1 | 3/2005 | McSwiggen et al. | |
| 2005/0095710 A1 | 5/2005 | Cowsert et al. | |
| 2006/0025372 A1 | 2/2006 | Bhanot et al. | |
| 2006/0089325 A1 | 4/2006 | Bhanot et al. | |
| 2007/0031844 A1 | 2/2007 | Khvorova et al. | |
| 2008/0015162 A1 | 1/2008 | Bhanot et al. | |
| 2008/0097092 A1 | 4/2008 | Khvorova et al. | |
| 2009/0036355 A1 | 2/2009 | Bhanot et al. | |
| 2009/0124009 A1 | 5/2009 | Bhanot et al. | |
| 2009/0318532 A1 | 12/2009 | Bhanot et al. | |
| 2009/0318536 A1 | 12/2009 | Freier et al. | |
| 2010/0105134 A1 | 4/2010 | Quay et al. | |
| 2010/0197773 A1 | 8/2010 | Bramlage et al. | |
| 2012/0077862 A1 | 3/2012 | Bhanot et al. | |

FOREIGN PATENT DOCUMENTS

| | | |
|---|---|---|
| WO | WO 97/32595 | 9/1997 |
| WO | WO 98/20024 | 5/1998 |
| WO | WO 01/05954 | 1/2001 |
| WO | WO 01/07655 | 1/2001 |
| WO | WO 01/16312 | 3/2001 |
| WO | WO 01/30801 | 5/2001 |
| WO | WO 01/53528 | 7/2001 |
| WO | WO 02/59137 | 1/2002 |
| WO | WO 02/10378 | 2/2002 |
| WO | WO 02/44321 | 6/2002 |
| WO | WO 02/064840 | 8/2002 |
| WO | WO 02/092772 | 11/2002 |
| WO | WO 03/007951 | 1/2003 |
| WO | WO 03/070881 | 8/2003 |
| WO | WO 03/099227 | 12/2003 |
| WO | WO 2004/016735 | 2/2004 |
| WO | WO 2004/046161 | 6/2004 |
| WO | WO 2004/071407 | 8/2004 |
| WO | WO 2005/021572 | 3/2005 |
| WO | WO 2006/044531 | 4/2006 |
| WO | WO 2007/131237 | 11/2007 |
| WO | WO 2007/146511 | 12/2007 |
| WO | WO 2008/109470 | 9/2008 |

OTHER PUBLICATIONS

International Search Report for PCT/US12/33588 dated Aug. 31, 2012.

Brand et al., "Dual PPAR alpha/gamma activation provides enhanced improvement of insulin sensitivity and glycemic control in ZDF rats" American Journal of Physiology—Endocrinology and Metabolism (2003) 284:E841-854.

Abrahamson, "Clinical use of thiazolidinediones: Recommendations" The American Journal of Medicine (2003) 115:116S-120S.

Adjei et al., "A Phase I trial of ISIS 2503, an antisense inhibitor of H-ras, in combination with gemcitabine in patients with advanced cancer" Clinical Cancer Research (2003) 9:115-123.

Agrawal et al., "Antisense Therapeutics: Is It as Simple as Complementary Base Recognition?" Molecular Medicine Today (2000) 6(2):72-81.

Ahmad et al., "Improved Sensitivity to Insulin in Obese Subjects Following Weight Loss is Accompanied by Reduced Protein-Tyrosine Phosphatases in Adipose Tissue" *Metabolism* (1997) 46:1140-1145.

(Continued)

*Primary Examiner* — Amy Bowman

(74) *Attorney, Agent, or Firm* — Isis Pharmaceuticals, Inc. Patent Dept.

(57) ABSTRACT

Provided herein are methods, compounds, and compositions for reducing expression of PTP1B mRNA and protein in an animal. Such methods, compounds, and compositions are useful to treat, prevent, delay, or ameliorate metabolic disease, for example, diabetes, or a symptom thereof.

17 Claims, 3 Drawing Sheets

(56) References Cited

OTHER PUBLICATIONS

Arregui et al., "Impaired integrin-mediated adhesion and signaling in fibroblasts expressing a dominant-negative mutant PTP1B" *J. Cell. Biol.* (1998) 143:861-873.
Asante-Appiah et al., "Protein tyrosine phosphatase: the quest for negative regulators of insulin action" *Am. J. Physiol. Endocrinol. Metab.* (2003) 284:E663-E670.
Balsamo et al., "The nonreceptor protein tyrosine phosphatase PTP1B binds to the cytoplasmic domain of N-cadherin and regulates the cadherin-actin linkage" *J. Cell. Biol.* (1998) 143:523-532.
Bhanot et al., "A Novel PTP-1B Antisense Inhibitor (ISIS 113715) Improves Insulin Sensitivity in Obese Hyperinsulinemic Rhesus Monkeys" *ADA Annual Meeting* (2003) Abstract 477-P.
Branch et al., "A good antisense molecule is hard to fin" *TIBS* (1998) 23:45-50.
Brown-Shimer et al., "Effect of protein tyrosine phosphatase 1B expression on transformation by the human neu oncogene" *Cancer Res.* (1992) 52:478-482.
Cheetham et al., "Novel targets for the treatment of obesity: a review of progress" *Drug Discovery Today: Therapeutic Strategies* (2004) 1:227-235.
Chen et al., "A phosphotyrosyl mimetic peptide reverses impairment of insulin-stimulated transolcation of GLUT4 caused by overexpression of PTP1B in rat adipose cells" *Biochemistry* (1999) 38:384-389.
Chen et al., "Protein-tyrosine phosphatases PTP1B and syp are modulators of insulin-stimulated translocation of GLUT4 in transfected rat adipose cells" *J. Biol. Chem.* (1997) 272:8026-8031.
Chernoff et al., "Cloning of a cDNA for a Major Human Protein-Tyrosine-Phosphatase" *Proc. Natl. Acad. Sci. USA* (1990) 87:2735-2739.
Chin, "On the preparation and Utilization of Isolated and Purified Oligonucleotides" Document purportedly located on a CD-ROM and contributed to the public collection of the Katherine R. Everett Law Library of the University of North Carolina on Mar. 14, 2002.
Clampit et al., "Reduction of protein-tyrosine phosphatase-1B increases insulin signaling in FAO hepatoma cells" *Biochem. Biophys. Res. Commun.* (2003) 300:261-267.
Cox et al., "Absorption, disposition, and metabolism of rosigitazone, a potent thiazolidinedione insulin sensitizer, in humans" Drug Metabolism and Disposition (2000) 28:772-780.
Crooke et al., "Basic Principles of Antisense Therapeutics" Antisense Research and Application (1998) Chapter 1:1-50.
Crooke, "Antisense therapeutics" Biotechnology & Genetic Engineering Reviews (1998) 15:121-157.
Crystal et al., "Transfer of genes to humans: early lessons and obstacles to success" Science (1995) 270:404-410.
Day, "Thiazolidinediones: a new class of antidiabetic drugs" Diabetic Medicine (1999) 16:179-192.
Desmarais et al., "Inhibition of protein tyrosine phosphatases PTP1B and CD45 by sulfotyrosyl peptides" *Arch. Biochem. Biophys.* (1998) 354:225-231.
Elchebly et al., "Increased insulin sensitivity and obesity resistance in mice lacking the protein tyrosine phosphatase-1B gene" *Science* (1999) 283:1544-1548.
Ferber, "New Clues Found to Diabetes and Obesity" Science (1999) 283:1423-1424.
Friedmann et al., "Overcoming the Obstacles to gene therapy" Scientific American (1997) 276:96-101.
Geary et al., "Pharmacokinetics of a tumor necrosis factor-alpha phosphorothiaote 2'-O-(2'-methoxyethyl) modified antisense oligonucleotide: comparison across species" Drug Metabolism and Disposition (2003) 31:1419-1428.
Goldstein et al., "Regulation of the insulin signalling pathway by ceullular protein-tyrosine phosphatases" *Mol. Cell. Biochem.* (1998) 182:91-99.
Goldstein et al., "Protein-Tyrosine Phosphatase 1B (PTP1B): A Novel Therapeutic Target for Type 2 Diabetes Mellitus, Obesity and Related States of Insulin Resistance" *Curr. Drug Targets—Immun. Endocrin. Metab. Disorders* (2001) 1:265-275.

Goldstein, "Protein-tyrosine phosphatases: Emerging targets for therapeutic intervention in type 2 diabetes and related states of insulin resistance" The Journal of Clinical Endocrinology & Metabolism (2002) 87:2474-2480.
Goldstein et al., "Tests of Glycemia in Diabetes" *Diabetes Care* (2004) 27:1761-1773.
Graham et al., "In Vivo Distribution and Metabolism of a Phosphorothioate Oligonucleotides Within Rat Liver after Intravenous Administration" J. Pharm. Exp. Ther. (1998) 286:447-458.
Guan et al., "Cloning and Expression of Protein-Tyrosine-Phosphatase" Proc. Natl. Acad. Sci. USA (1990) 87:1501-1505.
Gum et al., "Antisense Protein Tyrosine Phosphatase 1B Reverses Activation of p38 Mitogen-Activated Protein Kinase in Liver of ob/ob Mice" *Molecular Endocrin.* (2003) 17:1131-1143.
Gum et al., "Reduction of Protein Tyrosine Phosphatase 1B Increases Insulin-Dependent Signaling in ob/ob Mice" *Diabetes* (2003) 52:21-28.
Ham et al., "Selective inactivation of protein tyrosine phosphatase PTP1B by sulfone analogue of naphthoquinone" *Bioorg. Med. Chem. Lett.* (1999) 9:185-186.
Hassid et al., "Antisense oligonucleotides against protein tyrosine phosphatase 1B increase focal adhesion protein phosphorylation and migration in rat aortic smooth muscle cells" in Supplement to Circulation, Journal of the American Heart Association, Abstracts from 71st Scientific Sessions (1998) Abstract No. 1733.
Hassid et al., "No Alters Cell Shape and Motility in Aortic Smooth Muscle Cells via Protein Tyrosine Phosphatase 1B Activation" Am. J. Phys. (1999) 277:H1014-1026.
Hassid et al., "Role of PTP1B in Aortic Smooth Muscle Cell Motility and Tyrosine Phosphorylation of Focal Adhesion Proteins" Am. J. Phys. (1999) 277:H192-198.
Henry et al., "Toxicology and Pharmacokinetic Properties of Chemically Modified Antisense Oligonucleotide Inhibitors of PKC-Alpha and C-Raf Kinase" Anti-Cancer Drug Design (1997) 12:409-420.
Ho et al., "Mapping or RNA Accessible Sites for Antisense Experiments with Oligonucleotide Libraries" Nature Biotech. (1998) 16:59-63.
Hormes et al., "The subcellular localization and length of hammerhead ribozymes determine efficacy in human cells" Nucleic Acids Res. (1997) 25:769-775.
Huang et al., "Antisense to protein tyrosine phosphatase 1B increases Tyrosine Phosphorylation of Focal Adhesion Protein in Aortic Smooth Muscle Cells of Rats" FASEB (1998) 12:A188, Abstract No. 1099.
James et al., "Towards Gene-Inhibition Therapy: A Review of Progress and Prospects in the Field of Antiviral Antisense Nucleic Acids and Ribozymes" Antiviral Chem. and Chemotherapy (1991) 2:191-214.
Kjems et al., "Increased Insulin Sensitivity in Humans by Protein Tyrosine Phosphatase 1B (PTP-1B) Inhibition-Evaluation of ISIS 113715, an Antisense Inhibitor of PTP-1B" *San Diego ADA Annual Meeting* (2005) Abstract 2201-PO.
Ko et al., "The effect of rosiglitazone on serum lipoprotein(a) levels in Korean patients with type 2 diabetes mellitus" Metabolism (2003) 52:731-734.
Lamontagne et al., "Protein tyrosine phosphatase PTP1B suppresses p210 bcr-abl-induced transformation of rat-1 fibroblasts and promotes differentiation of K562 cells" *Proc. Natl. Acad. Sci. USA* (1998) 95:14094-14099.
Lee et al., "Reversible inactivation of protein-tyrosine phosphatase 1B in A431 cells stimulated with epidermal growth factor" *J. Biol. Chem.* (1998) 273:15366-15372.
Liu et al., "Protein tyrosine phosphatase 1B interacts with and is tyrosine phosphorylated by the epidermal growth factor receptor" Biochem. J. (1997) 327:139-145.
Liu et al., "Protein tyrosine phosphatase 1B negatively regulates integrin signaling" *Curr. Biol.* (1998) 8:173-176.
Liu et al., "Transformation suppression by protein tyrosine phosphatase 1B requires a functional SH3 ligand" *Mol. Cell. Biol.* (1998) 18:250-259.
Liu et al., "Protein tyrosine phosphatase 1B as a target for the treatment of impaired glucose tolerance and Type II diabetes" *Curr. Opin. Invest. Drugs* (2002) 3:1608-1616.

(56) References Cited

OTHER PUBLICATIONS

Liu, "Technology evaluation: ISIS-113715, Isis," *Curr. Opin. Mol. Therap.* (2004) 6:331-336.

Madsbad et al., "Improved glycemic control with no weight increase in patients with type 2 diabetes after once-daily treatment with the long-acting glucagan-like peptide 1 analog liraglutide (NN2211): a week, double-blind, randomized, controlled trial" Diabetes Care (2004) 27:1335-1342.

Mani et al., "Phase I clinical and pharmacokinetic study of protein kinase C—a antisense oligonucleotide ISIS 3521 administered in combination with 5-fluorouracil and leucovorin in patients with advanced cancer" Clinical Cancer Research (2002) 8:1042-1048.

Mauvais-Jarvis et al., "Therapeutic perspectives for type 2 diabetes mellitus: Molecular and clinical insights" Diabetes & Metabolism (2001) 27:415-423.

McKay et al., "Effects of a Novel PTP-1B Antisense Oligonucleotide Inhibitor (ISIS 113715) on PTP-1B Expression in Different Liver Cell Types" *ADA Annual Meeting* (2003) Abstract 611-P.

Meriden, "Progress with thiazolidinediones in the management of type 2 diabetes mellitus" Clinical Therapeutics (2004) 26:177-190.

Milner et al., "Selecting effective antisense reagents on combinatorial oligonucleotide arrays" *Nature* (1997) 15:537-541.

Moller et al., "Protein tyrosine phosphatases (PTPs) as drug targets: Inhibitors of PTP1B for the treatment of diabetes" *Curr. Opin. Drug Discov. Dev.* (2000) 3:527-540.

Monia, "Protein Phosphatases" *FASEB Summer Conference presentation on Protein Phosphatases in Colorado*, Jul. 23-28, 2000, poster presentation, 14 pages.

Monia, "Protein Phosphatases" *FASEB Summer Conference presentation on Protein Phosphatases in Colorado*, Jul. 23-28, 2000, oral presentation, 20 pages.

Murray et al., "Additive Glucose Lowering Effects of a Novel PTP-1B Antisense Oligonucleotide (ISIS 113715) with Rosiglitazone and Metformin in ZDF Rats" *San Diego ADA Annual Meeting* (2005) Abstract 1545-P.

New England Biolabs 1998/1999 Catalog, cover page, pp. 121 and 284.

Nuss et al., "Effects of Protein Tyrosine Phosphatase 1B (PTP1B) Antisense Oligonucleotide (ASO) Treatment on Fat Volume Using MRI in Zucker Fatty Rats" Diabetes (2001) 50:A377.

Palu et al., "In Pursuit of new developments for gene therapy of human disease" J. Biotech. (1999) 68:1-13.

Parker, "Preclinical studies and clinical trials for diabetes—second annual forum: Identify emerging therapies and improve trial efficacy" Idrugs (2004) 7:37-39.

Peracchi et al., "Prospects for antiviral ribozymes and deoxyribozymes" Rev. in Med. (2004) 14:47-64.

Pihl-Carey, "Isis to Restructure as Crohn's Disease Drug Fails in Phase III" BioWorld Today (The Daily Biotechnology Newspaper) (1999) 10:1-2.

Reynolds et al., "Rational siRNA design for RNA interference" Nature Biotechnology (2004) 22(3):326-330.

Roller et al., "Potent inhibition of protein-tyrosine phosphatase-1B using the phosphotyrosyl mimetic fluoro-O-malonyl tyrosine (FOMT)" Bioorg. Med. Chem. Lett. (1998) 8:2149-2150.

Rondinone et al., "Inhibition of PTP1B Induces Differential Expression of PI3-Kinase Regulatory Subunit (p85alpha) Isoforms" Diabetes (2001) 50:A400.

Rondinone et al., "Protein Tyrosine Phosphatase 1B Reduction Regulates Adiposity and Expression of Genes Involved in Lipogenesis" Diabetes (2002) 51:2405-2411.

Sanghvi et al., "Heterocyclic Base Modifications in Nucleic Acids and Their Applications in Antisense Oligonucleotides" Antisense Research and Applications (1993) pp. 273-288.

Schievella et al., "Protein tyrosine phosphatase 1B undergoes mitosis-specific phosphorylation on serine" *Cell. Growth Differ.* (1993) 4:239-246.

Schofield et al., "Non-viral approaches to gene therapy" Brit. Med. Bull. (1995) 51:56-71.

Seely et al., "Protein tyrosine phosphatase 1B interacts with the activated insuliun receptor" *Diabetes* (1996) 45:1379-1385.

Sell et al., "Insulin-inducible changes in the relative ratio of PTP1B splice variants" *Mol. Genet. Metab.* (1999) 66:189-192.

Shifrin et al., "Growth factor-inducible alternative splicing of nontransmembrane phosphotyrosine phosphatase PTP1B pre-mRNA" *J. Biol. Chem.* (1993) 268:25376-25384.

Skorey et al., "How does alendronate inhibit protein-tyrosine phosphatases?" *J. Biol. Chem.* (1997) 272:22472-22480.

Skrumsager et al., "Ragaglitazar: the parmacokinetics, pharmacodynamics, and tolerability of a novel dual PPARalpha and gamma agonist in healthy subjects and patients with type 2 diabetes" Journal of Clinical Pharmacology (2003) 43:1244-1256.

Standl et al., "Effect of acarbose on additional insulin therapy in type 2 diabetic patients with late failure of sulphonylurea therapy" *Diabetes, Obesity and Metabolism* (1999) 1:215-220.

Stein et al., "Antisense oligonucleotides as therapeutic agents—is the bullet really magical?" Science (1993) 261:1004-1012.

Stull et al., "An In Vitro Messenger RNA Binding Assay as a Tool for Identifying Hybridization-Competent Antisense Oligonucleotides" Antisense & Nucleic Acid Drug Development (1996) 6:221-228.

Strickland et al., "Antisense RNA Directed Against the 3' Noncoding Region Prevents Dormant mRNA Activation in Mouse Oocytes" Science (1988) 241:680-684.

Taing et al., "Potent and highly selective inhibitors of the protein tyrosine phosphatase 1B" *Biochemistry* (1999) 38:3793-3803.

Taylor et al., "Potent non-peptidyl inhibitors of protein tyrosine phosphatase 1B [published erratum appears in Bioorg Med Chem Nov. 1998;6(11):2235]" *Bioorg. Med. Chem.* (1998) 6:1457-1468.

Tonks et al., "Characterization of the major protein-tyrosine-phosphatases of human placenta" *J. Biol. Chem.* (1998) 263:6731-6737.

Tonks et al., "Purification of the major protein-tyrosine-phosphatases of human placenta" *J. Biol. Chem.* (1998) 263: 6722-6730.

Verma et al., "Gene Therapy: promises, problems and prospects" Nature (1997) 389:239-242.

Vickers et al., "Efficient reduction of target RNAs by small interfering RNA and Rnase H-dependent antisense agents" *The Journal of Biological Chemistry* (2003) 278:7108-7118.

Wagner, "Early clinical development of pharmaceuticals for type 2 diabetes mellitus: From preclinical models to human investigation" The Journal of Clinical Endocrinology & Metabolism (2002) 87:5362-5366.

Walczak, "Diabetes Technology News" Diabetes Technology & Therapeutics (2001) 3:307-331.

Wang et al., "Naphthalenebis [alpha, alpha-difluoromethylenephosphonates] as potent inhibitors of protein tyrosine phosphatases" *Bioorg. Med. Chem. Lett.* (1998) 8:345-350.

Wang et al., "Mechanism of inhibition of protein-tyrosine phosphatases by disodium aurothiomalate" *Biochem. Pharmacol.* (1997) 54:703-711.

Waring et al., "PTP1B antisense-treated mice show regulation of genes involved in lipogenesis in liver and fat" Mol. Cell. Endocrin. (2003) 203:155-168.

Wiener et al., "Overexpression of the Protein Tyrosine Phosphatase PTP1B in Human Breast Cancer: Association with p185 Protein Expression" *J. Nat. Cancer Inst.* (1994) 86:372-378.

Wiener et al., "Overexpression of the tyrosine phosphatase PTP1B is associated with human ovarian carcinomas" *Am. J. Obstet. Gynecol.* (1994) 170:1177-1183.

Wu et al., "Rosiglitazone ameliorates abnormal expression and activity of protein tyrosine phosphatase 1B in the skeletal muscle of fat-fed, streptozotocin-treated diabetic rats" Br. J. Pharm. (2005) 146:234-243.

Yao et al., "Structure-based design and synthesis of small molecule protein-tyrosine phsphatase 1B inhibitors" *Bioorg. Med. Chem.* (1998) 6:1799-1810.

Yu et al., "Abstract of International Patent Publication No. WO-02/59137" published Aug. 1, 2002.

(56) References Cited

OTHER PUBLICATIONS

Zhang et al., "Protein-tyrosine phosphatases: biological function, structural characteristics, and mechanism of catalysis" *Crit. Rev. Biochem. Mol. Biol.* (1998) 33:1-52.

Zinker et al., "PTP1B antisense oligonucleotide lowers PTP1B protein, normalizes blood glucose, and improves insulin sensitivity in diabetic mice" *PNAS* (2002) 99:11357-11362.

Koizumi et al., "In vivo antisense activity of ENA oligonucleotides targeting PTP1B mRNA in comparison of that of 2'-MOE-modified oligonucleotides." Nucleic Acids Symp. Ser. (2007) 51:111-112.

Van Huijsduijnen et al., "Selecting protein tyrosine phosphatases as drug targets" DDT (2002) 7(19): 1013-1019.

Waring et al., "PTP1B antisense-treated mice show regulation of genes involved in lipogenesis in liver and fat" Molecular and Cellular Endocrinology (2003) 203:155-168.

\* cited by examiner

Comparison of Key Tolerability Parameters for 409826, 404173 and 142082

| 40 mpk/week | | | Fold over Saline | | |
|---|---|---|---|---|---|
| ISIS # | Chemistry | Walk Position | Spleen Wt | Kidney Wt | Liver Wt |
| 409826 | 5-10-5 | 4518 | 2.5 | 1.4 | 1.7 |
| 142082 | 5-10-5 | 4522 | 3.0 | 2.1 | 1.7 |
| 404173 | 5-10-5 | 4521 | 1.6 | 1.5 | 1.5 |

| 40 mpk/week | Fold Change vs Baseline | | | |
|---|---|---|---|---|
| ISIS # | C3 | CRP | MCP1 | IL-1 |
| Saline | -0.05 | 0.23 | -0.29 | -0.44 |
| 409826 | -0.30 | 3.90 | 2.31 | 2.37 |
| 142082 | -0.16 | 14.52 | 5.36 | 1.64 |
| 404173 | -0.18 | -0.48 | 0.82 | 0.09 |

Figure 2

* 1 animal very high at day 93; otherwise fold-increase was ~3-4 fold

ANTISENSE MODULATION OF PTP1B EXPRESSION

CROSS-REFERENCE TO RELATED APPLICATIONS

This application claims priority under 35 U.S.C. §119(e) to U.S. Provisional Application No. 61/474,981, filed Apr. 13, 2011, which is herein incorporated by reference in its entirety.

SEQUENCE LISTING

The present application is being filed along with a Sequence Listing in electronic format. The Sequence Listing is provided as a file entitled BIOL0149USSEQ.txt created Apr. 12, 2012, which is 111 Kb in size. The information in the electronic format of the sequence listing is incorporated herein by reference in its entirety.

FIELD

Provided herein are methods, compounds, and compositions for reducing expression of PTP1B mRNA and protein in an animal. Such methods, compounds, and compositions are useful, for example, to treat, prevent, delay or ameliorate diseases associated with metabolic disorders, particularly disorders associated with diabetes.

BACKGROUND

Protein tyrosine phosphatase 1B (PTP1B) is a member of a family of PTPs (Barford, et al., Science 1994. 263: 1397-1404) and is a cytosolic enzyme (Neel and Tonks, Curr. Opin. Cell Biol. 1997. 9: 193-204). PTP1B is expressed ubiquitously including tissues that are key regulators of insulin metabolism such as liver, muscle and fat (Goldstein, Receptor 1993. 3: 1-15), where it is the main PTP enzyme.

PTP1B is considered to be a negative regulator of insulin signaling. PTP1B interacts with and dephosphorylates the insulin receptor, thus attenuating and potentially terminating the insulin signaling transduction (Goldstein et al., J. Biol. Chem. 2000. 275: 4383-4389). The physiological role of PTP1B in insulin signaling has been demonstrated in knock-out mice models. Mice lacking the PTP1B gene were protected against insulin resistance and obesity (Elchebly et al., Science 1999. 283: 1544-1548). PTP1B-deficient mice had low adiposity, increased basal metabolic rate as well as total energy expenditure and were protected from diet-induced obesity. Insulin-stimulated glucose uptake was elevated in skeletal muscle, whereas adipose tissue was unaffected providing evidence that increased insulin sensitivity in PTP1B-deficient mice was tissue-specific (Klaman et al., Mol. Cell. Biol. 2000. 20: 5479-5489). These mice were phenotypically normal and were also resistant to diet-induced obesity, insulin resistance and had significantly lower triglyceride levels on a high-fat diet. Therefore, inhibition of PTP1B in patients suffering from Type II diabetes, metabolic syndrome, diabetic dyslipidemia, or related metabolic diseases would be beneficial.

Antisense inhibition of PTP1B provides a unique advantage over traditional small molecule inhibitors in that antisense inhibitors do not rely on competitive binding of the compound to the protein and inhibit activity directly by reducing the expression of PTP1B. Antisense technology is emerging as an effective means for reducing the expression of certain gene products and may therefore prove to be uniquely useful in a number of therapeutic, diagnostic, and research applications for the modulation of PTP1B.

There is a currently a lack of acceptable options for treating metabolic disorders. It is therefore an object herein to provide compounds and methods for the treatment of such diseases and disorder.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY

Provided herein are methods, compounds, and compositions for modulating expression of PTP1B and treating, preventing, delaying or ameliorating diseases associated with metabolic disorders, particularly disorders associated with diabetes and/or a symptom thereof.

BRIEF DESCRIPTION OF THE FIGURES

The numerous objects and advantages of the present invention can be better understood by those skilled in the art by reference to the accompanying figures, in which:

FIG. 2 is a summary table of key tolerability studies in cynomolgus monkeys (see Example 17).

DETAILED DESCRIPTION

Figure 1:
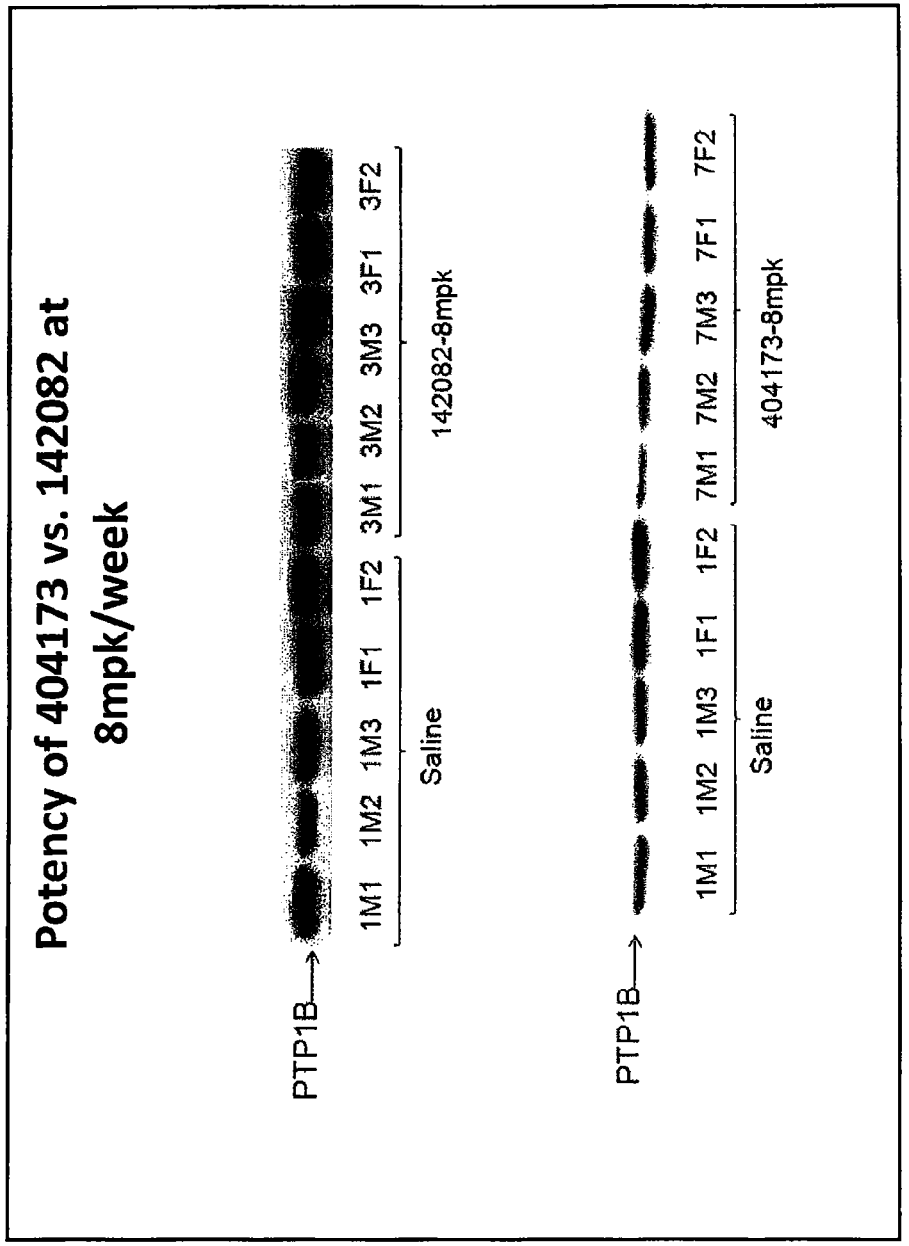
FIG. 1 shows a western blot of PTP1B antisense oligonucleotides, ISIS 404173 and ISIS 142082, decreasing PTP1B protein expression at 8 mgk/week demonstrating potency of the compounds. See Table 47.
Figure 3:
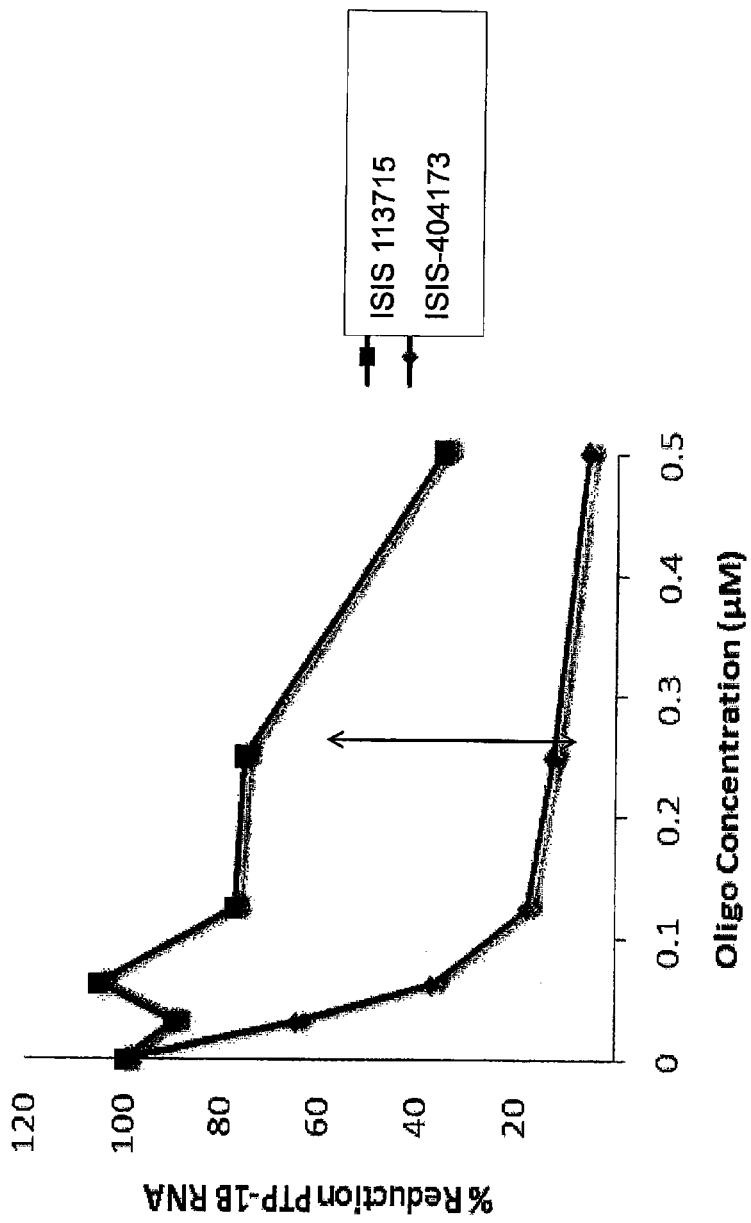
FIG. 3 is a graphical representation reduction of human PTP1B mRNA in a dose response preclinical study. Treatment with ISIS 404173 was compared with that of ISIS 113715, the previous clinical candidate. As shown here, dosing with ISIS 404173 was more potent and caused significant reduction in PTP1B mRNA levels compared to dosing with ISIS 113715. Particularly, at 0.3 µM dose, there was a fivefold decrease in PTP1B mRNA levels with ISIS 404173 compared to ISIS 113715.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all documents, or portions of documents, cited in this application, including, but not limited to, all patents, applications, published applications and other journal publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to PTP1B is an active pharmaceutical agent.

"Active target region" or "target region" means a region to which one or more active antisense compounds is targeted. "Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound provided herein. For example, a first agent can be an antisense oligonucleotide targeting PTP1B. "Second agent" means a second therapeutic compound of the invention (e.g. a second antisense oligonucleotide targeting PTP1B) and/or a non-PTP1B therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-1-IDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"MTP inhibitor" means an agent inhibits the enzyme, microsomal triglyceride transfer protein.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to PTP1B is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Protein tyrosine phosphatase 1B" or "PTP1B" (also known as PTPN1; protein tyrosine phosphatase, non-receptor type 1; PTP-1B; RKPTP) means any nucleic acid or protein of PTP1B.

"PTP1B expression" means the level of mRNA transcribed from the gene encoding PTP1B or the level of protein translated from the mRNA. PTP1B expression can be determined by art known methods such as a Northern or Western blot.

"PTP1B nucleic acid" means any nucleic acid encoding PTP1B. For example, in certain embodiments, a PTP1B nucleic acid includes a DNA sequence encoding PTP1B, a RNA sequence transcribed from DNA encoding PTP1B (including genomic DNA comprising introns and exons), and a mRNA sequence encoding PTP1B. "PTP1B mRNA" means a mRNA encoding a PTP1B protein.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

CERTAIN EMBODIMENTS

Certain embodiments provide methods, compounds, and compositions for inhibiting PTP1B expression.

Certain embodiments provide antisense compounds targeted to a PTP1B nucleic acid. In certain embodiments, the PTP1B nucleic acid is any of the sequences set forth in GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP1B scaffold (incorporated herein as SEQ ID NO: 3).

In certain embodiments, the compounds or compositions provided herein comprise a modified oligonucleotide consisting of 10 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 10 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-32 or 100-111.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 26 or 44.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of ISIS NO: 404173

In certain embodiments, the compounds or compositions provided herein comprise a modified oligonucleotide consisting of 15 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 15 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-32 or 100-111.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 26 or 44.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of ISIS NO: 404173

In certain embodiments, the compounds or compositions provided herein comprise a modified oligonucleotide consisting of 18 to 21 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 18 to 21 linked nucleosides and having a nucleobase sequence comprising at least 8, 9, 10, 11, 12, 13, 14, 15, 16, 17, 18, 19, 20, or 21 contiguous nucleobases complementary to an equal length portion of any of SEQ ID NOs: 1-3.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 4-32 or 39-49.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or 20 contiguous nucleobases of any of SEQ ID NOs: 26 or 44.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 to 35 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 35 linked nucleosides and having a nucleobase sequence comprising at least 8, 9, 10, 11, 12, 13, 14, 15, 16, 17, 18, 19, 20, 21, 22, 23, 24, 25, 26, 27, 28, 29, 30, 31, 32, 33, 34 or 35 contiguous nucleobases complementary to an equal length portion of any of SEQ ID NOs: 1-3.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or 20 contiguous nucleobases of SEQ ID NOs: 4-32 or 50.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or 20 contiguous nucleobases of SEQ ID NO: 4-32 or 50.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438383, 438445, 438454, 438463, or 438472, In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 to 25 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 25 linked nucleosides and having a nucleobase sequence comprising at least 8, 9, 10, 11, 12, 13, 14, 15, 16, 17, 18, 19, 20, 21, 22, 23, 24, or 25 contiguous nucleobases complementary to an equal length portion of any of SEQ ID NOs: 1-3.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438383, 438445, 438454, 438463, or 438472, In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions of the invention comprise a modified oligonucleotide consisting of 20 to 24 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 24 linked nucleosides and having a nucleobase sequence comprising at least 8, 9, 10, 11, 12, 13, 14, 15, 16, 17, 18, 19, 20, 21, 22, 23, or 24 contiguous nucleobases complementary to an equal length portion of any of SEQ ID NOs: 1-3.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or 20 contiguous nucleobases of ISIS NO: 404173

In certain embodiments, the compounds or compositions provided herein comprise a modified oligonucleotide consisting of 20 to 23 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 23 linked nucleosides and having a nucleobase sequence comprising at least 8, 9, 10, 11, 12, 13, 14, 15, 16, 17, 18, 19, 20, 21, 22, or 23 contiguous nucleobases complementary to an equal length portion of any of SEQ ID NOs: 1-3.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 to 22 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 22 linked nucleosides and having a nucleobase sequence comprising at least 8, 9, 10, 11, 12, 13, 14, 15, 16, 17, 18, 19, 20, 21, or 22 contiguous nucleobases complementary to an equal length portion of any of SEQ ID NOs: 1-3.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 to 21 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 21 linked nucleosides and having a nucleobase sequence comprising at least 8, 9, 10, 11, 12, 13, 14, 15, 16, 17, 18, 19, 20, or 21 contiguous nucleobases complementary to an equal length portion of any of SEQ ID NOs: 1-3.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or 20 contiguous nucleobases of ISIS NO: 404173.

In certain embodiments, the compounds or compositions provided herein comprise a modified oligonucleotide consisting of 20 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 linked nucleosides and having a nucleobase sequence comprising at least 8, 9, 10, 11, 12, 13, 14, 15, 16, 17, 18, 19, or 20 contiguous nucleobases complementary to an equal length portion of any of SEQ ID NOs: 1-3.

In certain embodiments, the compounds or compositions provided herein consist of 20 linked nucleosides and have a nucleobase sequence comprising at least 8, 9, 10, 11, 12, 13, 14, 15, 16, 17, 18, 19, or 20 contiguous nucleobases of SEQ ID NOs: 4-32.

In certain embodiments, the compounds or compositions provided herein consist of 20 linked nucleosides and have a nucleobase sequence comprising at least 8, 9, 10, 11, 12, 13, 14, 15, 16, 17, 18, 19, or 20 contiguous nucleobases of SEQ ID NO: 26.

In certain embodiments, the compounds or compositions provided herein consist of any of ISIS NOs: 404173, 410002, 438373, 438383, 438445, 438454, 438463, or 438472.

In certain embodiments, the compounds or compositions provided herein consist of ISIS NO: 404173.

In certain embodiments, the compounds or compositions provided herein consist of SEQ ID NO: 26.

In certain embodiments, the compounds or compositions provided herein comprise a salt of the modified oligonucleotide.

In certain embodiments, the compounds or compositions provided herein further comprise a pharmaceutically acceptable carrier or diluent.

In certain embodiments, the nucleobase sequence of the modified oligonucleotide is at least 70%, 75%, 80%, 85%, 90%, 95%, 96%, 97%, 98%, 99% or 100% complementary to any one of SEQ ID NOs: 1-3 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NO: 4-32 or 39-50. as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NO: 26 or 44. as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one ISIS NOs: 404173, 410002, 438373, 438383, 438445, 438454, 438463, or 438472 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to ISIS NO: 404173 as measured over the entirety of the modified oligonucleotide.

In certain embodiments, the compound provided herein consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 20 linked nucleosides. In certain embodiments, the modified oligonucleotide consists of 18 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of eight linked deoxynucleosides, the 5' wing segment consisting of six linked nucleosides, the 3' wing segment consisting of six linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of thirteen linked deoxynucleosides, the 5' wing segment consisting of two linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 18 linked nucleosides, the gap segment consisting of eight linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 18 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of eight linked deoxynucleosides; b) a 5' wing segment consisting of six linked nucleosides; and c) a 3' wing segment consisting of six linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 4-32, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having the nucleobase sequence of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 26 or 44, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound of any of ISIS NOs: 404173, 410002, 438383, 438445, 438454, 438463, or 438472.

In certain embodiments, the compounds or compositions provided herein comprise a modified oligonucleotide consisting of 20 linked nucleosides having a nucleobase sequence comprising at least 20 contiguous nucleobases of SEQ ID NOs: 4-32, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound ISIS NOs: 404173.

Certain embodiments provide methods, compounds, and compositions for inhibiting PTP1B expression.

Certain embodiments provide a method of reducing PTP1B expression in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 to 35 linked nucleosides in length targeted to PTP1B. In certain embodiments, the compound comprises a modified oligonucleotide 20 to 25 linked nucleosides in length targeted to PTP1B. In certain embodiments, the compound comprises a modified oligonucleotide 20 to 24 linked nucleosides in length targeted to PTP1B. In certain embodiments, the compound comprises a modified oligonucleotide 20 to 23 linked nucleosides in length targeted to PTP1B. In certain embodiments, the compound comprises a modified oligonucleotide 20 to 22 linked nucleosides in length targeted to PTP1B. In certain embodiments, the compound comprises a modified oligonucleotide 20 to 21 linked nucleosides in length targeted to PTP1B. In certain embodiments, the compound comprises a modified oligonucleotide 20 linked nucleosides in length targeted to PTP1B.

Certain embodiments provide a method of preventing, ameliorating or treating an metabolic disease in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 linked nucleosides in length targeted to PTP1B. Examples of metabolic diseases or disorders include, but are not limited to obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide a method of reducing glucose levels in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 linked nucleosides in length targeted to PTP1B. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

In certain embodiments, PTP1B has the sequence as set forth in any of the GenBank Accession Numbers GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP scaffold (incorporated herein as SEQ ID NO: 3). In certain embodiments, PTP has the human sequence as set forth in SEQ ID NOs: 1-2. In certain embodiments, PTP1B has the rhesus monkey sequence as set forth in SEQ ID NOs: 3).

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NOs: 4-32, 50 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NOs: 4-32, 50 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 4-32, 50 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NO: 26 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NO: 26 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 26 or a salt thereof and a pharmaceutically acceptable carrier or diluent.

In certain embodiments, the compounds or compositions of the invention comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent.

In certain embodiments, the compounds or compositions of the invention comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent.

Certain embodiments provide a method for treating an animal with a PTP1B related disease or condition comprising: a) identifying said animal with the PTP1B related disease or condition, and b) administering to said animal a therapeutically effective amount of a compound comprising a modified oligonucleotide consisting of 10 to 30 linked nucleosides and having a nucleobase sequence at least 90% complementary to any of SEQ ID NOs: 1-3 as measured over the entirety of said modified oligonucleotide. In certain embodiments, the therapeutically effective amount of the compound administered to the animal treats or reduces the PTP1B related disease or condition, or a symptom thereof, in the animal. In certain embodiments, the PTP1B related disease or condition is diabetes.

Certain embodiments provide a method for treating an animal with a PTP1B related disease or condition comprising: a) identifying said animal with the PTP1B related disease or condition, and b) administering to said animal a therapeutically effective amount of a compound comprising a modified oligonucleotide consisting of 20 linked nucleosides and having a nucleobase sequence at least 100% complementary to any of SEQ ID NOs: 1-3 as measured over the entirety of said modified oligonucleotide. In certain embodiments, the therapeutically effective amount of the compound administered to the animal treats or reduces the PTP1B related disease or condition, or a symptom thereof, in the animal. In certain embodiments, the PTP1B related disease or condition is diabetes.

Certain embodiments provide methods of treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide methods of treating, preventing, or ameliorating a hyperproliferative disorder.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence recited in SEQ ID NOs: 4-32 or 50 Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence recited in SEQ ID NO: 26.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 404173.

In certain embodiments, the animal is a human.

In certain embodiments, the administering prevents, treats, ameliorates, or slows progression of a metabolic disease as described herein.

In certain embodiments, the administering prevents, treats, ameliorates, or slows progression of diabetes as described herein.

In certain embodiments, the compound is co-administered with a second agent.

In certain embodiments, the compound and the second agent are administered concomitantly.

In certain embodiments, the administering is parenteral administration.

Certain embodiments further provide a method to reduce PTP1B mRNA or protein expression in an animal comprising administering to the animal a compound or composition as described herein to reduce PTP1B mRNA or protein expression in the animal. In certain embodiments, the animal is a human. In certain embodiments, reducing PTP1B mRNA or protein expression prevents, treats, ameliorates, or slows progression of metabolic disease. In certain embodiments, the metabolic disease or condition is diabetes.

Certain embodiments provide a method for treating a human with a metabolic disease comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with diabetes comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Further provided is a method for reducing or preventing metabolic disease comprising administering to a human a therapeutically effective amount compound or composition as described herein, thereby reducing or preventing metabolic disease.

Further provided is a method for reducing or preventing diabetes comprising administering to a human a therapeutically effective amount compound or composition as described herein, thereby reducing or preventing diabetes.

Further provided is a method for ameliorating a symptom of metabolic disease, comprising administering to a human in need thereof a compound comprising a modified oligonucleotide consisting of 20 to 35 linked nucleosides, wherein said modified oligonucleotide specifically hybridizes to SEQ ID NO: 1, 2, or 3, thereby ameliorating a symptom of metabolic disease in the human.

Further provided is a method for ameliorating a symptom of diabetes, comprising administering to a human in need thereof a compound comprising a modified oligonucleotide consisting of 10 to 30 linked nucleosides, wherein said modified oligonucleotide specifically hybridizes to SEQ ID NO: 1, 2, or 3, thereby ameliorating a symptom of diabetes in the human.

Further provided is a method for ameliorating a symptom of diabetes, comprising administering to a human in need thereof a compound comprising a modified oligonucleotide consisting of 20 linked nucleosides, wherein said modified oligonucleotide specifically hybridizes to SEQ ID NO: 1, 2, or 3, thereby ameliorating a symptom of diabetes in the human.

Further provided is a method for reducing the rate of progression of a symptom associated with metabolic disease, comprising administering to a human in need thereof a compound comprising a modified oligonucleotide consisting of 10 to 30 linked nucleosides, wherein said modified oligonucleotide specifically hybridizes to SEQ ID NO: 1, 2, or 3, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 20 to 35 linked nucleosides, wherein said modified oligonucleotide specifically hybridizes to SEQ ID NO: 1, 2, or 3, thereby reducing the rate of progression a symptom of diabetes in the human.

Further provided is a method for reducing the rate of progression of a symptom associated with diabetes, comprising administering to a human in need thereof a compound comprising a modified oligonucleotide consisting of 20 linked nucleosides, wherein said modified oligonucleotide specifically hybridizes to SEQ ID NO: 1, 2, or 3, thereby reducing the rate of progression a symptom of diabetes in the human.

Also provided are methods and compounds for the preparation of a medicament for the treatment, prevention, or amelioration of metabolic disease.

Also provided are methods and compounds for the preparation of a medicament for the treatment, prevention, or amelioration of diabetes.

Certain embodiments provide the use of a compound as described herein in the manufacture of a medicament for treating, ameliorating, or preventing metabolic disease.

Certain embodiments provide the use of a compound as described herein in the manufacture of a medicament for treating, ameliorating, or preventing diabetes.

Certain embodiments provide a compound as described herein for use in treating, preventing, or ameliorating metabolic disease as described herein by combination therapy with an additional agent or therapy as described herein. Agents or therapies can be co-administered or administered concomitantly.

Certain embodiments provide a compound as described herein for use in treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein in a patient who is subsequently administered an additional agent or therapy as described herein.

Certain embodiments provide the use of a compound as described herein in the manufacture of a medicament for treating, preventing, or ameliorating diabetes as described herein in a patient who is subsequently administered an additional agent or therapy as described herein.

Certain embodiments provide a kit for treating, preventing, or ameliorating metabolic disease as described herein wherein the kit comprises:
(i) a compound as described herein; and alternatively
(ii) an additional agent or therapy as described herein.

Certain embodiments provide a kit for treating, preventing, or ameliorating diabetes as described herein wherein the kit comprises:
(i) a compound as described herein; and alternatively
(ii) an additional agent or therapy as described herein.

A kit as described herein may further include instructions for using the kit to treat, prevent, or ameliorate metabolic disease as described herein by combination therapy as described herein. In certain embodiments, the metabolic disease is diabetes.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a PTP1B nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a PTP1B nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, antisense compounds targeted to a PTP1B nucleic acid possess a 5-10-5 gapmer motif.

In certain embodiments, antisense compounds targeted to a PTP1B nucleic acid possess a 6-8-6 gapmer motif.

In certain embodiments, antisense compounds targeted to a PTP1B nucleic acid possess a 5-8-5 gapmer motif.

In certain embodiments, an antisense compound targeted to a PTP1B nucleic acid has a gap-widened motif.

In certain embodiments, antisense compounds targeted to a PTP1B nucleic acid possess a 2-13-5 gap-widened motif.

Target Nucleic Acids, Target Regions and Nucleotide Sequences

In certain embodiments, the PTP1B nucleic acid is any of the sequences set forth in GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP1B scaffold (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for PTP1B can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in PTP1B mRNA levels are indicative of inhibition of PTP1B expression. Reductions in levels of a PTP1B protein are also indicative of inhibition of target mRNA expression. Further, phenotypic changes are indicative of inhibition of PTP1B expression. In certain embodiments, reduced glucose levels, reduced lipid levels, and reduced body weight can be indicative of inhibition of PTP1B expression. In certain embodiments, amelioration of symptoms associated with metabolic disease can be indicative of inhibition of PTP1B expression. In certain embodiments, amelioration of symptoms associated with diabetes can be indicative of inhibition of PTP1B expression. In certain embodiments, reduction of insulin resistance is indicative of inhibition of PTP1B expression. In certain embodiments, reduction of diabetes biomarkers can be indicative of inhibition of PTP1B expression.

Hybridization

In some embodiments, hybridization occurs between an antisense compound disclosed herein and a PTP1B nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a PTP1B nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a PTP1B nucleic acid).

An antisense compound may hybridize over one or more segments of a PTP1B nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a PTP1B nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a PTP1B nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and for the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a PTP1B nucleic acid, or a specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a PTP1B nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. In certain embodiments, the antisense compounds are complementary to at least a 16 nucleobase portion of a target segment. In certain embodiments, the antisense compounds are complementary to at least a 17 nucleobase portion of a target segment. In certain embodiments, the antisense compounds are complementary to at least a 18 nucleobase portion of a target segment. In certain embodiments, the antisense compounds are complementary to at least a 19 nucleobase portion of a target segment. In certain embodiments, the antisense compounds are complementary to at least a 20 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a PTP1B nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substituent groups (including 5' and 2' substituent groups); bridging of non-geminal ring atoms to form bicyclic nucleic acids (BNA); replacement of the ribosyl ring oxygen atom with S, N(R), or C(R1)(R)2 (R=H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-OCH$_3$, and 2'-O(CH$_2$)2OCH$_3$ substituent groups. The substituent at the 2' position can also be selected from allyl, amino, azido, thio, O-allyl, O—C$_1$-C$_{10}$ alkyl, OCF$_3$, O(CH$_2$)2SCH$_3$, O(CH$_2$)2-O—N(Rm)(Rn), and O—CH$_2$—C(=O)—N(Rm)(Rn), where each Rm and Rn is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845, issued on Jul. 15, 2008); 4'-C(CH$_3$)(CH$_3$)—O-2', and analogs thereof (see, published PCT International Application WO2009/006478, published Jan. 8, 2009); 4'-CH$_2$—N(OCH$_3$)-2', and analogs thereof (see, published PCT International Application WO2008/150729, published Dec. 11, 2008); 4'-CH$_2$—O—N(CH$_3$)-2' (see, published U.S. Patent Application US2004/0171570, published Sep. 2, 2004); 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, Chattopadhyaya, et al., *J. Org. Chem.*, 2009, 74, 118-134); and 4'-CH$_2$—C(=CH$_2$)-2', and analogs thereof (see, published PCT International Application WO 2008/154401, published on Dec. 8, 2008). Also see, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

In certain embodiments, the bridge of a bicyclic sugar moiety is, —[C(R$_a$)(R$_b$)]$_n$—, —[C(R$_a$R$_b$)]$_n$—O—, —C(R$_a$R$_b$)—N(R)—O— or, —C(R$_a$R$_b$)—O—N(R)—. In certain embodiments, the bridge is 4'-CH$_2$-2',4'-(CH$_2$)$_2$-2',4'-(CH$_2$)$_3$-2',4'-CH$_2$—O-2',4'-(CH$_2$)$_2$—O-2',4'-CH$_2$—O—N(R)-2', and 4'-CH$_2$—N(R)—O-2'-, wherein each R is, independently, H, a protecting group, or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA, (G) methylene-thio (4'-CH$_2$—S-2') BNA, (H) methyleneamino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_{3-2}$') BNA as depicted below.

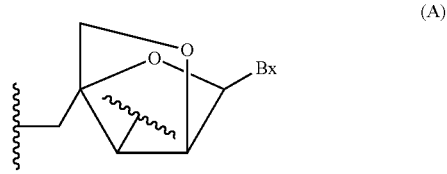

(A)

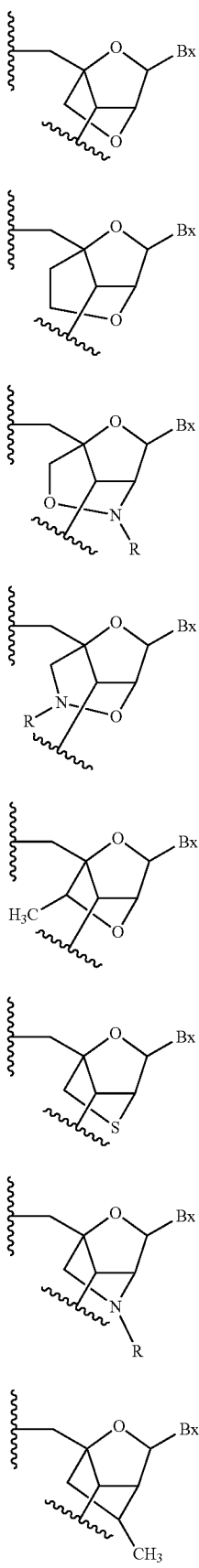

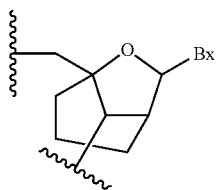

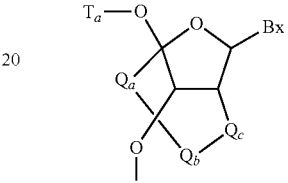

wherein Bx is the base moiety and R is, independently, H, a protecting group or $C_1$-$C_{12}$ alkyl.

In certain embodiments, bicyclic nucleoside having Formula I:

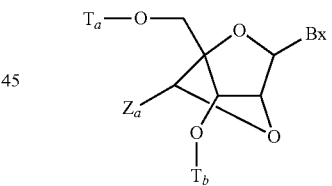

wherein:
Bx is a heterocyclic base moiety;
-($Q_a$-$Q_b$-$Q_c$)- is —$CH_2$—N($R_c$)—$CH_2$—, —C(=O)—N($R_c$)—$CH_2$—, —$CH_2$—O—N($R_c$)—, —$CH_2$—N($R_c$)—O—, or —N($R_c$)—O—$CH_2$;
$R_c$ is $C_1$-$C_{12}$ alkyl or an amino protecting group; and
$T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

$$\text{II}$$

wherein:
Bx is a heterocyclic base moiety;
$T_a$ and $T_b$ are each, independently, H, a hydroxyl protecting group, a conjugate group, a reactive phosphorus group, a phosphorus moiety, or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

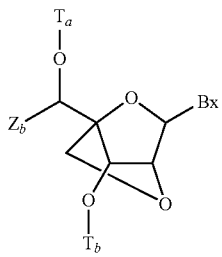

III wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

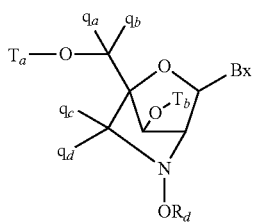

IV wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

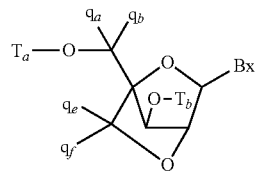

V wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA, methyleneoxy (4'-CH$_2$—O-2') BNA, and 2'-thio-BNAs, have also been prepared (see, e.g., Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleoside having Formula VI:

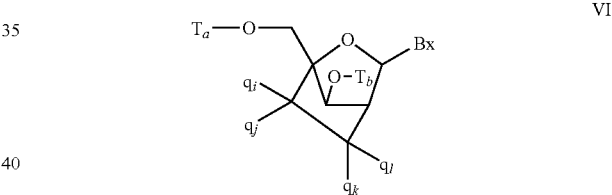

VI wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-(CH$_2$)$_{3}$-2' bridge and the alkenyl analog, bridge 4'-CH=CH—CH$_2$-2', have been described (see, e.g., Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such T-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F—HNA), or those compounds having Formula X:

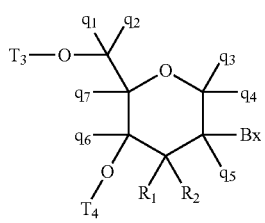

wherein independently for each of said at least one tetrahydropyran nucleoside analog of Formula X:
Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-OCH$_3$" or "2'-O-methyl" each refers to a sugar comprising an —OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C\equiv C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a PTP1B nucleic acid comprise one or more modified nucleobases. In certain embodiments, gap-widened antisense oligonucleotides targeted to a PTP1B nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a PTP1B nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally.

Accordingly, in one embodiment, employed in the methods described herein is a pharmaceutical composition comprising an antisense compound targeted to a PTP1B nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of PTP1B nucleic acids can be tested in vitro in a variety of cell types. Cell types used for such analyses are available from commercial vendors (e.g. American Type Culture Collection, Manasss, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE 2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a PTP1B nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISMS 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a PTP1B nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of PTP1B nucleic acids can be assessed by measuring PTP1B protein levels. Protein levels of PTP1B can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat PTP1B are commercially available.

In Vivo Testing of Antisense Compounds

Antisense compounds, for example, antisense oligonucleotides, are tested in animals to assess their ability to inhibit expression of PTP1B and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in PTP1B nucleic acid expression are measured. Changes in PTP1B protein levels are also measured.

Certain Indications

In certain embodiments, provided herein are methods of treating an individual comprising administering one or more pharmaceutical compositions as described herein. In certain embodiments, the individual has metabolic related disease.

As shown in the examples below, compounds targeted to PTP1B, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain. In certain of the experiments, the compounds reduced blood glucose levels, e.g., the animals continued to experience symptoms, but the symptoms were less severe compared to untreated animals. In other of the experiments, however, the compounds appear to reduce the symptoms of diabetes; e.g., animals treated for a longer period of time experienced less severe symptoms than those administered the compounds for a shorter period of time. In other of the experiments, however, the compounds appear to inhibit weight gain; e.g., animals treated for a longer period of time experienced less severe symptoms than those administered the compounds for a shorter period of time. In other of the experiments, however, the compounds appear to inhibit hypertriglyceridemia; e.g., animals treated for a longer period of time experienced less severe symptoms than those administered the compounds for a shorter period of time. The ability of the compounds exemplified below to restore function therefore demonstrates that symptoms of the disease may be reversed by treatment with a compound as described herein.

Diabetes mellitus is characterized by numerous physical and physiological symptoms. Any symptom known to one of skill in the art to be associated with Type 2 diabetes can be ameliorated or otherwise modulated as set forth above in the methods described above. In certain embodiments, the symptom is a physical symptom selected from the group consisting of increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums.

In certain embodiments, the symptom is a physiological symptom selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom is increased weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the symptom is weight loss. In certain embodiments, the symptom is slow-healing sores. In certain embodiments, the symptom is swollen gums. In certain embodiments, the symptom is increased insulin resistance. In certain embodiments, the symptom is increased fat mass. In certain embodiments, the symptom is decreased metabolic rate. In certain embodiments, the symptom is decreased glucose clearance. In certain embodiments, the symptom is decreased glucose tolerance. In certain embodiments, the symptom is decreased insulin sensitivity. In certain embodiments, the symptom is decreased hepatic insulin sensitivity. In certain embodiments, the symptom is increased adipose tissue size and weight. In certain embodiments, the symptom is increased body fat. In certain embodiments, the symptom is increased body weight.

Liu and Chernoff have shown that PTP1B binds to and serves as a substrate for the epidermal growth factor receptor (EGFR) (Liu and Chernoff, *Biochem. J.,* 1997, 327, 139-145). Furthermore, in A431 human epidermoid carcinoma cells, PT1B was found to be inactivated by the presence of $H_2O_2$ generated by the addition of EGF. These studies indicate that PTP1B can be negatively regulated by the oxidation state of the cell, which is often deregulated during tumorigenesis (Lee et al., *J. Biol. Chem.,* 1998, 273, 15366-15372).

Overexpression of PTP1B has been demonstrated in malignant ovarian cancers and this correlation was accompanied by a concomitant increase in the expression of the associated growth factor receptor (Wiener et al., *Am. J. Obstet. Gynecol.,* 1994, 170, 1177-1183).

PTP1B has been shown to suppress transformation in NIH3T3 cells induced by the neu oncogene (Brown-Shimer et al., *Cancer Res.,* 1992, 52, 478-482), as well as in rat 3Y1 fibroblasts induced by v-srk, v-src, and v-ras (Liu et al., *Mol. Cell. Biol.,* 1998, 18, 250-259) and rat-1 fibroblasts induced by bcr-abl (LaMontagne et al., *Proc. Natl. Acad. Sci. U.S.A.,* 1998, 95, 14094-14099). It has also been shown that PTP1B promotes differentiation of K562 cells, a chronic myelogenous leukemia cell line, in a similar manner as does an inhibitor of the bcr-abl oncoprotein. These studies describe the possible role of PTP1B in controlling the pathogenesis of chronic myeloid leukemia (LaMontagne et al., *Proc. Natl. Acad. Sci. U.S.A.,* 1998, 95, 14094-14099).

Accordingly, provided herein are methods for ameliorating a symptom associated with hyperproliferative disorders in a subject in need thereof. In certain embodiments, the hyperproliferative disorder is cancer. In certain embodiments, provided herein are methods for ameliorating a symptom associated with cancer. In certain embodiments, provided is a method for reducing the rate of onset of a symptom associated with hyperproliferative disorders. In certain embodiments, provided is a method for reducing the rate of onset of a symptom associated with cancer. In certain embodiments, provided is a method for reducing the severity of a symptom associated with hyperproliferative disorders. In certain embodiments, provided is a method for reducing the severity of a symptom associated with cancer. In such embodiments, the methods comprise administering to an individual in need thereof a therapeutically effective amount of a compound targeted to a PTP1B nucleic acid.

In certain embodiments, provided are methods of treating an individual comprising administering one or more pharmaceutical compositions as described herein. In certain embodiments, the individual has metabolic related disease.

In certain embodiments, administration of an antisense compound targeted to a PTP1B nucleic acid results in reduction of PTP1B expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to transthyretin are used for the preparation of a medicament for treating a patient suffering or susceptible to metabolic related disease.

In certain embodiments, the methods described herein include administering a compound comprising a modified oligonucleotide having a contiguous nucleobases portion as described herein of a sequence recited in SEQ ID NO: 26 (ISIS 404173).

Administration

In certain embodiments, the compounds and compositions as described herein may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. The compounds and compositions as described herein can be administered directly to a tissue or organ.

In certain embodiments, the compounds and compositions as described herein are administered parenterally. "Parenteral administration" means administration through injection or infusion. Parenteral administration includes subcutaneous administration, intravenous administration, intramuscular administration, intraarterial administration, intraperitoneal administration, or intracranial administration, e.g. intracerebral administration, intrathecal administration, intraventricular administration, ventricular administration, intracerebroventricular administration, cerebral intraventricular administration or cerebral ventricular administration. Administration can be continuous, or chronic, or short or intermittent.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, the compounds and compositions as described herein are administered parenterally.

In certain embodiments, parenteral administration is subcutaneous.

In further embodiments, the formulation for administration is the compounds described herein and saline.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, the second compound is administered prior to administration of a pharmaceutical composition of the present invention. In certain embodiments, the second compound is administered following administration of a pharmaceutical composition of the present invention. In certain embodiments, the second compound is administered at the same time as a pharmaceutical composition of the present invention. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments, second agents include, but are not limited to, a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose-lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose-lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain embodiments, second agents include, but are not limited to, lipid-lowering agents. The lipid-lowering agent can include, but is not limited to atorvastatin, simvastatin, rosuvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, second agents include, but are not limited to an anti-obesity drug or agent. Such anti-obesity agents include but are not limited to Orlistat, Sibutramine, or Rimonabant, and may be administered as described above as adipose or body weight lowering agents. In certain embodiments, the antisense compound may be co-administered with appetite suppressants. Such appetite suppressants include but are not limited to diethylpropion tenuate, mazindol, orlistat, phendimetrazine, phentermine, and sibutramine and may be administered as described herein. In certain embodiment, the anti-obesity agents are CNS based such as, but not limited to, sibutramine or GLP-1 based such as, but not limited to, liraglutide.

Formulations

The compounds provided herein may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds provided herein encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds provided herein: i.e., salts that retain the desired biological activity of the parent compound and do not impart undesired toxicological effects thereto. The term "pharmaceutically acceptable salt" includes a salt prepared from pharmaceutically acceptable non-toxic acids or bases, including inorganic or organic acids and bases. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The term "pharmaceutically acceptable derivative" encompasses, but is not limited to, pharmaceutically acceptable salts, solvates, hydrates, esters, prodrugs, polymorphs, isomers, isotopically labeled variants of the compounds described herein.

The present invention also includes pharmaceutical compositions and formulations which include the antisense compounds provided herein. The pharmaceutical compositions of the present invention may be administered in a number of ways depending upon whether local or systemic treatment is desired and upon the area to be treated. Administration may be parenteral. Parenteral administration includes intravenous, intraarterial, subcutaneous, intraperitoneal or intramuscular injection or infusion; or intracranial, e.g., intracerebral administration, intrathecal administration, intraventricular administration, ventricular administration, intracerebroventricular administration, cerebral intraventricular administration or cerebral ventricular administration.

Parenteral administration, is preferred to target PTP1B expression in the liver and plasma. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment, formulations of the present invention include saline formulations. In certain embodiments, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions of the present invention may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligonucleotides provided herein are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions and formulations for parenteral administration, including intravenous, intraarterial, subcutaneous, intraperitoneal, intramuscular injection or infusion, or intracranial may include sterile aqueous solutions which may also contain buffers, diluents and other suitable additives such as, but not limited to, penetration enhancers, carrier compounds and other pharmaceutically acceptable carriers or excipients.

Certain embodiments provided herein provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds provided herein, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions provided herein. Combinations of antisense compounds and other non-antisense drugs are also within the scope of this invention. Two or more combined compounds may be used together or sequentially.

In another related embodiment, compositions provided herein may contain one or more antisense compounds, particularly oligonucleotides, targeted to a first nucleic acid and one or more additional antisense compounds targeted to a second nucleic acid target. Alternatively, compositions provided herein may contain two or more antisense compounds targeted to different regions of the same nucleic acid target.

Numerous examples of antisense compounds are known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

Certain Compounds

About two hundred and seventy six newly designed antisense compounds of various lengths, motifs and backbone composition were tested for their effect on human PTP1B mRNA in vitro in several cell types. The new compounds were compared with about five hundred previously designed compounds including ISIS 107772, ISIS 107831, ISIS 142025, ISIS 142026, ISIS 142027, ISIS 142028, ISIS 142082, ISIS 146908, and ISIS 146909 which have previously been determined to be some of the most potent antisense compounds in vitro (see e.g., U.S. Patent Publication No. US 2003/0220282 published Nov. 27, 2003 and PCT Patent Publication No. WO2007/131237 published Nov. 15, 2007). Of the about two hundred and eight five newly designed and previously designed antisense compounds, about eleven compounds were selected for further study based on in vitro potency. The selected compounds were tested for dose dependent inhibition in HuVEC, HepG2, HuVEC, LLC-MK2, and cynomolgus primary hepatocytes. Additional oligonucleotides were designed based on microwalk of ISIS 409826, one of the selected compounds which demonstrated significant reduction of PTP1B mRNA in all the cell lines tested. The oligonucleotides were tested in HuVEC cells (Example 5) along with gapmers from the earlier screen (Example 1). Several antisense oligonucleotides from the screen in Example 5 were selected and tested for dose-dependent inhibition in HuVEC cells (Example 6) and HepG2 cells (Example 7). Additionally, two oligonucleotides were designed as shortmers to ISIS 1428082, one of the selected compounds. These two shortmers (ISIS 446431 and ISIS 446432), as well as five ISIS oligonucleotides selected from the study described in Examples 6 and 7 were tested in HepG2 cells, LLC-MK2 cells, HuVEC cells, and cynomolgus primary hepatocytes (Examples 8-11). ISIS oligonucleotides that demonstrated dose-dependent reduction of PTP1B mRNA in all cell lines were tested for in vivo tolerability. Two more oligonucleotides ISIS 446433 and ISIS 446434, designed as shortmers to ISIS 409826, were included in the in vivo tolerability studies as well.

The twelve gapmers chosen were tested in a mouse model (see Example 12) and a rat model (Example 13). By virtue of their complementary sequence, the compounds are complementary to the regions 3291-3310, 989-1008, 3290-3309, 3287-3306, 3291-3310, 3288-3307, 3292-3309, 3293-3308, 3288-3305, and 3289-3304 of SEQ ID NO: 1. In the in vivo models, body weights and organ weights, the liver metabolic markers, such as alanine transaminase, aspartate transaminase and bilirubin, kidney metabolic markers, such as BUN and creatinine, plasma glucose levels, cholesterol and triglyceride levels, and inflammatory cytokine levels were measured. Of the twelve compounds tested, five compounds, ISIS 142082, ISIS 404173, ISIS 410003, ISIS 446431, and ISIS 446432 were selected and their viscosity was measured (Example 14). All the five oligonucleotides were considered optimal in their viscosity according to the criteria stated for the study.

Final evaluation of these studies (Examples 12-14), led to the selection of four compounds having a nucleobase sequence of a sequence recited in SEQ ID NO: 27 (ISIS 142082), 46 (ISIS 446431), 26 (ISIS 404173), and 23 (ISIS 409826). By virtue of their complementary sequence, the compounds are complementary to the regions 3291-3310, 3292-3309, 3290-3309, 3287-3306 of SEQ ID NO: 1. In certain embodiments, the compounds targeting the listed regions, as further described herein, comprise a modified oligonucleotide having some nucleobase portion of the sequence recited in the SEQ ID NOs, as further described herein, In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif, as indicated by the ISIS NOs: ISIS 142082, ISIS 446431, ISIS 404173, and ISIS 409826.

Three compounds having a nucleobase sequence of a sequence recited in SEQ ID NO: 27 (ISIS 142082), 23 (ISIS 404173), and 46 (ISIS 446431), were further tested in a long-term, six month tolerability study in a mouse model (See Example 15). The half life in the liver of CD1 mice of all four of the compounds having a nucleobase sequence of a sequence recited in SEQ ID NOs: 53 (ISIS 409826), 27 (ISIS 142082), 26 (ISIS 404173), and 46 (ISIS 446431) was also evaluated (Example 16).

These four compounds were tested for efficacy, pharmacokinetic profile and tolerability in cynomolgus monkeys (Example 17). The inhibition studies in these monkeys indicated that treatment with some of these compounds caused reduction of PTP1B mRNA in the liver and fat tissues. Specifically, treatment with ISIS 409826, ISIS 142082, ISIS 446431 and ISIS 404173 caused 45%, 48%, 18 and 22% reduction of PTP1B mRNA in liver tissue, respectively compared to the PBS control. Treatment with ISIS 409826, ISIS 142082, ISIS 446431 and ISIS 404173 caused 21%, 28%, 12% and 31% reduction of PTP1B mRNA in fat tissue, respectively compared to the PBS control. It was noted that ISIS 404173 caused similar reduction of PTP1B mRNA compared to ISIS 142082, even though the two oligonucleotides differ from each other by a single base-pair shift of their target region on SEQ ID NO: 1. Protein analysis of liver tissue was also conducted by western blot analysis. PTP1B mRNA reduction using ISIS 409826, ISIS 142082, ISIS 446431 and ISIS 404173 was measured at a maximum dose of 40 mgk/week for efficacy and at a lower dose of 8 mgk/week for potency (See table 45). Protein analysis at a lower dose of 8 mgk/week demonstrated that ISIS 404173 caused greater reduction (33%) of PTP1B protein than ISIS 142082 (20%) demonstrating that ISIS 404173 was more potent than ISIS 142082 (See Table 47 and FIG. 1). Protein analysis at the higher dose of 40 mg/week demonstrated that ISIS 404173 (60% protein reduction) was as efficacious as ISIS 142082 (65% protein reduction). Finally, treatment with ISIS 409826 and ISIS 142082 resulted in 22% decrease in triglyceride levels while treatment with ISIS 404173 resulted in 37% decrease in triglyceride levels compared to the PBS control.

Tolerability studies in cynomolgus monkeys (Example 17) indicated that treatment with ISIS 142082 was not as tolerable to the primates as treatment with ISIS 404173. The levels of C-reactive protein, which is synthesized in the liver and which serves as a marker of inflammation, were measured on day 93. At the higher dose of 40 mg/week, treatment with ISIS 142082 caused a significant increase of CRP levels of 12 mg/L compared to the control level of 1.2 mg/L. Treatment with ISIS 404173 at 40 mg/L caused an increase of CRP levels to 1.6 mg/L. The other compounds tested, ISIS 409826 and ISIS 446431 caused increase of CRP levels to 4.8 mg/L and 6.7 mg/L. Therefore, ISIS 404173 caused the least increase in CRP levels indicating that ISIS 404173 is extremely tolerable and non-proinflammatory. Organ weights were also measured to evaluate the tolerability of ISIS oligonucleotides by the monkeys. Treatment with ISIS 142082 at a dose of 40 mg/L caused increases in kidney and liver weights of 21 g and 18 g respectively, which is two-fold increase over the control (kidney 10 g and liver 10.5 g). Treatment with ISIS 409826 caused a two-fold increase in liver weight (18.5 g vs. 10.5 g of control) and a three-fold increase in spleen weight (6.0 g vs. 2.3 g of control). Treatment with ISIS 446431 caused a four-fold increase in spleen weight (9.6 g vs. 2.3 g control). Treatment with ISIS 404173 caused less than one-fold increase in all organs (kidney 14.8 g; liver 15.5 g; spleen 3.7 g) See (FIG. 2). Hence, treatment with ISIS 142082, ISIS 409826, and ISIS 446431 were not considered tolerable in the monkeys, whereas treatment with ISIS 404173 was tolerable.

Treatment with ISIS 142082 caused increase in organ weights and elevated levels of CRP, indicating an inflammatory state. Treatment with ISIS 409826 also caused elevated levels of CRP and low complement C3 levels, indicating a diseased state. Treatment with ISIS 404173 and ISIS 446431 were considered optimal in terms of their tolerability profiles in cynomolgus monkeys. However, ISIS 446431 demonstrated less potency compared to ISIS 404173.

In case of the pharmacokinetic profile studies of the oligonucleotides in liver and kidney, none of the ISIS oligonucleotides demonstrated any abnormal ratios in concentration in the liver versus the kidney. ISIS 404173 was a better renal accumulator compared to ISIS 142082, as indicated in the results.

Hence, the in vivo studies, particularly in the cynomolgus monkeys, indicate that ISIS 404173 was just as potent and considerably more tolerable compared to the other compounds. The studies demonstrate that ISIS 142082, although shifted from ISIS 407173 by only one nucleobase, was as efficacious but less potent and tolerable than ISIS 404173, as demonstrated by assays for metabolic and inflammatory markers. Overall, ISIS 404173 was more potent and tolerable compared to any other compound.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 1.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 2.

In certain embodiments, the compounds as described herein are efficacious by virtue of having at least one of an in vitro $IC_{50}$ of less than 0.4 µM, less than 0.35 µM, less than 0.3 µM, less than 2.5 µM, less than 2.0 µM, less than 1.5 µM, less than 1.0 µM, when delivered to a cynomolgus monkey hepatocyte cell line using electroporation as described in Example 11. In certain embodiments, the compounds as described herein are highly tolerable, as demonstrated by having at least one of an increase an ALT or AST value of no more than 4 fold, 3 fold, or 2 fold over saline treated animals; or an increase in liver, spleen or kidney weight of no more than 30%, 20%, 15%, 12%, 10%, 5% or 2%.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Example 1

Antisense Inhibition of Human PTP1B mRNA in HuVEC Cells

Antisense oligonucleotides targeted to a human PTP1B nucleic acid were designed and tested for their effect on PTP1B RNA transcript in vitro. ISIS 107772, ISIS 107831, ISIS 142025, ISIS 142026, ISIS 142027, ISIS 142028, ISIS 142082, ISIS 146908, and ISIS 146909, claimed in a previous patent (BIOL001USP2) were included in this assay for comparison. Cultured HuVEC cells at a density of 5,000 cells per well were transfected using LipofectAMINE 2000® with 2 nM antisense oligonucleotide. After approximately 24 hours, RNA was isolated from the cells and PTP1B mRNA levels were measured by quantitative real-time PCR. PTP1B mRNA levels were adjusted according to total RNA content, as measured by RIBOGREEN®. Results are presented as percent inhibition of PTP1B mRNA levels, relative to untreated control cells.

The antisense oligonucleotides in Table 1 are 5-10-5 MOE gapmers or 2-13-5 MOE gapmers. The 5-10-5 MOE gapmers have a gap segment comprising ten 2'-deoxynucleosides and two wing segment comprising five 2'-MOE nucleosides. The 2-13-5 MOE gapmers have a gap segment comprising thirteen 2'-deoxynucleosides, a 5' wing segment comprising two 2'-MOE nucleosides, and a 3' wing segment comprising three 2'-MOE nucleosides. The internucleoside linkages throughout each gapmer are phosphorothioate (P=S) linkages. All cytosine residues throughout each gapmer are 5-methylcytosines. 'Target start site' indicates the 5'-most nucleotide to which the antisense oligonucleotide is targeted in the human gene sequence. 'Target stop site' indicates the 3'-most nucleotide to which the antisense oligonucleotide is targeted in the human gene sequence. All the antisense oligonucleotides listed in Table 1 target either the mRNA sequence, designated herein as SEQ ID NO: 1 (GENBANK Accession No. NM_002827.2) or the genomic sequence, designated herein as SEQ ID NO: 2 (GENBANK Accession NT_011362.9 truncated from nucleotides 14178000 to 14256000), or both.

Some of the human oligonucleotides of Table 1 are also fully cross-reactive with rhesus monkey gene sequences. 'n/a' indicates that there were more than 3 base mismatches between the human oligonucleotide and the rhesus monkey gene sequence. The greater the complementarity between the human oligonucleotide and the rhesus monkey sequence, the more likely the human oligonucleotide can cross-react with the rhesus monkey sequence. The human oligonucleotides in Table 1 were compared to SEQ ID NO: 3 (exons 1-9, intron 9 and exon 10 from the rhesus monkey PTP1B scaffold). "Rhesus monkey Target start site" indicates the 5'-most nucleotide to which the gapmer is targeted in the rhesus monkey gene sequence. "Rhesus monkey Target stop site" indicates the 3'-most nucleotide to which the gapmer is targeted rhesus monkey gene sequence.

TABLE 1

Inhibition of human PTP1B RNA transcript in HuVEC cells by antisense oligonucleotides targeting SEQ ID NO: 1, SEQ ID NO: 2, and SEQ ID NO: 3

| ISIS No | Sequence | Motif | % inhibition | Start Site at SEQ ID NO: 1 | Start Site at SEQ ID NO: 2 | Start Site at SEQ ID NO: 3 | SEQ ID NO |
|---|---|---|---|---|---|---|---|
| 142025 | TTGTCGATCTGCTCGAACTC | 5-10-5 | 43 | 190 | 1989 | 197 | 4 |
| 142026 | GACTTGTCGATCTGCTCGAA | 5-10-5 | 59 | 193 | 1992 | 989 | 5 |
| 107772 | CCCGGACTTGTCGATCTGCT | 5-10-5 | 66 | 197 | 1996 | 3754 | 6 |
| 142027 | GCTCCCGGACTTGTCGATCT | 5-10-5 | 55 | 200 | 1999 | 3759 | 7 |
| 142028 | CCAGCTCCCGGACTTGTCGA | 5-10-5 | 60 | 203 | 2002 | 4498 | 8 |
| 373125 | GGCACCTTCGATCACAGCCA | 5-10-5 | 55 | 989 | 70726 | 4487 | 9 |
| 113715 | GCTCCTTCCACTGATCCTGC | 5-10-5 | 50 | 1035 | n/a | 4500 | 10 |
| 107831 | GGTCATGCACAGGCAGGTTG | 5-10-5 | 70 | 2360 | 75039 | 3753 | 11 |
| 409988 | AGGTCATGCACAGGCAGGTT | 2-13-5 | 83 | 2361 | 75040 | 3759 | 12 |
| 409821 | GATCAGGTCATGCACAGGCA | 5-10-5 | 86 | 2365 | 75044 | 3575 | 13 |
| 404176 | TGATCAGGTCATGCACAGGC | 5-10-5 | 87 | 2366 | 75045 | 4493 | 14 |
| 146908 | ACCCTTGGAATGTCTGAGTT | 5-10-5 | 56 | 2544 | 75223 | 3746 | 15 |
| 404169 | CCCATACCCTTGGAATGTCT | 5-10-5 | 77 | 2549 | 75228 | 3756 | 16 |
| 409815 | TCCCATACCCTTGGAATGTC | 5-10-5 | 72 | 2550 | 75229 | 3566 | 17 |
| 146909 | TTCCCATACCCTTGGAATGT | 5-10-5 | 43 | 2551 | 75230 | 3569 | 18 |
| 409845 | TATTCCATGGCCATTGTAAA | 5-10-5 | 23 | 3283 | 75962 | 4485 | 19 |
| 410030 | TTATTCCATGGCCATTGTAA | 2-13-5 | 24 | 3284 | 75963 | 4486 | 20 |
| 409825 | TTTATTCCATGGCCATTGTA | 5-10-5 | 34 | 3285 | 75964 | 192 | 21 |
| 409883 | GTTTATTCCATGGCCATTGT | 3-14-3 | 36 | 3286 | 75965 | 198 | 22 |
| 409999 | GGTTTATTCCATGGCCATTG | 2-13-5 | 54 | 3287 | 75966 | 190 | 23 |
| 409826 | GGTTTATTCCATGGCCATTG | 5-10-5 | 73 | 3287 | 75966 | 201 | 23 |
| 410000 | TGGTTTATTCCATGGCCATT | 2-13-5 | 55 | 3288 | 75967 | 194 | 24 |
| 404172 | TGGTTTATTCCATGGCCATT | 5-10-5 | 61 | 3288 | 75967 | 192 | 24 |
| 410001 | ATGGTTTATTCCATGGCCAT | 2-13-5 | 51 | 3289 | 75968 | 198 | 25 |
| 409827 | ATGGTTTATTCCATGGCCAT | 5-10-5 | 44 | 3289 | 75968 | 195 | 25 |
| 410002 | AATGGTTTATTCCATGGCCA | 2-13-5 | 0 | 3290 | 75969 | 204 | 26 |
| 404173 | AATGGTTTATTCCATGGCCA | 5-10-5 | 48 | 3290 | 75969 | 201 | 26 |
| 410003 | AAATGGTTTATTCCATGGCC | 2-13-5 | 64 | 3291 | 75970 | 193 | 27 |
| 142082 | AAATGGTTTATTCCATGGCC | 5-10-5 | 52 | 3291 | 75970 | 190 | 27 |

TABLE 1-continued

Inhibition of human PTP1B RNA transcript in HuVEC cells by antisense
oligonucleotides targeting SEQ ID NO: 1, SEQ ID NO: 2, and SEQ ID NO: 3

| ISIS No | Sequence | Motif | % inhibition | Start Site at SEQ ID NO: 1 | Start Site at SEQ ID NO: 2 | Start Site at SEQ ID NO: 3 | SEQ ID NO |
|---|---|---|---|---|---|---|---|
| 410004 | AAAATGGTTTATTCCATGGC | 2-13-5 | 46 | 3292 | 75971 | 196 | 28 |
| 409828 | AAAATGGTTTATTCCATGGC | 5-10-5 | 44 | 3292 | 75971 | 194 | 28 |
| 409829 | AAAAATGGTTTATTCCATGG | 5-10-5 | 36 | 3293 | 75972 | 198 | 29 |
| 404161 | GGTCATTTCCATGGCCAGAG | 2-13-5 | 78 | n/a | 73855 | 3746 | 31 |
| 409975 | GGAGGTCATTTCCATGGCCA | 2-13-5 | 85 | n/a | 73858 | n/a | 32 |
| 409976 | AGGAGGTCATTTCCATGGCC | 2-13-5 | 85 | n/a | 73859 | 2379 | 30 |

Example 2

Dose-Dependent Antisense Inhibition of Human PTP1B mRNA in HuVEC Cells

Several antisense oligonucleotides, which displayed significant antisense inhibition of PTP1B mRNA in the study described in Example 1 were further tested in HuVEC cells at various doses. Cells were plated at a density of 5,000 cells per well and transfected using LipofectAMINE 2000® with 0.9375 nM, 1.875 nM, 3.75 nM, 7.5 nM, 15 nM, and 30 nM concentrations of each antisense oligonucleotide. After approximately 16 hours, RNA was isolated from the cells and PTP1B mRNA transcript levels were measured by quantitative real-time PCR using primer probe set RTS3000 (forward sequence CTGGTTTAACCTCCTATCCTTGGA, designated herein as SEQ ID NO: 33; reverse sequence CAGAG-CAGCTCGCTACCTCTCT, designated herein as SEQ ID NO: 34, probe sequence CAGCTGGCTCTCCACCTTGT-TACACATTATGT, designated herein as SEQ ID NO: 35). PTP1B mRNA levels were normalized to total RNA content, as measured by RIBOGREEN®. Results are presented in Table 2 as percent inhibition of PTP1B mRNA, relative to untreated control cells.

TABLE 2

Dose-dependent antisense inhibition of human PTP1B in HuVEC cells

| ISIS No | 0.9375 nM | 1.875 nM | 3.75 nM | 7.5 nM | 15.0 nM | 30.0 nM | IC$_{50}$ (nM) |
|---|---|---|---|---|---|---|---|
| 113715 | 0 | 0 | 2 | 11 | 23 | 33 | >30 |
| 404161 | 1 | 0 | 7 | 29 | 42 | 57 | 17 |
| 404169 | 0 | 6 | 17 | 37 | 57 | 72 | 7 |
| 404176 | 0 | 0 | 20 | 38 | 68 | 79 | 6 |
| 409815 | 0 | 0 | 7 | 30 | 48 | 65 | 12 |
| 409821 | 0 | 1 | 17 | 41 | 68 | 82 | 5 |
| 409826 | 0 | 0 | 10 | 30 | 47 | 64 | 12 |
| 409975 | 0 | 0 | 23 | 50 | 74 | 86 | 4 |
| 409976 | 0 | 0 | 21 | 46 | 65 | 82 | 5 |
| 409988 | 0 | 0 | 23 | 49 | 70 | 83 | 5 |
| 410003 | 0 | 0 | 4 | 16 | 28 | 46 | >30 |

Example 3

Dose-Dependent Antisense Inhibition of PTP1B mRNA in LLC-MK2 Cells

The antisense oligonucleotides from the study described in Example 2 are also cross-reactive with rhesus monkey the gene sequence (SEQ ID NO: 3) and were further tested in rhesus monkey LLC-MK2 cells at various doses. Cells were plated at a density of 3,000 cells per well and transfected using Lipofectin with 3.125 nM, 6.25 nM, 12.5 nM, 25 nM, 50 nM, and 100 nM concentrations of each antisense oligonucleotide. After approximately 16 hours, RNA was isolated from the cells and PTP1B mRNA levels were measured by quantitative real-time PCR using primer probe set RTS198 (forward sequence GGAGTTCGAGCAGATCGACAA, designated herein as SEQ ID NO: 36; reverse sequence GGC-CACTCTACATGGGAAGTC, designated herein as SEQ ID NO: 37, probe sequence AGCTGGGCGGCCATTTACCAG-GAT, designated herein as SEQ ID NO: 38). PTP1B mRNA levels were normalized to total RNA content, as measured by RIBOGREEN®. Results are presented in Table 3 as percent inhibition of PTP1B mRNA, relative to untreated control cells. The start and stop sites of each oligonucleotide on rhesus monkey SEQ ID NO: 3 (the concatenation of exons 1-9, intron 9 and exon 10 from the rhesus PTP1B scaffold (gene scaffold 240) are presented in Table 4.

TABLE 3

Dose-dependent antisense inhibition of PTP1B mRNA in LLC-MK2 cells

| ISIS No | 3.125 nM | 6.25 nM | 12.5 nM | 25.0 nM | 50.0 nM | 100.0 nM | IC$_{50}$ (nM) |
|---|---|---|---|---|---|---|---|
| 113715 | 9 | 18 | 18 | 42 | 71 | 88 | 12 |
| 404161 | 18 | 26 | 37 | 49 | 67 | 79 | 9 |
| 404169 | 9 | 33 | 36 | 52 | 70 | 85 | 8 |
| 404176 | 4 | 21 | 28 | 52 | 73 | 85 | 10 |
| 409815 | 19 | 27 | 32 | 51 | 67 | 83 | 9 |
| 409821 | 4 | 20 | 37 | 53 | 74 | 85 | 9 |
| 409826 | 7 | 31 | 63 | 46 | 62 | 78 | 8 |
| 409975 | 13 | 20 | 28 | 43 | 62 | 74 | 15 |
| 409976 | 12 | 20 | 37 | 42 | 65 | 77 | 12 |
| 409988 | 3 | 20 | 39 | 56 | 73 | 86 | 8 |
| 410003 | 16 | 24 | 36 | 43 | 65 | 80 | 11 |

TABLE 4

Target sites of antisense oligonucleotides targeting
PTP1B on rhesus monkey gene sequence (SEQ ID NO: 3)

| ISIS No | Start Site | Stop Site |
|---|---|---|
| 113715 | 1035 | 1054 |
| 404161 | 2385 | 2404 |
| 409975 | 2388 | 2407 |

TABLE 4-continued

Target sites of antisense oligonucleotides targeting
PTP1B on rhesus monkey gene sequence (SEQ ID NO: 3)

| ISIS No | Start Site | Stop Site |
|---|---|---|
| 409976 | 2389 | 2408 |
| 409988 | 3566 | 3585 |
| 409821 | 3570 | 3589 |
| 404176 | 3571 | 3590 |
| 404169 | 3754 | 3773 |
| 409815 | 3755 | 3774 |
| 409826 | 4491 | 4510 |
| 410003 | 4495 | 4514 |

Example 4

Dose-Dependent Antisense Inhibition of PTP1B mRNA in Cynomolgus Primary Hepatocytes Some of the antisense oligonucleotides from the study described in Examples 1, 2 and 3 were further tested in cynomolgus primary hepatocytes at various doses. Cells were plated at a density of 35,000 cells per well and transfected using Lipofectin with 6.25 nM, 12.5 nM, 25 nM, 50 nM, 100 nM, and 200 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 5 as percent inhibition of PTP1B mRNA, relative to untreated control cells.

TABLE 5

Dose-dependent antisense inhibition of PTP1B mRNA in cynomolgus primary hepatocytes

| ISIS No | 6.25 nM | 12.5 nM | 25.0 nM | 50.0 nM | 100.0 nM | 200.0 nM | $IC_{50}$ (nM) |
|---|---|---|---|---|---|---|---|
| 373125 | 16 | 4 | 13 | 32 | 48 | 67 | 104 |
| 404161 | 7 | 3 | 24 | 40 | 56 | 77 | 72 |
| 404169 | 0 | 13 | 27 | 44 | 57 | 77 | 67 |
| 404176 | 16 | 17 | 27 | 42 | 64 | 76 | 59 |
| 409815 | 0 | 24 | 26 | 40 | 57 | 75 | 69 |
| 409821 | 0 | 9 | 25 | 37 | 60 | 73 | 73 |
| 409826 | 8 | 28 | 10 | 37 | 56 | 71 | 82 |
| 409975 | 13 | 19 | 29 | 38 | 57 | 75 | 67 |
| 409976 | 2 | 18 | 13 | 35 | 60 | 80 | 70 |
| 409988 | 16 | 22 | 28 | 41 | 59 | 77 | 61 |
| 410003 | 17 | 10 | 37 | 46 | 60 | 78 | 56 |

Example 5

Antisense Inhibition of Human PTP1B mRNA in HuVEC Cells by Oligonucleotides Designed by Microwalk Additional gapmers were designed based on ISIS 409826 that demonstrated significant inhibition of PTP1B in all cell lines tested. These gapmers were designed by creating gapmers shifted slightly upstream and downstream (i.e. "microwalk") of ISIS 409826. Oligonucleotides were also created with various motifs, e.g. 5-10-5 MOE, 5-8-5 MOE, 2-13-5 MOE, 6-8-6 MOE motifs, or were uniform oligonucleotides with deoxy and MOE units. These gapmers were tested in vitro. ISIS oligonucleotides ISIS 142082, ISIS 113715, ISIS 373125, ISIS 404161, ISIS 404172, ISIS 404173, ISIS 404176, ISIS 409825, ISIS 409827, ISIS 409828, ISIS 409829, ISIS 409845, ISIS 409998, ISIS 409999, ISIS 410000, ISIS 410001, ISIS 410002, ISIS 410003, ISIS 410004, and ISIS 410030 (from Example 1), as well as ISIS 399038, ISIS 404159, and ISIS 404174, from a previous application (CORE0061WO15), were also included in the assay for comparison. Cultured HuVEC cells at a density of 20,000 cells per well were transfected using electroporation with 2,000 nM antisense oligonucleotide. After a treatment period of approximately 24 hours, RNA was isolated from the cells and PTP1B mRNA levels were measured by quantitative real-time PCR. The human primer probe set RTS3000 was used to measure PTP1B mRNA levels. PTP1B mRNA levels were adjusted according to total RNA content, as measured by RIBOGREEN®. Results are presented as percent inhibition of PTP1B mRNA, relative to untreated control cells. The results are presented in Tables 6 and 7.

The 5-10-5 MOE gapmers are 20 nucleotides in length, wherein the central gap segment is comprised of ten 2'-deoxynucleotides and is flanked on both sides (in the 5' and 3' directions) by wings comprising five nucleotides each. The 5-8-5 MOE gapmers are 18 nucleotides in length, wherein the central gap segment is comprised of eight 2'-deoxynucleotides and is flanked on both sides (in the 5' and 3' directions) by wings comprising five nucleotides each. The 2-13-5 MOE gapmers are 20 nucleotides in length, wherein the central gap segment is comprised of thirteen 2'-deoxynucleotides and is flanked on the 5' and the 3' directions with wings comprising two and five nucleotides respectively. The 6-8-6 MOE gapmers are 18 nucleotides in length, wherein the central gap segment is comprised of eight 2'-deoxynucleotides and is flanked on both sides (in the 5' and 3' directions) by wings comprising six nucleotides each. For each of the motifs (5-10-5, 5-8-5, 2-13-5, and 6-8-6), each nucleotide in the 5' wing segment and each nucleotide in the 3' wing segment has a 2'-MOE modification. The uniform oligonucleotides have deoxy and MOE units distributed throughout the length of the oligonucleotide. The symbols for the various unit chemistries in the uniform oligonucleotide sequences are as follows: 'd'=2'-deoxyribose; 'e'=2'-O-methoxyethyl ribose. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 6 is targeted SEQ ID NO: 1 (GENBANK Accession No. NM_002827.2). All the antisense oligonucleotides listed in Table 7 target SEQ ID NO: 2 (GENBANK Accession NT_011362.9 truncated from nucleotides 14178000 to 14256000).

As shown in Tables 6 and 7, several of the gapmers exhibited at least 50% inhibition, including ISIS numbers: 113715, 142082, 373125, 399038, 404159, 404161, 404172, 404173, 404176, 409826, 409827, 409999, 410000, 410001, 410002, 410003, 410004, 438371, 438372, 438373, 438374, 438375, 438377, 438379, 438380, 438381, 438382, 438383, 438384, 438439, 438442, 438443, 438444, 438445, 438450, 438451, 438452, 438453, 438454, 438455, 438456, 438458, 438459, 438460, 438461, 438462, 438464, 438465, 438468, 438469, 438472, 438473, and 438474.

Several of the gapmers exhibited at least 60% inhibition, including ISIS numbers: 113715, 142082, 373125, 399038, 404161, 404172, 404173, 404176, 409826, 409827, 409999, 410000, 410001, 410002, 410003, 438373, 438374, 438380, 438381, 438382, 438442, 438444, 438445, 438450, 438451, 438452, 438453, 438459, 438460, 438461, 438462, 438468, 438469, 438472, and 438474.

Several of the gapmers exhibited at least 70% inhibition, including ISIS numbers: 142082, 373125, 399038, 404161, 404172, 404173, 404176, 409826, 409827, 409999, 410000, 410001, 410002, 410003, 438373, 438374, 438444, 438451, 438452, 438453, 438460, 438461, 438462, 438468, 438469, 438472, and 438474.

Several of the gapmers exhibited at least 80% inhibition, including ISIS numbers: 142082, 404161, 404173, 404176, 409826, 410000, 410001, 410002, 410003, 438451, 438452, 438460, 438461, and 438474.

Several of the gapmers exhibited at least 85% inhibition, including ISIS numbers: 142082, 404161, 404173, 404176, 409826, 410001, 410002, and 410003.

Several of the gapmers exhibited at least 90% inhibition, including ISIS numbers: 142082, 404161, and 409826.

TABLE 6

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 989 | 1008 | 373125 | GGCACCTTCGATCACAGCCA | 5-10-5 MOE | 72 | 9 |
| 1035 | 1054 | 113715 | GCTCCTTCCACTGATCCTGC | 5-10-5 MOE | 68 | 10 |
| 2366 | 2385 | 404176 | TGATCAGGTCATGCACAGGC | 5-10-5 MOE | 89 | 14 |
| 3283 | 3302 | 409845 | TATTCCATGGCCATTGTAAA | 5-10-5 MOE | 32 | 19 |
| 3284 | 3303 | 303174 | TTATTCCATGGCCATTGTAA | 5-10-5 MOE | 47 | 20 |
| 3284 | 3303 | 410030 | TTATTCCATGGCCATTGTAA | 2-13-5 MOE | 47 | 20 |
| 3284 | 3303 | 438377 | $T_eT_dA_dT_dT_dC_eC_dA_dT_dG_dG_dC_dC_dA_dT_dT_dG_dT_dA_eA_e$ | Deoxy and MOE units | 52 | 20 |
| 3284 | 3303 | 438439 | $T_eT_dA_dT_dT_dC_dC_dT_dG_eG_eC_dC_dA_dT_dT_dG_dT_dA_eA_e$ | Deoxy and MOE units | 53 | 20 |
| 3284 | 3303 | 438448 | $T_eT_dA_eT_dT_dC_eC_dA_dT_dG_dG_dC_dC_dA_dT_dT_dG_dT_dA_eA_e$ | Deoxy and MOE units | 34 | 20 |
| 3284 | 3303 | 438457 | $T_eT_dA_eT_dT_dC_dC_dA_eT_dG_dG_dC_dC_dA_dT_dT_dG_dT_dA_eA_e$ | Deoxy and MOE units | 35 | 20 |
| 3284 | 3303 | 438466 | TTATTCCATGGCCATTGTAA | 6-8-6 MOE | 25 | 20 |
| 3285 | 3304 | 409825 | TTTATTCCATGGCCATTGTA | 5-10-5 MOE | 47 | 21 |
| 3285 | 3304 | 409998 | TTTATTCCATGGCCATTGTA | 2-13-5 MOE | 49 | 21 |
| 3285 | 3302 | 438368 | TATTCCATGGCCATTGTA | 5-8-5 MOE | 32 | 39 |
| 3285 | 3304 | 438378 | $T_eT_eT_dA_dT_dT_dC_eC_dA_dT_dG_dG_dC_dC_dA_dT_dT_dG_dT_eA_e$ | Deoxy and MOE units | 46 | 21 |
| 3285 | 3304 | 438440 | $T_eT_eT_dA_dT_dT_dC_dC_dA_dT_eG_eG_dC_dC_dA_dT_dT_dG_dT_eA_e$ | Deoxy and MOE units | 30 | 21 |
| 3285 | 3304 | 438449 | $T_eT_eT_dA_dT_dT_dC_eC_dA_dT_dG_dG_dC_dC_dA_dT_dT_dG_eT_eA_e$ | Deoxy and MOE units | 43 | 21 |
| 3285 | 3304 | 438458 | $T_eT_eT_dA_dT_dT_dC_dC_dA_eT_dG_dG_dC_dC_dA_dT_dT_dG_eT_eA_e$ | Deoxy and MOE units | 53 | 21 |
| 3285 | 3304 | 438467 | TTTATTCCATGGCCATTGTA | 6-8-6 MOE | 33 | 21 |
| 3286 | 3305 | 399038 | GTTTATTCCATGGCCATTGT | 5-10-5 MOE | 74 | 22 |
| 3286 | 3305 | 404159 | GTTTATTCCATGGCCATTGT | 2-13-5 MOE | 54 | 22 |
| 3286 | 3303 | 438369 | TTATTCCATGGCCATTGT | 5-8-5 MOE | 33 | 40 |
| 3286 | 3305 | 438379 | $G_eT_eT_dT_dA_dT_eT_dC_eC_dA_dT_dG_dG_dC_dC_dA_dT_dG_eT_e$ | Deoxy and MOE units | 51 | 22 |
| 3286 | 3305 | 438441 | $G_eT_eT_dT_dA_dT_dT_dC_dC_dA_eT_eG_dG_dC_dC_dA_dT_dG_eT_e$ | Deoxy and MOE units | 40 | 22 |
| 3286 | 3305 | 438450 | $G_eT_eT_eT_dA_dT_eT_dC_dC_dA_dT_dG_dG_dC_dC_dA_dT_eG_eT_e$ | Deoxy and MOE units | 64 | 22 |

TABLE 6-continued

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 3286 | 3305 | 438459 | $G_eT_eT_dA_dT_dT_dC_eC_eA_dT_dG_dG_dC_dC_dA_dT_dT_eG_eT_e$ | Deoxy and MOE units | 68 | 22 |
| 3286 | 3305 | 438468 | GTTTATTCCATGGCCATTGT | 6-8-6 MOE | 76 | 22 |
| 3287 | 3306 | 409826 | GGTTTATTCCATGGCCATTG | 5-10-5 MOE | 93 | 23 |
| 3287 | 3306 | 409999 | GGTTTATTCCATGGCCATTG | 2-13-5 MOE | 75 | 23 |
| 3287 | 3304 | 438370 | TTTATTCCATGGCCATTG | 5-8-5 MOE | 33 | 41 |
| 3287 | 3306 | 438380 | $G_eG_eT_dT_dA_eT_dT_dC_dC_dA_dT_dG_dG_dC_dC_dA_dT_eG_e$ | Dexoy and MOE units | 63 | 23 |
| 3287 | 3306 | 438442 | $G_eG_eT_dT_dA_dT_dT_dC_dC_eA_eT_dG_dG_dC_dC_dA_dT_eG_e$ | Deoxy and MOE units | 67 | 23 |
| 3287 | 3306 | 438451 | $G_eG_eT_dT_dA_eT_dT_dC_dC_dA_dT_dG_dG_dC_dC_dA_dT_eT_eG_e$ | Deoxy and MOE units | 83 | 23 |
| 3287 | 3306 | 438460 | $G_eG_eT_eT_dT_dA_dT_dT_eC_eC_dA_dT_dG_dG_dC_dC_dA_dT_eT_eG_e$ | Deoxy and MOE units | 82 | 23 |
| 3287 | 3306 | 438469 | GGTTTATTCCATGGCCATTG | 6-8-6 MOE | 71 | 23 |
| 3288 | 3307 | 404172 | TGGTTTATTCCATGGCCATT | 5-10-5 MOE | 76 | 24 |
| 3288 | 3307 | 410000 | TGGTTTATTCCATGGCCATT | 2-13-5 MOE | 83 | 24 |
| 3288 | 3305 | 438371 | GTTTATTCCATGGCCATT | 5-8-5 MOE | 54 | 42 |
| 3288 | 3307 | 438381 | $T_eG_eG_dT_dT_dA_eT_dT_dC_dC_dA_dT_dG_dG_dC_dC_dAT_eT_e$ | Deoxy and MOE units | 69 | 24 |
| 3288 | 3307 | 438443 | $T_eG_eG_dT_dT_dA_dT_dT_dC_eC_eA_dT_dG_dG_dC_dC_dA_dT_eT_e$ | Deoxy and MOE units | 50 | 24 |
| 3288 | 3307 | 438452 | $T_eG_eG_eT_dT_dT_eA_eT_dT_dC_dC_dA_dT_dG_dG_dC_dC_dA_eT_eT_e$ | Deoxy and MOE units | 82 | 24 |
| 3288 | 3307 | 438461 | $T_eG_eG_eT_dT_dA_dT_eT_eC_dC_dA_dT_dG_dG_dC_dC_dA_eT_eT_e$ | Deoxy and MOE units | 81 | 24 |
| 3288 | 3307 | 438470 | TGGTTTATTCCATGGCCATT | 6-8-6 MOE | 46 | 24 |
| 3289 | 3308 | 409827 | ATGGTTTATTCCATGGCCAT | 5-10-6 MOE | 74 | 25 |
| 3289 | 3308 | 410001 | ATGGTTTATTCCATGGCCAT | 2-13-5 MOE | 85 | 25 |
| 3289 | 3306 | 438372 | GGTTTATTCCATGGCCAT | 5-8-5 MOE | 52 | 43 |
| 3289 | 3308 | 438382 | $A_eT_eG_eG_dT_dT_eT_dA_dT_dC_dC_dA_dT_dG_dG_dC_dC_dA_eT_e$ | Deoxy and MOE units | 65 | 25 |
| 3289 | 3308 | 438444 | $A_eT_eG_eG_dT_dT_dA_dT_dT_eC_eC_dA_dT_dG_dG_dC_dC_dA_eT_e$ | Deoxy and MOE units | 72 | 25 |
| 3289 | 3308 | 438453 | $A_eT_eG_eG_dT_dT_eT_dA_dT_dC_dC_dA_dT_dG_dG_dC_dC_eA_eT_e$ | Deoxy and MOE units | 72 | 25 |
| 3289 | 3308 | 438462 | $A_eT_eG_eG_dT_dT_dT_dA_eT_dC_dC_dA_dT_dG_dG_dC_dC_eA_eT_e$ | Deoxy and MOE units | 70 | 25 |
| 3289 | 3308 | 438471 | ATGGTTTATTCCATGGCCAT | 6-8-6 MOE | 45 | 25 |
| 3290 | 3309 | 404173 | AATGGTTTATTCCATGGCCA | 5-10-5 MOE | 85 | 26 |
| 3290 | 3309 | 410002 | AATGGTTTATTCCATGGCCA | 2-13-5 MOE | 85 | 26 |
| 3290 | 3307 | 438373 | TGGTTTATTCCATGGCCA | 5-8-5 MOE | 70 | 44 |
| 3290 | 3309 | 438383 | $A_eA_eT_dG_dG_dT_eT_eT_dA_dT_dT_dC_dC_dA_dT_dG_dG_dC_dC_eA_e$ | Deoxy and MOE units | 54 | 26 |

TABLE 6-continued

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 3290 | 3309 | 438445 | $A_eA_eT_dG_dG_dT_dT_dT_dA_dT_eT_eC_dC_dA_dT_dG_dG_dC_dC_eA_e$ | Deoxy and MOE units | 66 | 26 |
| 3290 | 3309 | 438454 | $A_eA_eT_eG_dG_dT_eT_eT_dA_dT_dT_dC_dC_dA_dT_dG_dG_dC_eC_eA_e$ | Deoxy and MOE units | 52 | 26 |
| 3290 | 3309 | 438463 | $A_eA_eT_eG_dG_dT_dT_dT_dA_eT_dT_dC_dC_dA_dT_dG_dG_dC_eC_eA_e$ | Deoxy and MOE units | 39 | 26 |
| 3290 | 3309 | 438472 | AATGGTTTATTCCATGGCCA | 6-8-6 MOE | 73 | 26 |
| 3291 | 3310 | 142082 | AAATGGTTTATTCCATGGCC | 5-10-5 MOE | 90 | 27 |
| 3291 | 3310 | 410003 | AAATGGTTTATTCCATGGCC | 2-13-5 MOE | 86 | 27 |
| 3291 | 3308 | 438374 | ATGGTTTATTCCATGGCC | 5-8-5 MOE | 79 | 45 |
| 3291 | 3310 | 438384 | $A_eA_eA_dT_dG_dG_eT_eT_dA_dT_dT_dC_dC_dA_dT_dG_dG_dC_eC_e$ | Deoxy and MOE units | 53 | 27 |
| 3291 | 3310 | 438446 | $A_eA_eA_dT_dG_dG_dT_dT_dA_eT_eT_dC_dC_dA_dT_dG_dG_dC_eC_e$ | Deoxy and MOE units | 38 | 27 |
| 3291 | 3310 | 438455 | $A_eA_eA_eT_dG_dG_eT_eT_dA_dT_dT_dC_dC_dA_dT_dG_dG_eC_eC_e$ | Deoxy and MOE units | 58 | 27 |
| 3291 | 3310 | 438464 | $A_eA_eA_eT_dG_dG_dT_eT_eA_dT_dT_dC_dC_dA_dT_dG_dG_dC_eC_e$ | Deoxy and MOE units | 58 | 27 |
| 3291 | 3310 | 438473 | AAATGGTTTATTCCATGGCC | 6-8-6 MOE | 57 | 27 |
| 3292 | 3311 | 409828 | AAAATGGTTTATTCCATGGC | 5-10-5 MOE | 43 | 28 |
| 3292 | 3311 | 410004 | AAAATGGTTTATTCCATGGC | 2-13-5 MOE | 58 | 28 |
| 3292 | 3309 | 438375 | AATGGTTTATTCCATGGC | 5-8-5 MOE | 55 | 46 |
| 3292 | 3311 | 438385 | $A_eA_eA_eA_dT_dG_eG_eT_dT_dA_dT_dC_dC_dA_dT_dG_dG_eC_e$ | Deoxy and MOE units | 36 | 28 |
| 3292 | 3311 | 438447 | $A_eA_eA_eA_dT_dG_dG_dT_dT_eA_dT_dC_dC_dA_dT_dG_dG_eC_e$ | Deoxy and MOE units | 35 | 28 |
| 3292 | 3311 | 438456 | $A_eA_eA_eA_dT_dG_eG_eT_dT_dA_dT_dT_dC_dC_dA_dT_dG_eG_eC_e$ | Deoxy and MOE units | 58 | 28 |
| 3292 | 3311 | 438465 | $A_eA_eA_eA_dT_dG_dGT_eT_dA_dT_dT_dC_dC_dA_dT_dG_eG_eC_e$ | Deoxy and MOE units | 51 | 28 |
| 3292 | 3311 | 438474 | AAAATGGTTTATTCCATGGC | 6-8-6 MOE | 82 | 28 |
| 3293 | 3312 | 409829 | AAAAATGGTTTATTCCATGG | 5-10-5 MOE | 42 | 29 |
| 3293 | 3310 | 438376 | AAATGGTTTATTCCATGG | 5-8-5 MOE | 36 | 47 |

TABLE 7

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 70726 | 70745 | 373125 | GGCACCTTCGATCACAGCCA | 5-10-5 MOE | 72 | 9 |
| 73855 | 73874 | 404161 | GGTCATTTCCATGGCCAGAG | 2-13-5 MOE | 93 | 31 |
| 75045 | 75064 | 404176 | TGATCAGGTCATGCACAGGC | 5-10-5 MOE | 89 | 14 |
| 75962 | 75981 | 409845 | TATTCCATGGCCATTGTAAA | 5-10-5 MOE | 32 | 19 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75963 | 75982 | 404174 | TTATTCCATGGCCATTGTAA | 5-10-5 MOE | 47 | 20 |
| 75963 | 75982 | 410030 | TTATTCCATGGCCATTGTAA | 2-13-5 MOE | 47 | 20 |
| 75963 | 75982 | 438377 | $T_eT_eA_dT_dC_eC_eA_dT_dG_dG_dC_dC_dA_dT_dT_dG_dT_dA_eA_e$ | Deoxy and MOE units | 52 | 20 |
| 75963 | 75982 | 438439 | $T_eT_eA_dT_dC_dC_dA_dT_dG_eG_eC_dC_dA_dT_dT_dG_dT_dA_eA_e$ | Deoxy and MOE units | 53 | 20 |
| 75963 | 75982 | 438448 | $T_eT_eA_eT_dC_eC_eA_dT_dG_dG_dC_dC_dA_dT_dT_dG_dT_dA_eA_e$ | Deoxy and MOE units | 34 | 20 |
| 75963 | 75982 | 438457 | $T_eT_eA_eT_dC_dC_dA_eT_eG_dG_dC_dC_dA_dT_dT_dG_dT_dA_eA_e$ | Deoxy and MOE units | 35 | 20 |
| 75963 | 75982 | 438466 | TTATTCCATGGCCATTGTAA | 6-8-6 MOE | 25 | 20 |
| 75964 | 75983 | 409825 | TTTATTCCATGGCCATTGTA | 5-10-5 MOE | 47 | 21 |
| 75964 | 75983 | 409998 | TTTATTCCATGGCCATTGTA | 2-13-5 MOE | 49 | 21 |
| 75964 | 75981 | 438368 | TATTCCATGGCCATTGTA | 5-8-5 MOE | 32 | 39 |
| 75964 | 75983 | 438378 | $T_eT_eT_dA_dT_dT_eC_eC_dA_dT_dG_dG_dC_dC_dA_dT_dT_dG_dT_dA_e$ | Deoxy and MOE units | 46 | 21 |
| 75964 | 75983 | 438440 | $T_eT_eT_dA_dT_dT_dC_dC_dA_dT_eG_eG_eC_dC_dA_dT_dT_dG_dT_eA_e$ | Deoxy and MOE units | 30 | 21 |
| 75964 | 75983 | 438449 | $T_eT_eT_dA_dT_dT_eC_eC_dA_dT_dG_dG_dC_dC_dA_dT_dT_dG_eT_eA_e$ | Deoxy and MOE units | 43 | 21 |
| 75964 | 75983 | 438458 | $T_eT_eT_dA_dT_dT_dC_dC_dA_eT_dG_dG_dC_dC_dA_dT_dT_dG_eT_eA_e$ | Deoxy and MOE units | 53 | 21 |
| 75964 | 75983 | 438467 | TTTATTCCATGGCCATTGTA | 6-8-6 MOE | 33 | 21 |
| 75965 | 75984 | 399038 | GTTTATTCCATGGCCATTGT | 5-10-5 MOE | 74 | 22 |
| 75965 | 75984 | 404159 | GTTTATTCCATGGCCATTGT | 2-13-5 MOE | 54 | 22 |
| 75965 | 75982 | 438369 | TTATTCCATGGCCATTGT | 5-8-5 MOE | 33 | 40 |
| 75965 | 75984 | 438379 | $G_eT_eT_dT_dA_dT_eT_eC_dC_dA_dT_dG_dG_dC_dC_dA_dT_dT_dG_eT_e$ | Deoxy and MOE units | 51 | 22 |
| 75965 | 75984 | 438441 | $G_eT_eT_dT_dA_dT_dT_dC_dC_dA_eT_eG_dG_dC_dC_dA_dT_dT_dG_eT_e$ | Deoxy and MOE units | 40 | 22 |
| 75965 | 75984 | 438450 | $G_eT_eT_eT_dA_dT_eT_eC_dC_dA_dT_dG_dG_dC_dC_dA_dT_eG_eT_e$ | Deoxy and MOE units | 64 | 22 |
| 75965 | 75984 | 438459 | $G_eT_eT_eT_dA_dT_dT_dC_eC_dA_dT_dG_dG_dC_dC_dA_dT_eG_eT_e$ | Deoxy and MOE units | 68 | 22 |
| 75965 | 75984 | 438468 | GTTTATTCCATGGCCATTGT | 6-8-6 MOE | 76 | 22 |
| 75966 | 75985 | 409826 | GGTTTATTCCATGGCCATTG | 5-10-5 MOE | 93 | 23 |
| 75966 | 75985 | 409999 | GGTTTATTCCATGGCCATTG | 2-13-5 MOE | 75 | 23 |
| 75966 | 75983 | 438370 | TTTATTCCATGGCCATTG | 5-8-5 MOE | 33 | 41 |
| 75966 | 75985 | 438380 | $G_eG_eT_dT_dA_eT_eC_dC_dA_dT_dG_dG_dC_dC_dA_dT_eG_e$ | Deoxy and MOE units | 63 | 23 |
| 75966 | 75985 | 438442 | $G_eG_eT_dT_dA_dT_dT_dC_dC_dA_eT_dG_dG_dC_dC_dA_dT_eG_e$ | Deoxy and MOE units | 67 | 23 |
| 75966 | 75985 | 438451 | $G_eG_eT_eT_dT_dA_eT_eC_dC_dA_dT_dG_dG_dC_dC_dA_dT_eT_eG_e$ | Deoxy and MOE units | 83 | 23 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75966 | 75985 | 438460 | $G_eG_eT_eT_dA_dT_dT_eC_eC_dA_dT_dG_dG_dC_dC_dA_dT_eT_eG_e$ | Deoxy and MOE units | 82 | 23 |
| 75966 | 75985 | 438469 | GGTTTATTCCATGGCCATTG | 6-8-6 MOE | 71 | 23 |
| 75967 | 75986 | 404172 | TGGTTTATTCCATGGCCATT | 5-10-5 MOE | 76 | 24 |
| 75967 | 75986 | 410000 | TGGTTTATTCCATGGCCATT | 2-13-5 MOE | 83 | 24 |
| 75967 | 75984 | 438371 | GTTTATTCCATGGCCATT | 5-8-5 MOE | 54 | 42 |
| 75967 | 75986 | 438381 | $T_eG_eG_dT_dT_dT_eA_eT_dT_dC_dC_dA_dT_dG_dG_dC_dC_dAT_eT_e$ | Deoxy and MOE units | 69 | 24 |
| 75967 | 75986 | 438443 | $T_eG_eG_dT_dT_dT_dA_dT_dT_dC_eC_eA_dT_dG_dG_dC_dC_dA_dT_eT_e$ | Deoxy and MOE units | 50 | 24 |
| 75967 | 75986 | 438452 | $T_eG_eG_eT_dT_dT_eA_eT_dT_dC_dC_dA_dT_dG_dG_dC_dC_dA_eT_eT_e$ | Deoxy and MOE units | 82 | 24 |
| 75967 | 75986 | 438461 | $T_eG_eG_eT_dT_dT_dA_dT_eT_eC_dC_dA_dT_dG_dG_dC_dC_dA_eT_eT_e$ | Deoxy and MOE units | 81 | 24 |
| 75967 | 75986 | 438470 | TGGTTTATTCCATGGCCATT | 6-8-6 MOE | 46 | 24 |
| 75968 | 75987 | 409827 | ATGGTTTATTCCATGGCCAT | 5-10-5 MOE | 74 | 25 |
| 75968 | 75987 | 410001 | ATGGTTTATTCCATGGCCAT | 2-13-5 MOE | 85 | 25 |
| 75968 | 75985 | 438372 | GGTTTATTCCATGGCCAT | 5-8-5 MOE | 52 | 43 |
| 75968 | 75987 | 438382 | $A_eT_eG_dG_dT_dT_eT_eA_dT_dT_dC_dC_dA_dT_dG_dG_dC_dC_dA_eT_e$ | Deoxy and MOE units | 65 | 25 |
| 75968 | 75987 | 438444 | $A_eT_eG_dG_dT_dT_dA_dT_dT_eC_eC_dA_dT_dG_dG_dC_dC_dA_eT_e$ | Deoxy and MOE units | 72 | 25 |
| 75968 | 75987 | 438453 | $A_eT_eG_eG_dT_dT_eT_eA_dT_dT_dC_dC_dA_dT_dG_dG_dC_dC_dA_eT_e$ | Deoxy and MOE units | 72 | 25 |
| 75968 | 75987 | 438462 | $A_eT_eG_eG_dT_dT_dA_eT_eT_eC_dC_dA_dT_dG_dG_dC_dC_dA_eT_e$ | Deoxy and MOE units | 70 | 25 |
| 75968 | 75987 | 438471 | ATGGTTTATTCCATGGCCAT | 6-8-6 MOE | 45 | 25 |
| 75969 | 75988 | 404173 | AATGGTTTATTCCATGGCCA | 5-10-5 MOE | 85 | 26 |
| 75969 | 75988 | 410002 | AATGGTTTATTCCATGGCCA | 2-13-5 MOE | 85 | 26 |
| 75969 | 75986 | 438373 | TGGTTTATTCCATGGCCA | 5-8-5 MOE | 70 | 44 |
| 75969 | 75988 | 438383 | $A_eA_eT_dG_dG_dT_eT_eT_dA_dT_dT_dC_dC_dA_dT_dG_dG_dC_dC_eA_e$ | Deoxy and MOE units | 54 | 26 |
| 75969 | 75988 | 438445 | $A_eA_eT_dG_dG_dT_dT_dT_dA_dT_eT_eC_dC_dA_dT_dG_dG_dC_dC_eA_e$ | Deoxy and MOE units | 66 | 26 |
| 75969 | 75988 | 438454 | $A_eA_eT_eG_dG_dT_eT_eT_dA_dT_dT_dC_dC_dA_dT_dG_dG_dC_eC_eA_e$ | Deoxy and MOE units | 52 | 26 |
| 75969 | 75988 | 438463 | $A_eA_eT_eG_dG_dT_dT_dT_eA_eT_dT_dC_dC_dA_dT_dG_dG_dC_eC_eA_e$ | Deoxy and MOE units | 39 | 26 |
| 75969 | 75988 | 438472 | AATGGTTTATTCCATGGCCA | 6-8-6 MOE | 73 | 26 |
| 75970 | 75989 | 142082 | AAATGGTTTATTCCATGGCC | 5-10-5 MOE | 90 | 27 |
| 75970 | 75989 | 410003 | AAATGGTTTATTCCATGGCC | 2-13-5 MOE | 86 | 27 |
| 75970 | 75987 | 438374 | ATGGTTTATTCCATGGCC | 5-8-5 MOE | 79 | 45 |
| 75970 | 75989 | 438384 | $A_eA_eA_dT_dG_dG_eT_dT_dT_dA_dT_dT_dC_dA_dT_dG_dG_dC_eC_e$ | Deoxy and MOE units | 53 | 27 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75970 | 75989 | 438446 | $A_eA_eA_dT_dG_dG_dT_dT_dT_dA_eT_eT_dC_dC_dA_dT_dG_dG_dC_eC_e$ | Deoxy and MOE units | 38 | 27 |
| 75970 | 75989 | 438455 | $A_eA_eA_eT_dG_dG_eT_eT_dT_dA_dT_dT_dC_dC_dA_dT_dG_dG_eC_eC_e$ | Deoxy and MOE units | 58 | 27 |
| 75970 | 75989 | 438464 | $A_eA_eA_eT_dG_dG_dT_dT_eT_eA_dT_dT_dC_dC_dA_dT_dG_dG_eC_eC_e$ | Deoxy and MOE units | 58 | 27 |
| 75970 | 75989 | 438473 | AAATGGTTTATTCCATGGCC | 6-8-6 MOE | 57 | 27 |
| 75971 | 75990 | 409828 | AAAATGGTTTATTCCATGGC | 5-10-5 MOE | 43 | 28 |
| 75971 | 75990 | 410004 | AAAATGGTTTATTCCATGGC | 2-13-5 MOE | 58 | 28 |
| 75971 | 75988 | 438375 | AATGGTTTATTCCATGGC | 5-8-5 MOE | 55 | 46 |
| 75971 | 75990 | 438385 | $A_eA_eA_dA_dT_dG_eG_eT_dT_dT_dA_dT_dT_dC_dC_dA_dT_dG_dG_eC_e$ | Deoxy and MOE units | 36 | 28 |
| 75971 | 75990 | 438447 | $A_eA_eA_dA_dT_dG_dG_dT_dT_eA_eT_dT_dC_dC_dA_dT_dG_dG_eC_e$ | Deoxy and MOE units | 35 | 28 |
| 75971 | 75990 | 438456 | $A_eA_eA_eA_dT_dG_eG_eT_dT_dA_dT_dT_dC_dC_dA_dT_dG_eG_eC_e$ | Deoxy and MOE units | 58 | 28 |
| 75971 | 75990 | 438465 | $A_eA_eA_eA_dT_dG_dGT_eT_eT_dA_dT_dT_dC_dC_dA_dT_dG_eG_eC_e$ | Deoxy and MOE units | 51 | 28 |
| 75971 | 75990 | 438474 | AAAATGGTTTATTCCATGGC | 6-8-6 MOE | 82 | 28 |
| 75972 | 75991 | 409829 | AAAAATGGTTTATTCCATGG | 5-10-5 MOE | 42 | 29 |
| 75972 | 75989 | 438376 | AAATGGTTTATTCCATGG | 5-8-5 MOE | 36 | 47 |

Example 6

Dose-Dependent Antisense Inhibition of Human PTP1B mRNA in HuVEC Cells

Several antisense oligonucleotides, which displayed significant antisense inhibition of PTP1B mRNA in the study described in Example 5 were further tested in HuVEC cells at various doses. Cells were plated at a density of 2,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 8 as percent inhibition of PTP1B mRNA, relative to untreated control cells.

TABLE 8

Dose-dependent antisense inhibition of human PTP1B in HuVEC cells

| ISIS No | 31.25 nM | 62.5 nM | 125.0 nM | 250.0 nM | 500.0 nM | 1000.0 nM | 2000.0 nM | 4000.0 nM | $IC_{50}$ (µM) |
|---|---|---|---|---|---|---|---|---|---|
| 142082 | 15 | 30 | 40 | 42 | 71 | 84 | 90 | 94 | 0.2 |
| 404173 | 15 | 19 | 33 | 54 | 69 | 81 | 86 | 93 | 0.2 |
| 404176 | 9 | 26 | 34 | 34 | 67 | 80 | 88 | 94 | 0.3 |
| 409826 | 17 | 16 | 28 | 44 | 60 | 73 | 85 | 95 | 0.3 |
| 410002 | 0 | 0 | 24 | 52 | 54 | 77 | 90 | 96 | 0.4 |
| 410003 | 9 | 7 | 19 | 46 | 60 | 80 | 91 | 95 | 0.4 |
| 438374 | 20 | 22 | 40 | 44 | 59 | 70 | 79 | 85 | 0.3 |
| 438460 | 14 | 21 | 23 | 42 | 62 | 78 | 85 | 95 | 0.3 |
| 438474 | 27 | 0 | 13 | 34 | 42 | 68 | 74 | 86 | 0.6 |

Example 7

Dose-Dependent Antisense Inhibition of Human mRNA PTP1B in HepG2 Cells

The antisense oligonucleotides, tested in the study described in Example 6, were further tested in HepG2 cells at various doses. Cells were plated at a density of 20,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 9 as percent inhibition of PTP1B mRNA, relative to untreated control cells. The mRNA levels were also analyzed using rhesus monkey primer probe set RTS198, and the results are presented in Table 10. The start and stop sites of each oligonucleotide on rhesus monkey SEQ ID NO: 3 are presented in Table 11.

Example 8

Dose-Dependent Antisense Inhibition of Human PTP1B mRNA in HepG2 Cells

Short antisense oligonucleotides to the target site of ISIS 142082 were designed. The target sites, motifs and sequence details of these shortmers are presented in Table 12. These antisense oligonucleotides were tested in HepG2 cells at various doses. Some of the antisense oligonucleotides from the study described in Example 7 were included in the assay for comparison. Cells were plated at a density of 20,000 cells per well and transfected by electroporation with 78.125 nM, 156.25 nM, 312.5 nM, 625 nM, 1,250 nM, 2,500 nM, 5,000

TABLE 9

Analysis of dose-dependent antisense inhibition of human PTP1B in HepG2 cells using RTS3000

| ISIS No | 31.25 nM | 62.5 nM | 125.0 nM | 250.0 nM | 500.0 nM | 1000.0 nM | 2000.0 nM | 4000.0 nM | IC$_{50}$ (μM) |
|---|---|---|---|---|---|---|---|---|---|
| 142082 | 0 | 0 | 7 | 0 | 26 | 38 | 60 | 82 | 1.4 |
| 404173 | 2 | 0 | 1 | 19 | 0 | 29 | 47 | 80 | 1.9 |
| 404176 | 0 | 0 | 5 | 13 | 2 | 33 | 62 | 79 | 1.7 |
| 409826 | 0 | 0 | 0 | 2 | 15 | 29 | 46 | 76 | 1.9 |
| 410002 | 13 | 6 | 0 | 11 | 8 | 28 | 44 | 75 | 2.0 |
| 410003 | 0 | 0 | 9 | 11 | 22 | 33 | 30 | 83 | 1.9 |
| 438374 | 0 | 0 | 17 | 11 | 23 | 38 | 33 | 61 | 2.9 |
| 438460 | 4 | 0 | 10 | 11 | 9 | 26 | 52 | 79 | 1.8 |
| 438474 | 0 | 0 | 2 | 11 | 6 | 20 | 52 | 54 | 2.8 |

TABLE 10

Analysis of dose-dependent antisense inhibition of human PTP1B in HepG2 cells using RTS198

| ISIS No | 31.25 nM | 62.5 nM | 125.0 nM | 250.0 nM | 500.0 nM | 1000.0 nM | 2000.0 nM | 4000.0 nM | IC$_{50}$ (μM) |
|---|---|---|---|---|---|---|---|---|---|
| 142082 | 14 | 19 | 2 | 0 | 80 | 41 | 63 | 80 | 1.5 |
| 404173 | 0 | 0 | 2 | 0 | 16 | 26 | 60 | 83 | 1.6 |
| 404176 | 0 | 0 | 0 | 5 | 0 | 31 | 59 | 80 | 1.9 |
| 409826 | 0 | 0 | 0 | 16 | 23 | 10 | 49 | 72 | 2.3 |
| 410002 | 0 | 0 | 0 | 0 | 0 | 0 | 40 | 100 | >4.0 |
| 410003 | 0 | 1 | 12 | 0 | 10 | 41 | 51 | 82 | 1.6 |
| 438374 | 0 | 0 | 0 | 9 | 43 | 22 | 49 | 55 | 2.8 |
| 438460 | 0 | 0 | 0 | 9 | 30 | 42 | 47 | 81 | 1.4 |
| 438474 | 2 | 0 | 9 | 38 | 19 | 31 | 49 | 60 | 2.5 |

TABLE 11

Target sites of antisense oligonucleotides targeting PTP1B on rhesus monkey gene sequence (SEQ ID NO: 3)

| OligoID | Start Site | Stop Site | SEQ ID NO |
|---|---|---|---|
| 142082 | 4495 | 4514 | 27 |
| 404173 | 4494 | 4513 | 26 |
| 404176 | 3571 | 3590 | 14 |
| 409826 | 4491 | 4510 | 23 |
| 410002 | 4494 | 4513 | 26 |
| 410003 | 4495 | 4514 | 27 |
| 438374 | 4495 | 4512 | 45 |
| 438460 | 4491 | 4510 | 23 |
| 438474 | 4496 | 4515 | 28 | nM and 10,000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 13 as percent inhibition of PTP1B mRNA, relative to untreated control cells.

TABLE 12

Target sites of antisense oligonucleotides targeting SEQ ID NO: 1

| ISIS No | Start Site | Stop Site | Sequence | Motif | SEQ ID NO |
|---|---|---|---|---|---|
| 142082 | 3291 | 3310 | AAATGGTTTATTCCATGGCC | 5-10-5 | 27 |
| 446431 | 3292 | 3309 | AATGGTTTATTCCATGGC | 4-10-4 | 46 |
| 446432 | 3293 | 3308 | ATGGTTTATTCCATGG | 3-10-3 | 48 |

TABLE 13

Dose-dependent antisense inhibition of human PTP1B in HepG2 cells

| ISIS No | 78.125 nM | 156.25 nM | 312.5 nM | 625.0 nM | 1250.0 nM | 2500.0 nM | 5000.0 nM | 10000.0 nM | IC$_{50}$ (μM) |
|---|---|---|---|---|---|---|---|---|---|
| 113715 | 6 | 12 | 17 | 17 | 16 | 45 | 61 | 86 | 3.3 |
| 142082 | 14 | 34 | 23 | 47 | 60 | 81 | 86 | 90 | 0.8 |
| 404173 | 8 | 22 | 29 | 45 | 60 | 73 | 83 | 88 | 0.8 |
| 409826 | 19 | 18 | 41 | 56 | 75 | 84 | 89 | 91 | 0.5 |
| 410003 | 0 | 0 | 19 | 39 | 55 | 81 | 91 | 92 | 1.0 |
| 446431 | 10 | 24 | 26 | 38 | 57 | 74 | 85 | 92 | 1.0 |
| 446432 | 0 | 8 | 10 | 10 | 10 | 26 | 40 | 67 | 6.0 |

Example 9

Dose-Dependent Antisense Inhibition of PTP1B mRNA in LLC-MK2 Cells

The antisense oligonucleotides from the study described in Example 8 are also cross-reactive with rhesus monkey PTP1B gene sequence (SEQ ID NO: 3) and were further tested in rhesus monkey LLC-MK2 cells at various doses. Cells were plated at a density of 25,000 cells per well and transfected using electroporation with 78.125 nM, 156.25 nM, 312.5 nM, 625 nM, 1250 nM, 2500 nM, 5,000 nM, and 10,000 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 14 as percent inhibition of PTP1B mRNA, relative to untreated control cells. The start and stop sites of each oligonucleotide on rhesus monkey SEQ ID NO: 3 are presented in Table 15.

TABLE 14

Dose-dependent antisense inhibition of PTP1B mRNA in LLC-MK2 cells

| ISIS No | 78.125 nM | 156.25 nM | 312.5 nM | 625.0 nM | 1250.0 nM | 2500.0 nM | 5000.0 nM | 10000.0 nM | IC$_{50}$ (μM) |
|---|---|---|---|---|---|---|---|---|---|
| 113715 | 0 | 0 | 4 | 13 | 27 | 53 | 57 | 70 | 3.3 |
| 142082 | 2 | 12 | 31 | 41 | 69 | 74 | 80 | 92 | 0.9 |
| 404173 | 2 | 0 | 22 | 29 | 36 | 61 | 78 | 84 | 1.6 |
| 409826 | 12 | 0 | 19 | 38 | 66 | 66 | 82 | 92 | 1.2 |
| 410003 | 0 | 0 | 0 | 26 | 32 | 65 | 81 | 91 | 1.8 |
| 446431 | 0 | 0 | 9 | 32 | 45 | 70 | 79 | 58 | 1.4 |
| 446432 | 0 | 0 | 7 | 16 | 10 | 20 | 26 | 43 | 37.0 |

TABLE 15

Target sites of antisense oligonucleotides targeting SEQ ID NO: 3

| ISIS No | Start Site | Stop Site | Sequence | SEQ ID NO |
|---|---|---|---|---|
| 113715 | 1035 | 1054 | GCTCCTTCCACTGATCCTGC | 10 |
| 142082 | 4495 | 4514 | AAATGGTTTATTCCATGGCC | 27 |
| 404173 | 4494 | 4513 | AATGGTTTATTCCATGGCCA | 26 |
| 409826 | 4491 | 4510 | GGTTTATTCCATGGCCATTG | 23 |
| 410003 | 4495 | 4514 | AAATGGTTTATTCCATGGCC | 27 |
| 446431 | 4496 | 4513 | AATGGTTTATTCCATGGC | 46 |
| 446432 | 4497 | 4512 | ATGGTTTATTCCATGG | 48 |

Example 10

Dose-Dependent Antisense Inhibition of Human PTP1B mRNA in HuVEC Cells

The antisense oligonucleotides, tested in the study described in Examples 8 and 9, were further tested in HuVEC cells at various doses. Cells were plated at a density of 20,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 16 as percent inhibition of PTP1B mRNA, relative to untreated control cells.

TABLE 16

Dose-dependent antisense inhibition of human PTP1B in HuVEC cells

| ISIS No | 31.25 nM | 62.5 nM | 125.0 nM | 250.0 nM | 500.0 nM | 1000.0 nM | 2000.0 nM | 4000.0 nM | IC$_{50}$ (μM) |
|---|---|---|---|---|---|---|---|---|---|
| 113715 | 10 | 0 | 22 | 24 | 65 | 86 | 92 | 98 | 0.2 |
| 142082 | 52 | 78 | 89 | 93 | 95 | 96 | 98 | 98 | <0.3 |
| 404173 | 35 | 66 | 80 | 89 | 95 | 98 | 97 | 97 | 0.05 |
| 409826 | 57 | 72 | 82 | 64 | 97 | 98 | 98 | 98 | <0.3 |
| 410003 | 43 | 47 | 75 | 84 | 48 | 95 | 96 | 91 | 0.05 |
| 446431 | 33 | 63 | 75 | 87 | 96 | 97 | 98 | 98 | 0.05 |
| 446432 | 0 | 11 | 30 | 45 | 66 | 79 | 85 | 76 | 0.3 |

Example 11

Dose-Dependent Antisense Inhibition of PTP1B mRNA in Cynomolgus Primary Hepatocytes The antisense oligonucleotides from the study described in Examples 8-10 were further tested in cynomolgus primary hepatocytes at various doses. Cells were plated at a density of 35,000 cells per well and transfected using electroporation with 31.25 nM, 62.5 nM, 125 nM, 250 nM, 500 nM, 1,000 nM, 2,000 nM, and 4,000 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 17 as percent inhibition of PTP1B mRNA, relative to untreated control cells.

TABLE 17

Dose-dependent antisense inhibition of PTP1B mRNA in cynomolgus primary hepatocytes

| ISIS No | 31.25 nM | 62.5 nM | 125.0 nM | 250.0 nM | 500.0 nM | 1000.0 nM | 2000.0 nM | 4000.0 nM | IC$_{50}$ (μM) |
|---|---|---|---|---|---|---|---|---|---|
| 113715 | 4 | 26 | 25 | 43 | 46 | 73 | 82 | 95 | 0.4 |
| 142082 | 25 | 37 | 50 | 67 | 74 | 87 | 86 | 88 | 0.1 |
| 404173 | 18 | 20 | 43 | 54 | 67 | 82 | 85 | 89 | 0.2 |
| 409826 | 34 | 47 | 51 | 65 | 76 | 87 | 88 | 90 | 0.1 |
| 410003 | 8 | 20 | 44 | 53 | 68 | 79 | 80 | 83 | 0.2 |
| 446431 | 9 | 14 | 35 | 54 | 57 | 79 | 79 | 88 | 0.3 |
| 446432 | 4 | 0 | 1 | 3 | 0 | 11 | 6 | 37 | >4.0 |

Example 12

Tolerability of Antisense Oligonucleotides Targeting Human PTP1B in a Mouse Model ISIS oligonucleotides that demonstrated dose-dependent inhibition in the studies described in Examples 8-11 were evaluated for tolerability in a mouse model by monitoring changes in the levels of various metabolic markers in CD1 mice. Two more ISIS oligonucleotides, ISIS 446433 (4-10-4 MOE; 5'-GTTTATTCCATGGCCATT-3' (SEQ ID NO: 42); target start site at SEQ ID NO: 1 is 3288) and ISIS 446434 (3-10-3; 5'-TTTATTCCATGGCCAT-3' (SEQ ID NO: 49); target start site at SEQ ID NO: 1 is 3289) were designed as shortmers to ISIS 409826 (target start site at SEQ ID NO: 1 is 3287) and were also evaluated in this study.

Treatment

CD1 mice (available from Jackson Labs, Bar Harbor, Me.) were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of five CD1 mice each were injected subcutaneously twice a week with 100 mg/kg of ISIS 142082, ISIS 373125, ISIS 404173, ISIS 409826, ISIS 410002, ISIS 410003, ISIS 438452, ISIS 438460, ISIS 446431, ISIS 446432, ISIS 446433, or ISIS 446434 for 4 weeks. One group of five CD1 mice was injected subcutaneously twice a week with PBS for 4 weeks. This PBS group served as the control group. Blood samples were collected via tail snipping. Two days after the last dose, body weights were taken, mice were euthanized and organs and plasma were harvested for further analysis.

Body and Organ Weights

The body weights of the mice were measured weekly. The body weights are presented in Table 18. Liver, spleen and kidney weights were measured at the end of the study, and are presented in Table 19. The results demonstrate that none of the ISIS oligonucleotides had any adverse effect on the overall health of the mice.

TABLE 18

Weekly body weights of CD1 mice during antisense oligonucleotide treatment (g)

| | Week 1 | Week 2 | Week 3 | Week 4 |
|---|---|---|---|---|
| PBS | 29 | 31 | 32 | 34 |
| ISIS 142082 | 31 | 34 | 34 | 36 |
| ISIS 373125 | 29 | 31 | 32 | 35 |
| ISIS 404173 | 31 | 33 | 34 | 36 |
| ISIS 409826 | 31 | 34 | 34 | 37 |

TABLE 18-continued

Weekly body weights of CD1 mice during antisense oligonucleotide treatment (g)

|  | Week 1 | Week 2 | Week 3 | Week 4 |
|---|---|---|---|---|
| ISIS 410002 | 32 | 35 | 35 | 36 |
| ISIS 410003 | 31 | 34 | 34 | 37 |
| ISIS 438452 | 32 | 35 | 36 | 39 |
| ISIS 438460 | 31 | 34 | 34 | 37 |
| ISIS 446431 | 30 | 33 | 33 | 36 |
| ISIS 446432 | 27 | 30 | 30 | 33 |
| ISIS 446433 | 30 | 33 | 33 | 37 |
| ISIS 446434 | 30 | 33 | 34 | 37 |

TABLE 19

Organ weights of CD1 mice after antisense oligonucleotide treatment (g)

|  | Liver | Fat | Spleen | Kidney |
|---|---|---|---|---|
| PBS | 1.7 | 0.45 | 0.11 | 0.53 |
| ISIS 142082 | 2.3 | 0.33 | 0.18 | 0.52 |
| ISIS 373125 | 1.9 | 0.38 | 0.16 | 0.53 |
| ISIS 404173 | 2.3 | 0.41 | 0.23 | 0.59 |
| ISIS 409826 | 2.2 | 0.37 | 0.17 | 0.54 |
| ISIS 410002 | 1.9 | 0.22 | 0.30 | 0.76 |
| ISIS 410003 | 2.1 | 0.44 | 0.22 | 0.60 |
| ISIS 438452 | 2.2 | 0.42 | 0.18 | 0.55 |
| ISIS 438460 | 2.2 | 0.34 | 0.17 | 0.52 |
| ISIS 446431 | 2.1 | 0.34 | 0.19 | 0.53 |
| ISIS 446432 | 1.7 | 0.31 | 0.13 | 0.46 |
| ISIS 446433 | 2.2 | 0.35 | 0.17 | 0.53 |
| ISIS 446434 | 2.2 | 0.36 | 0.18 | 0.56 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured bi-weekly. The results are presented in Tables 20 and 21, and indicate that most of the ISIS oligonucleotides were considered tolerable in the mice, as demonstrated by their liver transaminase profile.

TABLE 20

Effect of antisense oligonucleotide treatment on ALT (IU/L) of CD1 mice

|  | Week 0 | Week 2 | Week 4 |
|---|---|---|---|
| PBS | 27 | 26 | 20 |
| ISIS 142082 | 38 | 35 | 105 |
| ISIS 373125 | 30 | 27 | 51 |
| ISIS 404173 | 30 | 31 | 124 |
| ISIS 409826 | 26 | 34 | 236 |
| ISIS 410002 | 27 | 203 | 219 |
| ISIS 410003 | 31 | 29 | 99 |
| ISIS 438452 | 32 | 40 | 217 |
| ISIS 438460 | 30 | 40 | 216 |
| ISIS 446431 | 29 | 38 | 114 |
| ISIS 446432 | 26 | 27 | 35 |
| ISIS 446433 | 25 | 76 | 115 |
| ISIS 446434 | 23 | 44 | 146 |

TABLE 21

Effect of antisense oligonucleotide treatment on AST (IU/L) of CD1 mice

|  | Week 0 | Week 2 | Week 4 |
|---|---|---|---|
| PBS | 54 | 62 | 50 |
| ISIS 142082 | 75 | 59 | 103 |
| ISIS 373125 | 55 | 57 | 97 |
| ISIS 404173 | 52 | 61 | 117 |
| ISIS 409826 | 49 | 59 | 192 |
| ISIS 410002 | 51 | 151 | 417 |
| ISIS 410003 | 64 | 47 | 122 |
| ISIS 438452 | 59 | 56 | 157 |
| ISIS 438460 | 65 | 56 | 217 |
| ISIS 446431 | 56 | 66 | 140 |
| ISIS 446432 | 50 | 51 | 74 |
| ISIS 446433 | 54 | 87 | 121 |
| ISIS 446434 | 42 | 64 | 132 |

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 22, expressed in mg/dL. None of the ISIS oligonucleotides had any adverse effects on the glucose metabolism of the mice.

TABLE 22

Effect of antisense oligonucleotide treatment on plasma glucose levels in CD1 mice

|  | Week 0 | Week 2 | Week 4 |
|---|---|---|---|
| PBS | 175 | 188 | 182 |
| ISIS 142082 | 195 | 178 | 161 |
| ISIS 373125 | 187 | 201 | 177 |
| ISIS 404173 | 185 | 213 | 168 |
| ISIS 409826 | 183 | 187 | 187 |
| ISIS 410002 | 183 | 164 | 137 |
| ISIS 410003 | 198 | 218 | 168 |
| ISIS 438452 | 168 | 197 | 175 |
| ISIS 438460 | 212 | 203 | 169 |
| ISIS 446431 | 192 | 188 | 148 |
| ISIS 446432 | 194 | 193 | 175 |
| ISIS 446433 | 216 | 198 | 151 |
| ISIS 446434 | 199 | 189 | 159 |

Plasma Lipid and Triglyceride Levels

To evaluate the effect of ISIS oligonucleotides on cholesterol and triglyceride metabolism, plasma levels of each were measured using an automated clinical chemistry analyzer (Hitachi Olympus AU400e, Melville, N.Y.). Results are presented in Tables 23 and 24, expressed in mg/dL. Most of the ISIS oligonucleotides did not have any adverse effects of the lipid metabolism of the mice.

TABLE 23

Effect of antisense oligonucleotide treatment on plasma cholesterol levels in CD1 mice

|  | Week 0 | Week 2 | Week 4 |
|---|---|---|---|
| PBS | 162 | 145 | 153 |
| ISIS 142082 | 156 | 136 | 126 |
| ISIS 373125 | 137 | 106 | 104 |
| ISIS 404173 | 162 | 124 | 154 |
| ISIS 409826 | 153 | 142 | 146 |
| ISIS 410002 | 136 | 63 | 47 |
| ISIS 410003 | 160 | 131 | 96 |
| ISIS 438452 | 143 | 128 | 121 |
| ISIS 438460 | 146 | 140 | 129 |

TABLE 23-continued

Effect of antisense oligonucleotide treatment
on plasma cholesterol levels in CD1 mice

|  | Week 0 | Week 2 | Week 4 |
| --- | --- | --- | --- |
| ISIS 446431 | 139 | 124 | 116 |
| ISIS 446432 | 146 | 135 | 137 |
| ISIS 446433 | 152 | 144 | 145 |
| ISIS 446434 | 147 | 147 | 144 |

TABLE 24

Effect of antisense oligonucleotide treatment
on plasma triglyceride levels in CD1 mice

|  | Week 0 | Week 2 | Week 4 |
| --- | --- | --- | --- |
| PBS | 153 | 153 | 162 |
| ISIS 142082 | 170 | 153 | 114 |
| ISIS 373125 | 142 | 116 | 112 |
| ISIS 404173 | 195 | 140 | 107 |
| ISIS 409826 | 182 | 120 | 80 |
| ISIS 410002 | 137 | 99 | 51 |
| ISIS 410003 | 152 | 138 | 102 |
| ISIS 438452 | 123 | 134 | 93 |
| ISIS 438460 | 165 | 146 | 85 |
| ISIS 446431 | 131 | 160 | 123 |
| ISIS 446432 | 168 | 194 | 136 |
| ISIS 446433 | 186 | 117 | 133 |
| ISIS 446434 | 145 | 101 | 84 |

Cytokine Levels

To evaluate the effect of ISIS oligonucleotides on factors involved in inflammation, blood was collected after the end of the treatment period for measurement of cytokine levels. The samples were sent to Aushon Biosystems (Woburn, Mass.) for analysis. Levels of murine IL-6, JE, MIP-1α, and TNF-α were measured using murine antibodies. The results are presented in Table 25. Most of the ISIS oligonucleotides did not have any adverse effects on the cytokine levels of the mice.

TABLE 25

Effect of antisense oligonucleotide treatment
on plasma cytokine levels in CD1 mice

|  | mIL-6 | mJE | mMIP-1α | mTNF-α |
| --- | --- | --- | --- | --- |
| PBS | 250 | 20 | 1 | 4 |
| ISIS 142082 | 225 | 145 | 4 | 23 |
| ISIS 373125 | 77 | 91 | 3 | 17 |
| ISIS 404173 | 88 | 155 | 1 | 24 |
| ISIS 409826 | 33 | 112 | 3 | 15 |
| ISIS 410002 | 113 | 225 | 28 | 84 |
| ISIS 410003 | 111 | 138 | 4 | 24 |
| ISIS 438452 | 62 | 148 | 1 | 15 |
| ISIS 438460 | 64 | 184 | 2 | 9 |
| ISIS 446431 | 52 | 170 | 1 | 15 |
| ISIS 446432 | 57 | 75 | 1 | 3 |
| ISIS 446433 | 64 | 138 | 3 | 61 |
| ISIS 446434 | 59 | 127 | 0 | 21 |

Example 13

Tolerability of Antisense Oligonucleotides Targeting Human PTP1B in a Rat Model

The ISIS oligonucleotides from the study described in Example 12 were further evaluated for tolerability in a rat model by monitoring changes in the levels of various metabolic markers in Sprague Dawley rats.

Treatment

Sprague Dawley rats were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of four rats each were injected subcutaneously twice a week with ISIS 142082, ISIS 373125, ISIS 404173, ISIS 409826, ISIS 410002, ISIS 410003, ISIS 438452, ISIS 438460, ISIS 446431, ISIS 446432, ISIS 446433, or ISIS 446434 at a dose of 50 mg/kg twice a week for 4 weeks, followed by a dose of 30 mg/kg twice a week for 8 weeks. One group of four rats was injected subcutaneously twice a week with PBS for 12 weeks. This PBS group served as the control group. Blood samples were collected via tail snipping. Two days after the last dose, body weights were taken, rats were euthanized and organs and plasma were harvested for further analysis.

Body and Organ Weights

The body weights of the rats were measured weekly. The body weights are presented in Table 26. Liver, spleen and kidney weights were measured at the end of the study, and are presented in Table 27. 'n/a' indicates no data being available for that particular group at that particular time point due to all the rats in the group being euthanized before the time point.

TABLE 26

Bi-weekly body weights of Sprague Dawley rats during
antisense oligonucleotide treatment (g)

|  | Week 0 | Week 2 | Week 4 | Week 6 | Week 8 | Week 10 | Week 12 |
| --- | --- | --- | --- | --- | --- | --- | --- |
| PBS | 288 | 369 | 405 | 442 | 463 | 500 | 495 |
| ISIS 142082 | 295 | 348 | 318 | 345 | 337 | 347 | 345 |
| ISIS 373125 | 304 | 385 | 399 | 419 | 427 | 421 | 448 |
| ISIS 404173 | 294 | 346 | 352 | 377 | 384 | 391 | 401 |
| ISIS 409826 | 292 | 346 | 350 | 355 | 356 | 373 | 356 |
| ISIS 410002 | 297 | 333 | 323 | 324 | 306 | 335 | n/a |
| ISIS 410003 | 299 | 341 | 328 | 320 | 307 | 305 | 301 |
| ISIS 438452 | 301 | 327 | 335 | 333 | 327 | 347 | 332 |
| ISIS 438460 | 304 | 345 | 346 | 347 | 356 | 377 | n/a |
| ISIS 446431 | 307 | 376 | 340 | 357 | 353 | 357 | 349 |
| ISIS 446432 | 287 | 340 | 344 | 363 | 372 | 399 | 404 |
| ISIS 446433 | 298 | 331 | 318 | 354 | n/a | n/a | n/a |
| ISIS 446434 | 303 | 366 | 356 | n/a | n/a | n/a | n/a |

TABLE 27

Organ weights of Sprague Dawley rats during
antisense oligonucleotide treatment (g)

|  | Liver | Fat | Spleen | Kidney |
| --- | --- | --- | --- | --- |
| PBS | 15.9 | 2.1 | 0.8 | 3.6 |
| ISIS 142082 | 21.8 | 0.7 | 4.5 | 5.2 |
| ISIS 373125 | 17.9 | 1.1 | 1.9 | 3.4 |
| ISIS 404173 | 17.7 | 1.1 | 2.3 | 4.3 |
| ISIS 409826 | 19.8 | 0.5 | 3.6 | 4.4 |
| ISIS 410003 | 18.7 | 0.5 | 3.8 | 3.5 |
| ISIS 438452 | 17.3 | 0.6 | 3.1 | 3.8 |
| ISIS 446431 | 22.1 | 0.4 | 6.1 | 5.3 |
| ISIS 446432 | 18.1 | 1.2 | 3.3 | 3.8 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured bi-weekly. Plasma levels of bilirubin (mg/dL) were also measured using the same clinical chemistry analyzer. The results are presented in Tables 28, 29 and 30. 'n/a' indicates no data being available for that particular group at that particular time point due to all the rats in the group being euthanized before the time point.

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in Tables 31 and 32, expressed in mg/dL. The total urine protein to creatinine ratio was also calculated and the results are presented in Table 33.

TABLE 28

Effect of antisense oligonucleotide treatment on ALT (IU/L) of Sprague Dawley rats

| | Week 0 | Week 2 | Week 4 | Week 6 | Week 8 | Week 10 | Week 12 |
|---|---|---|---|---|---|---|---|
| PBS | 58 | 68 | 54 | 48 | 48 | 46 | 46 |
| ISIS 142082 | 54 | 75 | 40 | 44 | 49 | 62 | 57 |
| ISIS 373125 | 57 | 61 | 60 | 48 | 48 | 45 | 38 |
| ISIS 404173 | 49 | 52 | 53 | 41 | 51 | 53 | 42 |
| ISIS 409826 | 51 | 59 | 56 | 50 | 42 | 37 | 40 |
| ISIS 410002 | 46 | 65 | 75 | 73 | 103 | 126 | n/a |
| ISIS 410003 | 49 | 78 | 62 | 49 | 61 | 59 | 66 |
| ISIS 438452 | 46 | 57 | 58 | 53 | 51 | 52 | 50 |
| ISIS 438460 | 49 | 88 | 162 | 96 | 114 | 91 | n/a |
| ISIS 446431 | 51 | 57 | 45 | 45 | 40 | 55 | 49 |
| ISIS 446432 | 52 | 59 | 48 | 43 | 44 | 49 | 46 |
| ISIS 446433 | 53 | 120 | 65 | 86 | n/a | n/a | n/a |
| ISIS 446434 | 53 | 76 | 161 | n/a | n/a | n/a | n/a |

TABLE 29

Effect of antisense oligonucleotide treatment on AST (IU/L) of Sprague Dawley rats

| | Week 0 | Week 2 | Week 4 | Week 6 | Week 8 | Week 10 | Week 12 |
|---|---|---|---|---|---|---|---|
| PBS | 84 | 92 | 86 | 79 | 91 | 74 | 81 |
| ISIS 142082 | 87 | 89 | 86 | 126 | 136 | 154 | 149 |
| ISIS 373125 | 79 | 72 | 93 | 124 | 111 | 95 | 81 |
| ISIS 404173 | 75 | 69 | 88 | 75 | 89 | 96 | 83 |
| ISIS 409826 | 75 | 74 | 96 | 112 | 108 | 90 | 106 |
| ISIS 410002 | 67 | 87 | 155 | 173 | 229 | 245 | n/a |
| ISIS 410003 | 71 | 95 | 106 | 136 | 161 | 160 | 186 |
| ISIS 438452 | 70 | 84 | 104 | 157 | 164 | 174 | 167 |
| ISIS 438460 | 79 | 122 | 214 | 287 | 216 | 172 | n/a |
| ISIS 446431 | 73 | 79 | 93 | 137 | 129 | 158 | 153 |
| ISIS 446432 | 80 | 76 | 86 | 99 | 96 | 105 | 102 |
| ISIS 446433 | 77 | 151 | 128 | 234 | n/a | n/a | n/a |
| ISIS 446434 | 81 | 137 | 359 | n/a | n/a | n/a | n/a |

TABLE 30

Effect of antisense oligonucleotide treatment on Bilirubin (mg/dL) of Sprague Dawley rats

| | Week 0 | Week 2 | Week 4 | Week 6 | Week 8 | Week 10 | Week 12 |
|---|---|---|---|---|---|---|---|
| PBS | 0.11 | 0.15 | 0.14 | 0.16 | 0.25 | 0.16 | 0.13 |
| ISIS 142082 | 0.12 | 0.11 | 0.18 | 0.12 | 0.12 | 0.15 | 0.15 |
| ISIS 373125 | 0.13 | 0.13 | 0.15 | 0.36 | 0.14 | 0.15 | 0.13 |
| ISIS 404173 | 0.11 | 0.13 | 0.14 | 0.13 | 0.13 | 0.14 | 0.10 |
| ISIS 409826 | 0.12 | 0.12 | 0.15 | 0.12 | 0.11 | 0.10 | 0.10 |
| ISIS 410002 | 0.11 | 0.13 | 0.18 | 0.13 | 0.19 | 0.54 | n/a |
| ISIS 410003 | 0.12 | 0.12 | 0.14 | 0.16 | 0.14 | 0.17 | 0.14 |
| ISIS 438452 | 0.12 | 0.13 | 0.15 | 0.13 | 0.14 | 0.13 | 0.13 |
| ISIS 438460 | 0.11 | 0.14 | 0.22 | 0.28 | 0.15 | 0.17 | n/a |
| ISIS 446431 | 0.14 | 0.17 | 0.19 | 0.13 | 0.10 | 0.16 | 0.16 |
| ISIS 446432 | 0.12 | 0.14 | 0.13 | 0.12 | 0.11 | 0.14 | 0.13 |
| ISIS 446433 | 0.12 | 0.12 | 0.18 | 0.20 | n/a | n/a | n/a |
| ISIS 446434 | 0.12 | 0.17 | 0.20 | n/a | n/a | n/a | n/a |

TABLE 31

Effect of antisense oligonucleotide treatment on BUN (mg/dL) of Sprague Dawley rats

| | Week 0 | Week 2 | Week 4 | Week 6 | Week 8 | Week 10 | Week 12 |
|---|---|---|---|---|---|---|---|
| PBS | 17 | 20 | 20 | 18 | 26 | 18 | 16 |
| ISIS 142082 | 21 | 23 | 31 | 23 | 31 | 24 | 29 |
| ISIS 373125 | 21 | 21 | 24 | 19 | 31 | 21 | 21 |
| ISIS 404173 | 18 | 19 | 21 | 19 | 25 | 21 | 20 |
| ISIS 409826 | 20 | 21 | 24 | 23 | 28 | 22 | 26 |
| ISIS 410002 | 19 | 22 | 25 | 23 | 29 | 32 | n/a |
| ISIS 410003 | 18 | 20 | 23 | 23 | 30 | 29 | 26 |
| ISIS 438452 | 19 | 22 | 27 | 25 | 29 | 22 | 24 |
| ISIS 438460 | 20 | 23 | 25 | 26 | 31 | 24 | n/a |
| ISIS 446431 | 19 | 21 | 24 | 23 | 29 | 24 | 23 |
| ISIS 446432 | 20 | 21 | 24 | 20 | 29 | 23 | 19 |
| ISIS 446433 | 18 | 21 | 25 | 53 | n/a | n/a | n/a |
| ISIS 446434 | 18 | 23 | 120 | n/a | n/a | n/a | n/a |

TABLE 32

Effect of antisense oligonucleotide treatment on creatinine (mg/dL) of Sprague Dawley rats

| | Week 0 | Week 2 | Week 4 | Week 6 | Week 8 | Week 10 | Week 12 |
|---|---|---|---|---|---|---|---|
| PBS | 0.2 | 0.3 | 0.4 | 0.3 | 0.5 | 0.4 | 0.3 |
| ISIS 142082 | 0.3 | 0.3 | 0.5 | 0.4 | 0.5 | 0.5 | 0.4 |
| ISIS 373125 | 0.3 | 0.3 | 0.6 | 0.4 | 0.6 | 0.6 | 0.4 |
| ISIS 404173 | 0.3 | 0.3 | 0.5 | 0.4 | 0.5 | 0.6 | 0.4 |
| ISIS 409826 | 0.3 | 0.4 | 0.6 | 0.4 | 0.5 | 0.5 | 0.4 |
| ISIS 410002 | 0.3 | 0.3 | 0.6 | 0.4 | 0.5 | 0.5 | n/a |
| ISIS 410003 | 0.3 | 0.3 | 0.6 | 0.4 | 0.6 | 0.6 | 0.4 |
| ISIS 438452 | 0.3 | 0.3 | 0.6 | 0.4 | 0.5 | 0.5 | 0.4 |
| ISIS 438460 | 0.3 | 0.4 | 0.5 | 0.3 | 0.5 | 0.5 | n/a |
| ISIS 446431 | 0.3 | 0.3 | 0.5 | 0.4 | 0.5 | 0.5 | 0.4 |
| ISIS 446432 | 0.3 | 0.3 | 0.6 | 0.4 | 0.5 | 0.5 | 0.4 |
| ISIS 446433 | 0.3 | 0.3 | 0.5 | 0.4 | n/a | n/a | n/a |
| ISIS 446434 | 0.3 | 0.4 | 0.8 | n/a | n/a | n/a | n/a |

TABLE 33

Effect of antisense oligonucleotide treatment on total urine protein to urine creatinine ratio of Sprague Dawley rats

| | Week 0 | Week 2 | Week 4 | Week 6 | Week 8 | Week 10 | Week 12 |
|---|---|---|---|---|---|---|---|
| PBS | 1.5 | 1.4 | 1.2 | 1.6 | 1.3 | 1.2 | 1.2 |
| ISIS 142082 | 1.2 | 4.3 | 4.0 | 7.7 | 6.6 | 7.5 | 7.4 |
| ISIS 373125 | 1.3 | 3.9 | 3.8 | 6.7 | 6.2 | 8.8 | 9.7 |
| ISIS 404173 | 1.1 | 4.8 | 5.5 | 6.4 | 7.4 | 10.2 | 11.9 |
| ISIS 409826 | 1.2 | 3.7 | 3.8 | 5.9 | 9.8 | 28.8 | 37.6 |
| ISIS 410002 | 1.2 | 3.9 | 4.1 | 6.0 | 9.7 | 26.3 | n/a |
| ISIS 410003 | 1.3 | 4.5 | 5.3 | 5.9 | 7.6 | 10.8 | 18.0 |
| ISIS 438452 | 1.4 | 3.3 | 3.1 | 5.1 | 8.0 | 9.2 | 10.5 |
| ISIS 438460 | 1.3 | 4.0 | 4.5 | 7.3 | 16.0 | 53.9 | n/a |
| ISIS 446431 | 1.2 | 4.5 | 5.0 | 5.3 | 7.2 | 8.0 | 8.8 |
| ISIS 446432 | 1.3 | 4.2 | 4.4 | 6.2 | 9.1 | 7.6 | 9.2 |
| ISIS 446433 | 1.1 | 3.4 | 5.7 | 81.5 | n/a | n/a | n/a |
| ISIS 446434 | 1.1 | 3.7 | 25.8 | n/a | n/a | n/a | n/a |

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 34, expressed in mg/dL.

TABLE 34

Effect of antisense oligonucleotide treatment on plasma glucose levels in Sprague Dawley rats

|  | Week 0 | Week 2 | Week 4 | Week 6 | Week 8 | Week 10 | Week 12 |
|---|---|---|---|---|---|---|---|
| PBS | 150 | 140 | 155 | 152 | 163 | 138 | 144 |
| ISIS 142082 | 153 | 137 | 155 | 145 | 142 | 130 | 135 |
| ISIS 373125 | 153 | 135 | 136 | 143 | 133 | 106 | 135 |
| ISIS 404173 | 162 | 138 | 149 | 152 | 145 | 144 | 154 |
| ISIS 409826 | 155 | 141 | 150 | 145 | 143 | 132 | 135 |
| ISIS 410002 | 152 | 139 | 148 | 151 | 130 | 124 | n/a |
| ISIS 410003 | 152 | 138 | 146 | 140 | 132 | 126 | 143 |
| ISIS 438452 | 166 | 134 | 162 | 153 | 135 | 143 | 147 |
| ISIS 438460 | 166 | 140 | 151 | 156 | 150 | 130 | n/a |
| ISIS 446431 | 154 | 143 | 155 | 147 | 153 | 139 | 145 |
| ISIS 446432 | 159 | 141 | 155 | 152 | 152 | 138 | 153 |
| ISIS 446433 | 158 | 138 | 141 | 118 | n/a | n/a | n/a |
| ISIS 446434 | 166 | 149 | 124 | n/a | n/a | n/a | n/a |

Plasma Lipid and Triglyceride Levels

To evaluate the effect of ISIS oligonucleotides on total cholesterol and triglyceride levels, plasma levels of each were measured using an automated clinical chemistry analyzer (Hitachi Olympus AU400e, Melville, N.Y.). Results are presented in Tables 35 and 36, expressed in mg/dL.

TABLE 35

Effect of antisense oligonucleotide treatment on plasma cholesterol levels (mg/dL) in Sprague Dawley rats

|  | Week 0 | Week 2 | Week 4 | Week 6 | Week 8 | Week 10 | Week 12 |
|---|---|---|---|---|---|---|---|
| PBS | 55 | 57 | 64 | 51 | 73 | 64 | 53 |
| ISIS 142082 | 62 | 41 | 54 | 62 | 70 | 64 | 62 |
| ISIS 373125 | 73 | 59 | 66 | 51 | 66 | 61 | 39 |
| ISIS 404173 | 57 | 41 | 68 | 62 | 87 | 85 | 75 |
| ISIS 409826 | 57 | 42 | 79 | 65 | 86 | 122 | 110 |
| ISIS 410002 | 69 | 57 | 75 | 65 | 73 | 96 | n/a |
| ISIS 410003 | 72 | 44 | 70 | 67 | 89 | 76 | 73 |
| ISIS 438452 | 63 | 33 | 53 | 51 | 71 | 70 | 61 |
| ISIS 438460 | 64 | 40 | 98 | 81 | 94 | 146 | n/a |
| ISIS 446431 | 64 | 41 | 56 | 54 | 63 | 68 | 59 |
| ISIS 446432 | 62 | 44 | 70 | 50 | 80 | 80 | 65 |
| ISIS 446433 | 59 | 63 | 95 | 139 | n/a | n/a | n/a |
| ISIS 446434 | 63 | 48 | 91 | n/a | n/a | n/a | n/a |

TABLE 36

Effect of antisense oligonucleotide treatment on plasma triglyceride levels (mg/dL) in Sprague Dawley rats

|  | Week 0 | Week 2 | Week 4 | Week 6 | Week 8 | Week 12 |
|---|---|---|---|---|---|---|
| PBS | 66 | 73 | 82 | 80 | 98 | 106 |
| ISIS 142082 | 92 | 30 | 71 | 44 | 25 | 28 |
| ISIS 373125 | 66 | 28 | 20 | 24 | 24 | 28 |
| ISIS 404173 | 48 | 28 | 28 | 35 | 31 | 49 |
| ISIS 409826 | 68 | 29 | 28 | 25 | 31 | 68 |
| ISIS 410002 | 71 | 23 | 23 | 27 | 71 | n/a |
| ISIS 410003 | 78 | 22 | 22 | 37 | 30 | 64 |
| ISIS 438452 | 89 | 33 | 39 | 34 | 50 | 35 |
| ISIS 438460 | 98 | 20 | 34 | 35 | 33 | n/a |
| ISIS 446431 | 72 | 29 | 38 | 36 | 35 | 48 |
| ISIS 446432 | n/a | 41 | 37 | 31 | 37 | 53 |
| ISIS 446433 | 68 | 21 | 29 | 129 | n/a | n/a |
| ISIS 446434 | 60 | 27 | 103 | n/a | n/a | n/a |

Cytokine Levels

To evaluate the effect of ISIS oligonucleotides on factors involved in inflammation, blood was collected after the end of the treatment period for measurement of cytokine levels. The samples were sent to Aushon Biosystems (Woburn, Mass.) for analysis. Levels of rat IL-6, MCP-1, MIP-1α, and TNF-α were measured with their respective antibodies. The results are presented in Table 37.

TABLE 37

Effect of antisense oligonucleotide treatment on plasma cytokine levels in Sprague Dawley rats

|  | rIL-6 | rMCP-1 | rMP-1α | rTNF-α |
|---|---|---|---|---|
| PBS | 315 | 403 | 6 | 77 |
| ISIS 142082 | 74 | 3082 | 38 | 697 |
| ISIS 373125 | <25 | 2215 | 7 | 15 |
| ISIS 404173 | 125 | 2244 | 60 | 499 |
| ISIS 409826 | <25 | 6041 | 52 | 100 |
| ISIS 410003 | 245 | 3315 | 40 | 444 |
| ISIS 438452 | 105 | 4513 | 26 | 519 |
| ISIS 446431 | 924 | 3104 | 54 | 402 |
| ISIS 446432 | 29 | 2007 | 46 | 610 |

Example 14

Measurement of Viscosity of Isis Antisense Oligonucleotides Targeting Human PTP1B The viscosity of the antisense oligonucleotides selected from studies described in Examples 12 and 13 was measured with the aim of screening out antisense oligonucleotides which have a viscosity more than 40 cP at a concentration of 165-185 mg/mL. Oligonucleotides having a viscosity greater than 40 cP would be too viscous to be administered to any subject.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in Table 38 and indicate that all the antisense oligonucleotides solutions are optimal in their viscosity under the criterion stated above.

TABLE 38

Viscosity and concentration of ISIS antisense oligonucleotides targeting human PTP1B

| ISIS No. | Viscosity (cP) | Concentration (mg/mL) |
|---|---|---|
| 142082 | 3.8 | 188 |
| 404173 | 3.8 | 163 |
| 410003 | 4.5 | 176 |
| 446431 | 3.2 | 180 |
| 446432 | 2.4 | 175 |

Example 15

Six Month Tolerability Study of Antisense Oligonucleotides Targeting Human PTP1B in a Mouse Model ISIS oligonucleotides selected from the studies described in Examples 12-14 were evaluated for long-term tolerability in a mouse model by monitoring changes in the levels of various metabolic markers in CD1 mice.

Treatment

Male CD1 mice were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of ten CD 1 mice each were injected subcutaneously twice a week with 25 mg/kg of ISIS 142082, ISIS 404173, or ISIS 446431 for 24 weeks. One group of ten CD1 mice was injected subcutaneously twice a week with PBS for 24 weeks. This PBS group served as the control group. Blood samples were collected on days 140 via mandibular bleeds. On day 168, blood was collected via terminal cardiac puncture under $CO_2$ anesthesia, the mice were euthanized and organs were harvested for further analysis.

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 39, expressed in mg/dL.

TABLE 39

Effect of antisense oligonucleotide treatment on plasma glucose levels on day 168

|  | Glucose |
|---|---|
| PBS | 214 |
| ISIS 142082 | 177 |
| ISIS 404173 | 204 |
| ISIS 446431 | 191 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) on day 168 were measured. Plasma levels of bilirubin (mg/dL) were also measured using the same clinical chemistry analyzer. Alkaline phosphatase, which is synthesized in increased amounts by damaged liver cells, is also a marker of liver disease (Narayanan, S. Ann. Clin. Lab. Sci. 21: 12-8, 1991) and was similarly measured. Albumin, which is typically decreased in liver disease (Oettl, K. et al., Biochim. Biophys. Acta. 1782: 469-73, 2008), was also similarly measured. The results are presented in Table 40.

TABLE 40

Effect of antisense oligonucleotide treatment on liver metabolic markers on day 168

|  | ALT (IU/L) | AST (IU/L) | Bilirubin (mg/dL) | Alkaline phosphatase (IU/L) | Albumin (g/dL) |
|---|---|---|---|---|---|
| PBS | 50 | 82 | 0.2 | 44 | 2.5 |
| ISIS 142082 | 148 | 197 | 0.1 | 56 | 2.3 |
| ISIS 404173 | 68 | 137 | 0.1 | 57 | 2.5 |
| ISIS 446431 | 115 | 173 | 0.1 | 42 | 2.4 |

Cardiac Function

To evaluate the effect of ISIS oligonucleotides on heart function, plasma levels of creatine phosphokinase (CPK) were measured using an automated clinical chemistry analyzer (Hitachi Olympus AU400e, Melville, N.Y.) on day 168. An increased level of this marker indicates heart muscle injury (Barohn, R. J. In: Goldman L, Ausiello D, eds. *Cecil Medicine*. 23rd ed. Philadelphia, Pa.: Saunders Elsevier; 2007: chapter 447). The results are presented in Table 41.

TABLE 41

Effect of antisense oligonucleotide treatment on cardiac marker CPK on day 168

|  | CPK (IU/L) |
|---|---|
| PBS | 98 |
| ISIS 142082 | 120 |
| ISIS 404173 | 107 |
| ISIS 446431 | 159 |

Pancreatic Function

To evaluate the effect of ISIS oligonucleotides on pancreatic function, plasma levels of amylase were measured using an automated clinical chemistry analyzer (Hitachi Olympus AU400e, Melville, N.Y.) on day 168. An increased level of this marker indicates acute pancreatitis (Sternby, B. et al., Mayo Clin. Proc. 71: 1138-44, 1996). The results are presented in Table 42.

TABLE 42

Effect of antisense oligonucleotide treatment on pancreatic marker amylase on day 168

|  | Amylase (IU/L) |
|---|---|
| PBS | 1101 |
| ISIS 142082 | 1374 |
| ISIS 404173 | 1280 |
| ISIS 446431 | 1232 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in Table 43, expressed in mg/dL.

TABLE 43

Effect of antisense oligonucleotide treatment
on kidney metabolic markers on day 168

|  | BUN | Creatinine |
|---|---|---|
| PBS | 20 | 0.3 |
| ISIS 142082 | 24 | 0.2 |
| ISIS 404173 | 21 | 0.2 |
| ISIS 446431 | 19 | 0.3 |

Example 16

Measurement of Half-Life of Antisense
Oligonucleotide in CD1 Mouse Liver

CD1 mice were treated with the ISIS antisense oligonucleotides selected from studies described in Example 14, and the oligonucleotide half-life as well as the elapsed time for oligonucleotide degradation and elimination from the liver was evaluated.

Treatment

Groups of ten CD1 mice each were injected subcutaneously twice per week for 2 weeks with 50 mg/kg of ISIS 142082, ISIS 446431, ISIS 404173, or ISIS 409826. Five mice from each group were sacrificed 3 days and 56 days following the final dose. Livers were harvested for analysis.

Measurement of Oligonucleotide Concentration

The concentration of the full-length oligonucleotide was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCT-TGCGTTTTTT, designated herein as SEQ ID NO: 50) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Table 44. Antisense oligonucleotides with half-lives within 11-34 days were chosen for further studies.

TABLE 44

Full-length oligonucleotide concentration (µg/g) and
half-life (days) of oligonucleotide in CD1 mouse liver

|  | Days | Full length conc. (mg/g) | Half-life (days) |
|---|---|---|---|
| 142082 | 3 | 265 | 19.8 |
|  | 56 | 42 |  |
| 446431 | 3 | 293 | 19.6 |
|  | 56 | 45 |  |
| 404173 | 3 | 281 | 14.8 |
|  | 56 | 24 |  |
| 409826 | 3 | 304 | 18.4 |
|  | 56 | 41 |  |

Example 17

Effect of Isis Antisense Oligonucleotides Targeting
Human PTP1B in Cynomolgus Monkeys Cynomolgus monkeys were treated with ISIS antisense oligonucleotides from studies described in Examples 15 and 16. Antisense oligonucleotide efficacy and tolerability, as well as their pharmacokinetic profile in the liver and kidney, were evaluated.

Treatment

Prior to the study, the monkeys were kept in quarantine for a 30-day time period, during which standard panels of serum chemistry and hematology, examination of fecal samples for ova and parasites, and a tuberculosis test, were conducted to screen out abnormal or ailing monkeys. Six groups of randomly assigned three male and two female cynomolgus monkeys each were injected subcutaneously thrice per week for the first week, and subsequently, once a week for the next 12 weeks with either 8 mg/kg or 40 mg/kg of ISIS 142082, ISIS 446431, or ISIS 404173. One group of three male and two female cynomolgus monkeys was injected subcutaneously thrice per week for the first week, and subsequently, once a week for the next 12 weeks with 40 mg/kg of ISIS 409826. A control group of three male and two female cynomolgus monkeys was injected subcutaneously thrice per week for the first week, and subsequently, once a week for the next 12 weeks with PBS. Terminal sacrifices of all groups were conducted 48 hours after the last dose, on day 93.

During the study period, the monkeys were observed daily for signs of illness or distress. Any animal showing adverse effects to the treatment was removed and referred to the veterinarian and Study Director.

Inhibition Studies
RNA Analysis

RNA was extracted from liver and the abdominal adipose tissues for real-time PCR analysis of PTP1B using primer probe set 1 (forward sequence GACCAGCTGCGCTTCTC-CTA, designated herein as SEQ ID NO: 51; reverse sequence CAGAGGAGTCCCCCATGATG, designated herein as SEQ ID NO: 52; probe sequence TTGGCTGTGATCGAAGGT-GCCAAA, designated herein as SEQ ID NO: 53) or primer probe set 2 (forward sequence GGGCCCTTTGCCTAA-CACA, designated herein as SEQ ID NO: 54; reverse sequence CGACACCCCTGCTTTTCTG, designated herein as SEQ ID NO: 55; probe sequence CGGTCACTTTTGG-GAGATGGTGTGG, designated herein as SEQ ID NO: 56), each targeting different regions of the PTP1B mRNA. Results are presented as percent reduction of PTP1B mRNA, relative to PBS control, normalized with RIBOGREEN®. As shown in Table 45, treatment with ISIS antisense oligonucleotides resulted in significant reduction of PTP1B mRNA in comparison to the PBS control. Treatment with ISIS 404173 caused reduction of PTP1B mRNA levels similar to that with treatment with ISIS 142082.

TABLE 45

Inhibition of PTP1B mRNA in the cynomolgus monkey
liver and fat tissue relative to the PBS control

| ISIS No. | Dose (mg/kg) | % inhibition in liver (probe set 1) | % inhibition in liver (probe set 2) | % inhibition in fat (probe set 1) | % inhibition in fat (probe set 2) |
|---|---|---|---|---|---|
| 409826 | 40 | 38 | 45 | 17 | 21 |
| 142082 | 8 | 12 | 14 | 13 | 16 |
|  | 40 | 46 | 48 | 34 | 28 |
| 446831 | 8 | 0 | 8 | 6 | 1 |
|  | 40 | 8 | 18 | 14 | 12 |
| 404173 | 8 | 4 | 13 | 8 | 4 |
|  | 40 | 26 | 22 | 38 | 31 |

Protein Analysis

Tissue was extracted from liver For measuring PTP1B protein levels by western blot analysis. Specifically, PTP1B protein samples from monkeys treated with ISIS 404173 were compared with those treated with ISIS 142082. The results are presented in Tables 46, 47 and 48 expressed as percentage reduction compared to control levels. The levels of PTP1B levels were normalized against total protein levels, as well as against a constitutively expressed protein, IR-β. Treatment with ISIS 404173 caused greater reduction of PTP1B liver protein to that with treatment with ISIS 142082 at the lower dose of 8 mg/kg (Table 47).

TABLE 46

PTP1B protein level reduction after treatment with ISIS 404173 in the cynomolgus monkey liver

| Dose (mg/kg) | % inhibition (normalized to total protein) | % inhibition (normalized to IR-β) |
|---|---|---|
| 8 | 49 | 42 |
| 40 | 67 | 66 |

TABLE 47

PTP1B protein level reduction after treatment with ISIS 404173 or ISIS 142082 at 8 mg/kg in the cynomolgus monkey liver

| ISIS No | % inhibition (normalized to total protein) | % inhibition (normalized to IR-β) |
|---|---|---|
| 142082 | 20 | 4 |
| 404173 | 33 | 27 |

TABLE 48

PTP1B protein level reduction after treatment with ISIS 404173 or ISIS 142082 at 40 mg/kg in the cynomolgus monkey liver

| ISIS No | % inhibition (normalized to total protein) | % inhibition (normalized to IR-β) |
|---|---|---|
| 142082 | 65 | 63 |
| 404173 | 60 | 56 |

Tolerability Studies
Body and Organ Weight Measurements

To evaluate the effect of ISIS oligonucleotides on the overall health of the animals, body and organ weights were measured after terminal sacrifice. Body weights were measured and compared to that of the PBS control animals. Organ weights were measured and treatment group weights were compared to the corresponding PBS control weights. The data is presented in Table 49. Treatment with ISIS 142082 did cause increases in liver and kidney weights at the higher dose.

TABLE 49

Final body and organ weight weights in the cynomolgus monkey relative to the control

| | Dose (mg/kg) | Body weight (kg) | Kidney (g) | Liver (g) | Spleen (g) | Gastocnemius muscle (g) |
|---|---|---|---|---|---|---|
| PBS | — | 2.2 | 9.6 | 10.5 | 2.3 | 10.6 |
| 409826 | 40 | 2.3 | 14.0 | 18.5 | 6.0 | 8.8 |
| 142082 | 8 | 2.3 | 10.6 | 13.0 | 3.7 | 9.5 |
| | 40 | 2.2 | 20.9 | 17.7 | 7.0 | 9.0 |
| 446431 | 8 | 2.3 | 11.6 | 12.7 | 4.8 | 10.2 |
| | 40 | 2.3 | 15.9 | 16.1 | 9.6 | 7.7 |

TABLE 49-continued

Final body and organ weight weights in the cynomolgus monkey relative to the control

| | Dose (mg/kg) | Body weight (kg) | Kidney (g) | Liver (g) | Spleen (g) | Gastocnemius muscle (g) |
|---|---|---|---|---|---|---|
| 404173 | 8 | 2.3 | 11.6 | 12.8 | 4.8 | 11.1 |
| | 40 | 2.2 | 14.8 | 15.5 | 3.7 | 8.7 |

Liver Function

To evaluate the effect of ISIS oligonucleotides on hepatic function, blood samples were collected from all the study groups 7 days before the start of treatment, as well as on days 30, 58, and 93 of the treatment period. The blood samples were collected in tubes without any anticoagulant for serum separation. The tubes were kept at room temperature for 90 min and then centrifuged (3000 rpm for 10 min at room temperature) to obtain serum.

Levels of transaminases were measured using a Toshiba 200FR NEO chemistry analyzer (Toshiba Co., Japan). Plasma levels of ALT (alanine transaminase) and AST (aspartate transaminase) were measured and the results are presented in Tables 50 and 51, expressed in IU/L. Alkaline phosphatase, which is synthesized in increased amounts by damaged liver cells and is also a marker of liver disease and was similarly measured, and the data is presented in Table 52. The levels of AST, ALT and alkaline phosphatase in all the treatment groups were similar to that of the PBS control group.

C-reactive protein (CRP), which is synthesized in the liver and which serves as a marker of inflammation, was also similarly measured, and the data is presented in Table 53. Treatment with ISIS 142082 and ISIS 409826 at the higher dose resulted in high levels of CRP, suggesting liver inflammation.

Bilirubin is also a liver metabolic marker and was similarly measured and is presented in Table 54, expressed in mg/dL. Bilirubin levels of all the treatment groups were found to be similar to that of the PBS control group. Gamma-glutamyl-transferase (GGT) is an enzyme produced in the liver and is a useful laboratory marker for early liver damage or cholestatic disease (Betro, M. G. et al., Am. J. Clin. Pathol. 60: 672-8, 1973). GGT levels were measured and the results are presented in Table 55, and demonstrate no difference between the PBS control and the treatment groups.

TABLE 50

Effect of antisense oligonucleotide treatment on ALT (IU/L) in cynomolgus monkey serum

| | Dose (mg/kg) | Day −7 | Day 30 | Day 58 | Day 93 |
|---|---|---|---|---|---|
| PBS | — | 37 | 44 | 42 | 35 |
| 409826 | 40 | 39 | 51 | 86 | 74 |
| 142082 | 8 | 37 | 39 | 45 | 36 |
| | 40 | 49 | 62 | 59 | 69 |
| 446431 | 8 | 52 | 54 | 67 | 86 |
| | 40 | 38 | 58 | 87 | 99 |
| 404173 | 8 | 34 | 50 | 41 | 45 |
| | 40 | 44 | 50 | 63 | 73 |

TABLE 51

Effect of antisense oligonucleotide treatment on AST (IU/L) in cynomolgus monkey serum

| | Dose (mg/kg) | Day −7 | Day 30 | Day 58 | Day 93 |
|---|---|---|---|---|---|
| PBS | — | 40 | 49 | 55 | 44 |
| 409826 | 40 | 48 | 53 | 73 | 59 |
| 142082 | 8 | 44 | 45 | 49 | 42 |
| | 40 | 54 | 70 | 72 | 69 |
| 446431 | 8 | 57 | 43 | 48 | 50 |
| | 40 | 41 | 60 | 63 | 81 |
| 404173 | 8 | 44 | 53 | 57 | 59 |
| | 40 | 46 | 65 | 71 | 74 |

TABLE 52

Effect of antisense oligonucleotide treatment on alkaline phosphatase (IU/L) in cynomolgus monkey serum

| | Dose (mg/kg) | Day −7 | Day 30 | Day 58 | Day 93 |
|---|---|---|---|---|---|
| PBS | — | 784 | 834 | 1021 | 838 |
| 409826 | 40 | 728 | 883 | 1178 | 981 |
| 142082 | 8 | 718 | 739 | 788 | 688 |
| | 40 | 666 | 656 | 711 | 774 |
| 446431 | 8 | 742 | 745 | 885 | 908 |
| | 40 | 778 | 759 | 768 | 735 |
| 404173 | 8 | 888 | 957 | 1135 | 1155 |
| | 40 | 931 | 958 | 1135 | 1263 |

TABLE 53

Effect of antisense oligonucleotide treatment on CRP (mg/L) in cynomolgus monkey plasma

| | Dose (mg/kg) | Day −7 | Day 30 | Day 58 | Day 93 |
|---|---|---|---|---|---|
| PBS | | 1.0 | 1.8 | 1.4 | 1.2 |
| 409826 | 40 | 1.0 | 4.3 | 4.8 | 4.8 |
| 142082 | 8 | 0.8 | 1.2 | 0.9 | 1.0 |
| | 40 | 0.8 | 2.6 | 3.4 | 12.1 |
| 446431 | 8 | 1.4 | 1.4 | 0.9 | 1.1 |
| | 40 | 0.8 | 2.4 | 2.2 | 6.7 |
| 404173 | 8 | 1.4 | 1.9 | 1.5 | 1.8 |
| | 40 | 3.1 | 1.6 | 1.2 | 1.6 |

TABLE 54

Effect of antisense oligonucleotide treatment on bilirubin (mg/dL) in cynomolgus monkey plasma

| | Dose (mg/kg) | Day −7 | Day 30 | Day 58 | Day 93 |
|---|---|---|---|---|---|
| PBS | — | 0.19 | 0.20 | 0.20 | 0.17 |
| 409826 | 40 | 0.17 | 0.13 | 0.13 | 0.10 |
| 142082 | 8 | 0.17 | 0.18 | 0.16 | 0.14 |
| | 40 | 0.16 | 0.13 | 0.13 | 0.08 |
| 446431 | 8 | 0.21 | 0.17 | 0.18 | 0.15 |
| | 40 | 0.19 | 0.18 | 0.15 | 0.12 |
| 404173 | 8 | 0.23 | 0.19 | 0.20 | 0.16 |
| | 40 | 0.22 | 0.15 | 0.14 | 0.13 |

TABLE 55

Effect of antisense oligonucleotide treatment on GGT (IU/L) in cynomolgus monkey plasma

| | Dose (mg/kg) | Day −7 | Day 30 | Day 58 | Day 93 |
|---|---|---|---|---|---|
| PBS | — | 65 | 74 | 79 | 71 |
| 409826 | 40 | 84 | 86 | 94 | 87 |
| 142082 | 8 | 63 | 67 | 68 | 62 |
| | 40 | 67 | 72 | 71 | 61 |
| 446431 | 8 | 60 | 62 | 62 | 63 |
| | 40 | 61 | 58 | 62 | 60 |
| 404173 | 8 | 57 | 66 | 66 | 68 |
| | 40 | 56 | 63 | 69 | 79 |

Kidney Function

To evaluate the effect of ISIS oligonucleotides on kidney function, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Levels of BUN and creatinine were measured 7 days before the start of treatment, as well as on days 30, 58, and 93 of the treatment period using a Toshiba 200FR NEO chemistry analyzer (Toshiba Co., Japan). Results are presented in Tables 56 and 57, expressed in mg/dL. Treatment with ISIS oligonucleotides had no adverse effect on either BUN or creatinine levels.

TABLE 56

Effect of antisense oligonucleotide treatment on serum BUN levels (mg/dL) in cynomolgus monkeys

| | Dose (mg/kg) | Day −7 | Day 30 | Day 58 | Day 93 |
|---|---|---|---|---|---|
| PBS | — | 28 | 28 | 25 | 28 |
| 409826 | 40 | 32 | 30 | 28 | 32 |
| 142082 | 8 | 26 | 25 | 24 | 26 |
| | 40 | 28 | 28 | 25 | 25 |
| 446431 | 8 | 28 | 27 | 25 | 26 |
| | 40 | 28 | 27 | 25 | 28 |
| 404173 | 8 | 28 | 30 | 24 | 27 |
| | 40 | 28 | 24 | 25 | 23 |

TABLE 57

Effect of antisense oligonucleotide treatment on serum creatinine levels (mg/dL) in cynomolgus monkeys

| | Dose (mg/kg) | Day −7 | Day 30 | Day 58 | Day 93 |
|---|---|---|---|---|---|
| PBS | | 0.83 | 0.88 | 0.94 | 0.78 |
| 409826 | 40 | 0.77 | 0.84 | 0.92 | 0.82 |
| 142082 | 8 | 0.74 | 0.78 | 0.79 | 0.71 |
| | 40 | 0.72 | 0.80 | 0.86 | 0.73 |
| 446431 | 8 | 0.79 | 0.75 | 0.83 | 0.71 |
| | 40 | 0.76 | 0.83 | 0.88 | 0.77 |
| 404173 | 8 | 0.81 | 0.91 | 0.87 | 0.82 |
| | 40 | 0.76 | 0.84 | 0.92 | 0.76 |

Cholesterol and Triglyceride Levels

To evaluate the effect of ISIS oligonucleotides on lipid metabolism, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Concentrations of cholesterol and triglycerides were measured 7 days before the start of treatment, as well as on days 30, 58, and 93 of the treatment period using a Toshiba 200FR NEO chemistry analyzer (Toshiba Co., Japan). Results are presented in Tables 58 and 59, expressed in mg/dL. Treatment with ISIS oligonucleotides had no adverse effect on either cholesterol or triglyceride levels.

TABLE 58

Effect of antisense oligonucleotide treatment on serum cholesterol levels (mg/dL) in cynomolgus monkeys

|  | Dose (mg/kg) | Day −7 | Day 30 | Day 58 | Day 93 |
|---|---|---|---|---|---|
| PBS | — | 135 | 163 | 162 | 143 |
| 409826 | 40 | 153 | 150 | 140 | 116 |
| 142082 | 8 | 116 | 151 | 159 | 141 |
|  | 40 | 110 | 140 | 138 | 128 |
| 446431 | 8 | 125 | 144 | 141 | 133 |
|  | 40 | 93 | 99 | 95 | 81 |
| 404173 | 8 | 123 | 147 | 149 | 136 |
|  | 40 | 135 | 135 | 125 | 124 |

TABLE 59

Effect of antisense oligonucleotide treatment on serum triglyceride levels (mg/dL) in cynomolgus monkeys

|  | Dose (mg/kg) | Day −7 | Day 30 | Day 58 | Day 93 |
|---|---|---|---|---|---|
| PBS | — | 47 | 55 | 45 | 54 |
| 409826 | 40 | 30 | 29 | 33 | 42 |
| 142082 | 8 | 23 | 31 | 37 | 32 |
|  | 40 | 28 | 28 | 35 | 42 |
| 446431 | 8 | 24 | 46 | 34 | 33 |
|  | 40 | 31 | 44 | 47 | 56 |
| 404173 | 8 | 28 | 38 | 25 | 28 |
|  | 40 | 30 | 38 | 45 | 34 |

Hematology

To evaluate any inflammatory effect of ISIS oligonucleotides in cynomolgus monkeys, blood samples were approximately 0.5 mL of blood was collected from each of the available study animals in tubes containing the potassium salt of EDTA. Samples were analyzed for red blood cell (RBC) count, white blood cells (WBC) count, platelet count and hemoglobin content, using an ADVIA120 hematology analyzer (Bayer, USA). The data is presented in Tables 60-63. Treatment with ISIS oligonucleotides did not significantly alter the blood cell count or hemoglobin levels, compared to the control.

TABLE 60

Effect of antisense oligonucleotide treatment on WBC ($\times 10^3/\mu L$) in cynomolgus monkeys

|  | Dose (mg/kg) | Day −7 | Day 30 | Day 58 | Day 93 |
|---|---|---|---|---|---|
| PBS | — | 11.6 | 12.6 | 11.1 | 8.9 |
| 409826 | 40 | 12.4 | 12.7 | 15.3 | 10.8 |
| 142082 | 8 | 11.3 | 15.2 | 12.8 | 9.7 |
|  | 40 | 11.9 | 13.2 | 12.5 | 8.5 |
| 446431 | 8 | 9.7 | 13.4 | 12.7 | 9.3 |
|  | 40 | 10.7 | 11.5 | 11.9 | 10.2 |
| 404173 | 8 | 14.9 | 18.9 | 14.9 | 11.8 |
|  | 40 | 11.1 | 14.2 | 12.9 | 10.8 |

TABLE 61

Effect of antisense oligonucleotide treatment on RBC ($\times 10^6/\mu L$) in cynomolgus monkeys

|  | Dose (mg/kg) | Day −7 | Day 30 | Day 58 | Day 93 |
|---|---|---|---|---|---|
| PBS | — | 5.5 | 5.6 | 5.8 | 5.1 |
| 409826 | 40 | 5.6 | 5.8 | 6.1 | 5.6 |
| 142082 | 8 | 5.4 | 5.4 | 5.6 | 5.2 |
|  | 40 | 5.7 | 5.6 | 5.8 | 5.5 |
| 446431 | 8 | 5.5 | 5.3 | 5.5 | 5.4 |
|  | 40 | 5.5 | 5.4 | 5.8 | 5.3 |
| 404173 | 8 | 5.9 | 5.9 | 6.1 | 5.7 |
|  | 40 | 5.1 | 5.4 | 5.5 | 5.5 |

TABLE 62

Effect of antisense oligonucleotide treatment on platelets ($\times 10^3/\mu L$) in cynomolgus monkeys

|  | Dose (mg/kg) | Day −7 | Day 30 | Day 58 | Day 93 |
|---|---|---|---|---|---|
| PBS | — | 592 | 555 | 571 | 516 |
| 409826 | 40 | 536 | 493 | 400 | 338 |
| 142082 | 8 | 439 | 477 | 349 | 284 |
|  | 40 | 461 | 454 | 401 | 263 |
| 446431 | 8 | 438 | 397 | 359 | 282 |
|  | 40 | 516 | 337 | 369 | 323 |
| 404173 | 8 | 489 | 491 | 420 | 355 |
|  | 40 | 520 | 470 | 389 | 316 |

TABLE 63

Effect of antisense oligonucleotide treatment on hemoglobin levels (g/dL) in cynomolgus monkeys

|  | Dose (mg/kg) | Day −7 | Day 30 | Day 58 | Day 93 |
|---|---|---|---|---|---|
| PBS | — | 12.5 | 12.8 | 13.1 | 11.9 |
| 409826 | 40 | 12.6 | 12.8 | 13.3 | 12.5 |
| 142082 | 8 | 12.3 | 12.5 | 13.0 | 12.2 |
|  | 40 | 12.1 | 12.0 | 12.1 | 11.5 |
| 446431 | 8 | 12.3 | 12.1 | 12.4 | 12.6 |
|  | 40 | 12.7 | 12.6 | 13.3 | 12.4 |
| 404173 | 8 | 12.7 | 13.0 | 13.3 | 12.7 |
|  | 40 | 11.6 | 12.3 | 12.4 | 12.6 |

Analysis of Factors of Inflammation

To evaluate the effect of ISIS oligonucleotides for complement C3 analysis as an inflammation factor, blood was collected from all available animals in tubes without anticoagulant for serum separation. The tubes were kept at room temperature for 90 min and then centrifuged (3000 rpm for 10 min at room temperature) to obtain serum. Complement C3 was measured using an automatic analyzer (Toshiba 200 FR NEO chemistry analyzer, Toshiba co., Japan). The data is presented in Table 64, expressed in mg/dL. Treatment with ISIS 409826 resulted in low complement C3 levels, indicating a diseased state.

TABLE 64

Effect of antisense oligonucleotide treatment on serum C3 levels (mg/dL) in cynomolgus monkeys

|  | Dose (mg/kg) | Day −7 | Day −1 | Day 30 | Day 58 | Day 93 |
|---|---|---|---|---|---|---|
| PBS | — | 136 | 138 | 148 | 149 | 129 |
| 409826 | 40 | 129 | 131 | 101 | 101 | 90 |

TABLE 64-continued

Effect of antisense oligonucleotide treatment on
serum C3 levels (mg/dL) in cynomolgus monkeys

|  | Dose (mg/kg) | Day -7 | Day -1 | Day 30 | Day 58 | Day 93 |
|---|---|---|---|---|---|---|
| 142082 | 8 | 126 | 135 | 126 | 127 | 111 |
|  | 40 | 133 | 134 | 106 | 121 | 111 |
| 446431 | 8 | 130 | 144 | 128 | 132 | 125 |
|  | 40 | 129 | 130 | 111 | 117 | 114 |
| 404173 | 8 | 127 | 136 | 137 | 136 | 127 |
|  | 40 | 125 | 134 | 101 | 103 | 102 |

Analysis of Insulin Levels

To evaluate the effect of ISIS oligonucleotides on the thyroid gland, blood was collected on days 42, 84 and 91 from animals fasted overnight in tubes treated with EDTA. The tubes were kept on ice and plasma was obtained after centrifugation (3000 rpm for 10 min at 4° C.) within 30 min of blood collection. Insulin levels were measured using an automatic analyzer (Toshiba 200 FR NEO chemistry analyzer, Toshiba co., Japan). The data is presented in Table 65, expressed in ng/mL.

TABLE 65

Effect of antisense oligonucleotide treatment on plasma
insulin levels (ng/mL) in cynomolgus monkeys

|  | Dose (mg/kg) | Day 42 | Day 84 | Day 91 |
|---|---|---|---|---|
| PBS | — |  | 29 | 26 | 26 |
| 409826 | 40 | 14 | 22 | 15 |
| 142082 | 8 | 8 | 4 | 8 |
|  | 40 | 8 | 10 | 10 |
| 404173 | 8 | 9 | 10 | 7 |
|  | 40 | 6 | 3 | 2 |

Pharmacokinetic Studies
Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-β-methoxyethyl modified phosphorothioate oligonucleotide, GCGTTTGCTCTTCTTCTTGCGTTTTTT, designated herein as SEQ ID NO: 50) was added prior to extraction. Tissue sample concentrations were calculated using calibration curves, with a lower limit of quantitation (LLOQ) of approximately 1.14 µg/g. The results are presented in Tables 66 and 67, expressed as µg/g tissue. The ratio of the concentrations in the kidney versus the liver was calculated. Treatment with ISIS oligonucleotides did not result in any abnormality in the ratio. The results indicate that ISIS 404173 is a better renal accumulator than ISIS 142082 at the higher dose.

TABLE 66

Total oligonucleotide concentration (µg/g)
in the liver of cynomolgus monkey

| ISIS No. | Dose (mg/kg) | Kidney | Liver | Kidney/Liver ratio |
|---|---|---|---|---|
| 409826 | 40 | 4424 | 954 | 4.64 |
| 142082 | 8 | 1688 | 1044 | 1.62 |
|  | 40 | 6385 | 1774 | 3.60 |
| 446431 | 8 | 1323 | 641 | 2.06 |
|  | 40 | 6662 | 1159 | 5.75 |
| 404173 | 8 | 971 | 712 | 1.36 |
|  | 40 | 7180 | 1464 | 4.90 |

TABLE 67

Full-length oligonucleotide concentration
(µg/g) in the liver of cynomolgus monkey

| ISIS No. | Dose (mg/kg) | Kidney | Liver | Kidney/Liver ratio |
|---|---|---|---|---|
| 409826 | 40 | 3472 | 728 | 4.77 |
| 142082 | 8 | 1232 | 653 | 1.89 |
|  | 40 | 4103 | 1244 | 3.30 |
| 446431 | 8 | 1204 | 416 | 2.89 |
|  | 40 | 5645 | 846 | 6.67 |
| 404173 | 8 | 650 | 424 | 1.53 |
|  | 40 | 5039 | 1094 | 4.61 |

What is claimed is:

1. A pharmaceutical composition suitable for parenteral administration to an animal comprising an aqueous solution, said aqueous solution comprising:
   a pharmaceutically acceptable carrier or diluent; and
   a single stranded modified oligonucleotide targeted to PTP1B consisting of 20 linked nucleosides having a nucleobase sequence consisting of SEQ ID NO: 26, or salt thereof,
   wherein the carrier or diluent is sterile and the aqueous solution is suitably viscous for parenteral administration.

2. The pharmaceutical composition of claim 1, wherein the aqueous solution suitably viscous for parenteral administration has a viscosity level less than 40 centipoise (cP).

3. The pharmaceutical composition of claim 2, wherein the parenteral administration is subcutaneous injection.

4. The pharmaceutical composition of claim 2, wherein the parenteral administration is intravenous infusion.

5. The pharmaceutical composition of claim 1, wherein the modified oligonucleotide comprises:
   a gap segment consisting of ten linked deoxynucleosides;
   a 5' wing segment consisting of five linked nucleosides; and
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage, and wherein each cytosine of the modified oligonucleotide is a 5-methylcytosine.

6. The pharmaceutical composition of claim 5, wherein the aqueous solution suitably viscous for parenteral administration has a viscosity level less than 40 centipoise (cP).

7. The pharmaceutical composition of claim 6, wherein the aqueous solution comprises the modified oligonucleotide targeted to PTP1B at a concentration of about 165-185 mg/mL.

8. The pharmaceutical composition of claim 7, wherein the aqueous solution has a temperature of about 25° C.

9. The pharmaceutical composition of claim 8, wherein the parenteral administration is subcutaneous injection.

10. The pharmaceutical composition of claim 8, wherein the parenteral administration is intravenous infusion.

11. The pharmaceutical composition of claim 1, wherein the pharmaceutically acceptable carrier or diluent is water.

12. The pharmaceutical composition of claim 11, wherein the modified oligonucleotide comprises:
    a gap segment consisting of ten linked deoxynucleosides;
    a 5' wing segment consisting of five linked nucleosides; and
    a 3' wing segment consisting of five linked nucleosides;
    wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage, and wherein each cytosine of the modified oligonucleotide is a 5-methylcytosine.

13. The pharmaceutical composition of claim 12, wherein the aqueous solution suitably viscous for parenteral administration has a viscosity level less than 40 centipoise (cP).

14. The pharmaceutical composition of claim 13, wherein the aqueous solution comprises the modified oligonucleotide targeted to PTP1B at a concentration of about 165-185 mg/mL.

15. The pharmaceutical composition of claim 14, wherein the aqueous solution has a temperature of about 25° C.

16. The pharmaceutical composition of claim 15, wherein the parenteral administration is subcutaneous injection.

17. The pharmaceutical composition of claim 16, wherein the parenteral administration is intravenous infusion.

* * * * *

UNITED STATES PATENT AND TRADEMARK OFFICE
CERTIFICATE OF CORRECTION

PATENT NO.         : 8,658,783 B2
APPLICATION NO.    : 13/446763
DATED              : February 25, 2014
INVENTOR(S)        : Bhanot et al.

It is certified that error appears in the above-identified patent and that said Letters Patent is hereby corrected as shown below:

On the Title Page

Page 1 (item 74, Attorney) at line 2, Change "Dept." to --Dept.; Knobbe Martens Olson & Bear LLP.--.

In column 1 (page 2, item 56) at line 15, Under Other Publications, change "fin"" to --find"--.

In column 1 (page 2, item 56) at line 24, Under Other Publications, change "transolcation" to --translocation--.

In column 1 (page 2, item 56) at line 39, Under Other Publications, change "rosigitazone," to --rosiglitazone,--.

In column 1 (page 2, item 56) at line 55, Under Other Publications, change "phosphorothiaote" to --phosphorothioate--.

In column 1 (page 2, item 56) at line 59, Under Other Publications, change "ceullular" to --cellular--.

In column 1 (page 3, item 56) at line 7, Under Other Publications, change "glucagan" to --glucagon--.

In column 2 (page 3, item 56) at line 2, Under Other Publications, change "insuliun" to --insulin--.

In column 2 (page 3, item 56) at line 10, Under Other Publications, change "parmacokinetics," to --pharmacokinetics,--.

In column 2 (page 3, item 56) at line 66, Under Other Publications, change "phsphatase" to --phosphatase--.

In the Specification

In column 1 at line 38, Change "PTP" to --PTP1B--.

Signed and Sealed this
Fourteenth Day of October, 2014

Michelle K. Lee
*Deputy Director of the United States Patent and Trademark Office*

In column 5 at line 26, Change "(VDL," to --(VLDL,--.

In column 7 at line 44, Change "non-1-IDL-C," to --non-HDL-C,--.

In column 8 at line 58, Change "cytokines" to --cytokines.--.

In column 11 at line 9, Change "includes" to --include--.

In column 12 at line 11, Change "404173" to --404173.--.

In column 12 at line 44, Change "404173" to --404173.--.

In column 14 at line 3, Change "438472," to --438472.--.

In column 14 at line 37, Change "438472," to --438472.--.

In column 15 at line 8 (approx.), Change "404173" to --404173.--.

In column 21 at line 15, Change "PTP" to --PTP1B--.

In column 21 at line 16, Change "PTP" to --PTP1B--.

In column 28 at line 64, Change "preceeding" to --preceding--.

In column 30 at line 46, Change "and for" to --and/or--.

In column 32 at line 64, Change "substitutent" to --substituent--.

In column 34 at line 34, Change "($R_aR_b$)" to --($R_a$)($R_b$)--.

In column 36 at line 30 (approx.), Change "-($Q_a$" to -- -$Q_a$--.

In column 38 at line 24, Change "comformationally" to --conformationally--.

In column 39 at line 5, Change ""monocylic" to --"monocyclic--.

In column 39 at line 49, Change "manitol" to --mannitol--.

In column 42 at line 63, Change "Manassus," to --Manassas--.

In column 44 at line 3, Change "PRISMS" to --PRISM®--.

In column 46 at line 13, Change "PT1B" to --PTP1B--.

In column 51 at line 17, Change "heterogenous" to --heterogeneous--.

In column 52 at lines 13-18, Delete "DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA)" and insert the same on Col. 52, line 13 as a continuation of the paragraph.

In column 52 at line 15, Change "distearolyphosphatidyl" to --distearoylphosphatidyl)--.

In column 52 at line 34, Change "bis-chloroethylnitrosurea," to --bis-chloroethylnitrosourea,--.

In column 52 at line 38, Change "methylcyclohexylnitrosurea," to --methylcyclohexylnitrosourea,--.

In column 52 at line 55, Change "ribivirin," to --ribavirin,--.

In columns 63-64 at line 9 (Table 6), Change "303174T" to --404174--.

CERTIFICATE OF CORRECTION (continued)
U.S. Pat. No. 8,658,783 B2

In column 93 at line 60 (approx.), Change "Gastocnemius" to --Gastrocnemius--.

In column 94 at line 6, Change "Gastocnemius" to --Gastrocnemius--.

In column 99 at line 45 (approx.), Change "β" to --O--.

SEQUENCE LISTING

<160> NUMBER OF SEQ ID NOS: 56

<210> SEQ ID NO 1
<211> LENGTH: 3318
<212> TYPE: DNA
<213> ORGANISM: Homo sapiens

<400> SEQUENCE: 1

```
gtgatgcgta gttccggctg ccggttgaca tgaagaagca gcagcggcta gggcggcggt      60
agctgcaggg gtcggggatt gcagcgggcc tcggggctaa gagcgcgacg cggcctagag     120
cggcagacgg cgcagtgggc cgagaaggag gcgcagcagc cgccctggcc cgtcatggag     180
atggaaaagg agttcgagca gatcgacaag tccgggagct gggcggccat ttaccaggat     240
atccgacatg aagccagtga cttcccatgt agagtggcca agcttcctaa gaacaaaaac     300
```

```
cgaaataggt acagagacgt cagtcccttt gaccatagtc ggattaaact acatcaagaa    360
gataatgact atatcaacgc tagtttgata aaaatggaag aagcccaaag gagttacatt    420
cttacccagg gcccttttgcc taacacatgc ggtcactttt gggagatggt gtgggagcag   480
aaaagcaggg gtgtcgtcat gctcaacaga gtgatggaga aaggttcgtt aaaatgcgca    540
caatactggc cacaaaaaga agaaaaagag atgatctttg aagacacaaa tttgaaatta    600
acattgatct ctgaagatat caagtcatat tatacagtgc gacagctaga attggaaaac    660
cttacaaccc aagaaactcg agagatctta catttccact ataccacatg gcctgacttt    720
ggagtccctg aatcaccagc ctcattcttg aactttcttt tcaaagtccg agagtcaggg    780
tcactcagcc cggagcacgg gcccgttgtg gtgcactgca gtgcaggcat cggcaggtct    840
ggaaccttct gtctggctga tacctgcctc ttgctgatgg acaagaggaa agacccttct    900
tccgttgata tcaagaaagt gctgttagaa atgaggaagt ttcggatggg gctgatccag    960
acagccgacc agctgcgctt ctcctacctg gctgtgatcg aaggtgccaa attcatcatg   1020
ggggactctt ccgtgcagga tcagtggaag gagctttccc acgaggacct ggagccccca   1080
cccgagcata tccccccacc tccccggcca cccaaacgaa tcctggagcc acacaatggg   1140
aaatgcaggg agttcttccc aaatcaccag tgggtgaagg aagagaccca ggaggataaa   1200
gactgcccca tcaaggaaga aaaaggaagc cccttaaatg ccgcacccta cggcatcgaa   1260
agcatgagtc aagacactga agttagaagt cgggtcgtgg ggggaagtct tcgaggtgcc   1320
caggctgcct ccccagccaa aggggagccg tcactgcccg agaaggacga ggaccatgca   1380
ctgagttact ggaagccctt cctggtcaac atgtgcgtgg ctacggtcct cacggccggc   1440
gcttacctct gctacaggtt cctgttcaac agcaacacat agcctgaccc tcctccactc   1500
cacctccacc cactgtccgc ctctgcccgc agagcccacg cccgactagc aggcatgccg   1560
cggtaggtaa gggccgccgg accgcgtaga gagccgggcc ccggacggac gttggttctg   1620
cactaaaacc catcttcccc ggatgtgtgt ctcaccccctc atccttttac ttttttgcccc   1680 ttccactttg agtaccaaat ccacaagcca tttttttgagg agagtgaaag agagtaccat   1740
gctggcggcg cagagggaag gggcctacac ccgtcttggg gctcgcccca cccagggctc   1800
cctcctggag catcccaggc gggcggcacg ccaacagccc cccccttgaa tctgcaggga   1860
gcaactctcc actccatatt tatttaaaca attttttccc caaaggcatc catagtgcac   1920
tagcattttc ttgaaccaat aatgtattaa aattttttga tgtcagcctt gcatcaaggg   1980
ctttatcaaa aagtacaata ataaatcctc aggtagtact gggaatggaa ggctttgcca   2040
tgggcctgct gcgtcagacc agtactggga aggaggacgg ttgtaagcag ttgttattta   2100
gtgatattgt gggtaacgtg agaagataga acaatgctat aatatataat gaacacgtgg   2160
gtatttaata agaaacatga tgtgagatta ctttgtcccg cttattctcc tccctgttat   2220
ctgctagatc tagttctcaa tcactgctcc cccgtgtgta ttagaatgca tgtaaggtct   2280
tcttgtgtcc tgatgaaaaa tatgtgcttg aaatgagaaa ctttgatctc tgcttactaa   2340 tgtgcccccat gtccaagtcc aacctgcctg tgcatgacct gatcattaca tggctgtggt   2400
tcctaagcct gttgctgaag tcattgtcgc tcagcaatag ggtgcagttt tccaggaata   2460
ggcatttgcc taattcctgg catgacactc tagtgacttc ctggtgaggc ccagcctgtc   2520
ctggtacagc agggtcttgc tgtaactcag acattccaag ggtatgggaa gccatattca   2580
cacctcacgc tctggacatg atttagggaa gcagggacac cccccgcccc ccacctttgg   2640
gatcagcctc cgccattcca agtcaacact cttcttgagc agaccgtgat ttggaagaga   2700
```

| | |
|---|---|
| ggcacctgct ggaaaccaca cttcttgaaa cagcctgggt gacggtcctt taggcagcct | 2760 |
| gccgccgtct ctgtcccggt tcaccttgcc gagagaggcg cgtctgcccc accctcaaac | 2820 |
| cctgtgggc ctgatggtgc tcacgactct tcctgcaaag ggaactgaag acctccacat | 2880 |
| taagtggctt tttaacatga aaaacacggc agctgtagct cccgagctac tctcttgcca | 2940 |
| gcattttcac attttgcctt tctcgtggta gaagccagta cagagaaatt ctgtggtggg | 3000 |
| aacattcgag gtgtcaccct gcagagctat ggtgaggtgt ggataaggct taggtgccag | 3060 |
| gctgtaagca ttctgagctg ggcttgttgt ttttaagtcc tgtatatgta tgtagtagtt | 3120 |
| tgggtgtgta tatatagtag catttcaaaa tggacgtact ggtttaacct cctatccttg | 3180 |
| gagagcagct ggctctccac cttgttacac attatgttag agaggtagcg agctgctctg | 3240 |
| ctatatgcct taagccaata tttactcatc aggtcattat tttttacaat ggccatggaa | 3300 |
| taaaccattt ttacaaaa | 3318 |

<210> SEQ ID NO 2
<211> LENGTH: 78001
<212> TYPE: DNA
<213> ORGANISM: Homo sapiens

<400> SEQUENCE: 2

| | |
|---|---|
| cagattccgg gtctcatccc tagaccaaag atatctgaat catttggcga tgggtccagg | 60 |
| aacctgcatt attcaacaca cttcccaggt gaccgtaaat gtcaaaagac aaaattacaa | 120 |
| caaacttaaa catcttaatt ggcttcattc atgattctag aatcgggcaa gacttcattc | 180 |
| ctcaaaatag cacaagtgtc ccaatgagct gagcagagga ggttggtttt atagacagaa | 240 |
| aagggctgaa aaaagcagaa acaaagaaca aaaagcagat tggtcatttc aaagttactt | 300 |
| tccttgtaag gcaggaacag ggaaacagaa caagagagaa ataactgatt ggtcgcatcg | 360 |
| ggttacttca ggttactttt tgttgtaagg attaaagcaa agggaacttc attatgttga | 420 |
| ttaaaacggt ctgcttggga aatcaggtg tgtatctctc ttctgatttt gtgaaaggtt | 480 |
| atcagtctga tgatgtagaa ctttagcatg agtgactcca ttttgatttt tagtctagtc | 540 |
| tgttgagacc ctaatgccag aacttttttt gtttgtttgt ttcgctcttg ttgcccaggc | 600 |
| tggagtgcag tggagctatc ttggctcact gcaacctctg cctccagggt tcaagcgatt | 660 |
| ctcctgcctc agcctcccaa gtagctggga ttacaggcat gcgccaccac gcccggctaa | 720 |
| ttttttttt tttttttttt tttagcagaa accgagtttc accatgttgg tcaggctggt | 780 |
| ctcggactct tgacctcagg tgatccacct gcgtcggtct cccaaagtgc tgggattaca | 840 |
| ggtgtgagcc accacaccca gcccttttt ttcaagacag ggtctctctc tgccacccaa | 900 |
| ggtggagtgc agtggcgcca aaacagctca ctgcagcttc cacctcctgg gctcaggtga | 960 |
| tcttcctgcc tcagcctccc cagcagctgg gccccaccac accggctaat tttttaactt | 1020 |
| ttagtagtga cgaggtctga ttctgttacc caggctggtc tggaactcct ggcctcaaga | 1080 |
| catccgcctg cctctgcctc ccaaagtgct gggattacag atgtaagcca ccgcgcctgg | 1140 |
| gctcctatga ttttttattta acataatgca ccatggaatt tgtgctctgc ttagttcagt | 1200 |
| ctgagcagga gttccttgat acttcgggaa acactgaaaa tcattccatc cccatccatt | 1260 |
| cattcctgca gcacccaagt ggaaattctg cgtttcagac agggacacta cccttagaga | 1320 |
| gcagtgggct tccccagcag cgtagtgaaa catgatactc ctgagtttca tgaaaaaagg | 1380 |
| gcagacatct ggccagagct gggaggcagg aaatagagca cggtgccctc ctcccatact | 1440 |
| ccagcttgga ttactgaggc tggggcccag gccctgcagg aaaggaggtg catgactact | 1500 |

```
ttaaggccac tcactctgtg actcaacggg ccgggtcggg gctggaactc aatgccctcc    1560
cgggcctgga gagcccacgc gccgtgggcg gggctcccgg ggtcgcctag gcaacaggcg    1620
cgcgccgcgc ccgagcccag agccccaaag cggaggaggg aacgcgcgct attagatatc    1680
tcgcggtgct ggggccactt ccctagcac cgcccccggc tcctcccgc ggaagtgctt     1740 gtcgaaattc tcgatcgctg attggtcctt ctgcttcagg ggcggagccc ctggcaggcg   1800
tgatgcgtag ttccggctgc cggttgacat gaagaagcag cagcggctag ggcggcggta   1860
gctgcagggg tcggggattg cagcgggcct cggggctaag agcgcgacgc ggcctagagc   1920
ggcagacggc gcagtgggcc gagaaggagg cgcagcagcc gccctggccc gtcatggaga   1980
tggaaaagga gttcgagcag atcgacaagt ccgggagctg ggcggccatt taccaggtgc   2040
gggagcgccc cggagcgtgg cgggcccttc gcttaggccg cttgaacatc ccctcagacc   2100
tccaggcccc agactccctc tgggtcttgc cctctgcctc gctcctactg cttgaggatt   2160
cgatgggaca gcgacgcact gcgtccccc acctttgtc cccggggcgg gcgtgtttct      2220
cgccgcagcg tcggagcccc cttcgatccc ccacctccct tctgttctcc agctcgggtg   2280
atctctcaag ccgggggacc gccggtcgt gctctcaacg cgaatccctc gcaccccgac    2340 cccgcccct gcctgtccac tctttgtccc ctggggtgat ttagcacccc cactatttcc    2400
ttttctggag tggaccacct cagactctct tcctttgtct ccctgggga aaaggttact    2460 cccccgtcc ctccttcaca tttcctttcc cctagtctca gtgtgcgtcg agtcccagag    2520
atgacagtcc cctttccct ttctgttcat tcatttattg gataggagtt ggcaagctta    2580
ttctgtgcta ggcaccgctt aggcattgga ggtggtgttt gctaatcagg acaggcaaga   2640
tcctagcctt agtggggcct agagtcgaat agggcaatca aacacaaaag caaataattt   2700
cagatagtga caggtgctgt gaagagaacg acttcctaac ggggtacagg gtgactgcat   2760
agaaggccgg ctgtcttaga gaaggggatc agggaaggcc tgtcaaagga ggagacattt   2820
gctttgtgag ctgaaccaag aggagcagaa agccgtgaga atatggggct aaagaacctt   2880
ctagccagga ggcctgcggt acccactcca ttggggccat gatattattc tttcaggcag   2940
ggactcagga aggttaacgt tttaaccctc tctaaaatag catcttcct caatgagcag    3000 cttagtcttt ggtcgtggca gagatgacct tgtcttagga gtcatctcct tgtgtgttaa   3060
aaagttagga aaggagggtt tctcatatat ctataaaaca agtagttaaa aacacaaaga   3120
gctcttcctt tcacaagcag ctgaataaga tacatactcc caattaaatg tcattgcggg   3180
ggttgttaag attaactaaa accacacttg cacagtatct taaataagcg atatacagaa    3240
tagagagatt ttgttacttg tgtaaaggga gacagcagat gattctgttt tcagcttata   3300
ggctcaaaag gcaaattgtg agatccatca gctgtagtat taaaatctat tttgagctcc   3360
gcttagaaag gaaaaaaggt ttaagcagtt ctttggtatg cttgactaac aaaagccttt   3420 tttttttggca gccttgattt tcatgtggat ttacatcaag cttatttgac aggattcttt  3480
ttatttggac tgtagtgtgt atattagttt ctgctagact aatatttcta accactgtaa   3540
tctatatact aataagtatg attgatcagt atataaaatt tgtatgccat atctggtctc   3600
tgaattagct gaatgaattc cataagggac tttgagactg tgtagacaaa ttttctgcat   3660
cagtttaatg cagtagagtc taaaatgtct ttaaatgaaa attgttggtc tgaagtgttg   3720
gagttgatta tgatacaccc catcacagtg gaagcattgt ggagagaagt cttttccact   3780
gaaattgact gagttgacaa caagaaatac gtattgtaac ttagttctta gttgaatttt   3840
atttcttaca attttaagcc agagtggggtt gacctgtcac ccaagcatgg ttaaaattgt   3900
```

```
attcagcatg caactagcat ggagtgtgtc agtcttcaat tcatttcctt cattgttctt    3960 aagttttttct gccacaatta aaccccacaa gttagtcaag gtgttgagat tttcactgct   4020
tcttaatgga ttgccacatt ccctgaggta gtttcttttg gtcttagaga attgtcaggg    4080
ccagcttttc tcacctccac tgtatggata tttttctttt ctaagatctt gaaatcagaa    4140
gcttttctcc taagtgtaaa agtagctctt tgtcatacaa ctgtagcgtt ttctgaaaca    4200
gagttcagat gaccttgagt ctaaagtggc taactttcca aggtgtgtat cgctttacca    4260
aaaccattat ttttcaagga ttcaaagaat gtgtttacaa ttgatagaaa atggaagttt    4320
aaaaaaatta atactttata gcatgttgaa atgagggcag ccttatacaa agtcatactt    4380
tgagcttgcc tagcctattg tgatcagaga ataatgtaat ttttgcttac aacttggtaa    4440
gcaggtcagt tattctaact tattttctga ttagaacaaa aagatgtaaa aacttgaaaa    4500
ctattgggaa aagaacaaag agtgaagagg acttttgagt gctgaggaat gtggcagctt    4560
ggaaaacaaa cttttaggc agagattctt tgctaggtca gtttgataaa gtgagcataa     4620
ccgtattttt aatctttaat gctaatgaat agcatagatg ctaataagca tctaggtcta    4680
taaaaagtca gctttgatag tgtatataga tggctttaaa cattgttttc tagcatttaa    4740
acactttcaa atcatccggt tgcttgattg ggcctagctg tctaagagga gagaatgagc    4800
ccagatgagg aaaagagatt gattttactg agctagaatg agaggagaga gggttgagtg    4860
aatgaaaaga atagctcatg tgctcccctc catctgtagt ttaagagggg ttgggtccgg    4920
tgttttgctt gttttctcgt ctgtaaattc tttgattctc tgacaccact cactatattt    4980
cattgtgaat gatttgattg tttcagataa aggggactgc aataatacct tgtgacatga    5040
aggcaagatt tattcatgtt agaggcaggc tttgtaaaat gggccactct tccaattgac    5100
atttgttttt atagctgttt tcattatgaa atacaatcta atgcctgact aggttaaaac    5160
catgttgtaa caatagttca ctaaaattcc ttactgatat acagcttatg ttgttatatt    5220
ccaaaaagat gaatattaaa atttgccaat aatgtttatt taaatactat tttcttcaga    5280
ggaaaaaaaa ctattttatg caaaggagaa agatctatac actatgactc acttcactta    5340
aaaaaaaaaa gactaacgga aatgacatgg agagactggg aagttctagt catcttgagt    5400
gacccattag atctaaatgt tcttgtttag ccctggtttg agtgaactaa atttaggtgt    5460
ctgatcagta ctttggaaat ggtgtaaatg cctttgtaat tgtctggact gatattagat    5520
taactgggag cacaagtaga aatagtgaag gaaagaactt tttgctattg ttatttgaca    5580
tcactggcat atttatagga atactttggt gttttttggaa gtaagtaaac caaccagtgg    5640
ttctaaaaag tcagctgggg gataatggta atgccgctgt tcttagctg caagttatct     5700 gccgttactt ctcctccatt ttgcatttta tcttgaatag ctcctcaaaa cctattaaaa    5760
tacctggtat tgaataatgt aattgaatgt gtactgaatt tcacagtgga aatgaataag    5820
aaatttcctg tggaggtttt ttgacttagc tactgaaata acggccttt gttgtgtgat     5880 tctttccctt ttctctttgt taaagaaaac tgtcttgtga tcttgtagat tacagaatcc    5940
ttttggcaat ttctgttcct agcactgctt tttcttctt tctttctttt aaatagaaat     6000
ggggttttgc tgtgttgccc aggttggtct tgaactcctg gcttcaagcg atcctcccac    6060
cttggcctcc tgaagttggg attgcaggcg tgagcaggta cttttttctga ggcctgcctg    6120 agcctatata tattttgcac aatttggcat tcctccctac agtgtttatg ctgatttgtt    6180
tctggtaaca actaatactg gcaaatcggc tgggcatgtt actttatgct gcccatattc    6240
aggaaaattg gaattctagc tgggtcattg ttcccagatg atgtagtttg gcaccagcca    6300
```

```
ttccatgttc acattttgag tatccaggag ggctggggac tttggagtag ttggtgattc    6360
cctctgccac atttcactgg ttggtcacta tggcatcctt tccaccacac tagtagtcta    6420
ggttctcaga tgttgcttat gagcctgcaa tggtttctag tttcacactg cagaaatgag    6480
tgaagccggt tacccgttaa tatggtccca tcatcactag agtaattcat tgttctaaaa    6540
ccagatctga gtctctcact cctctgcaac tacttctgat tctttcataa cacttgtaaa    6600
gtccaaactc ctctttagca tggcagccag cttccagtcc ttccctccta tgtggcttcc    6660
attctagcca gacaagaaag ggcagcgttc tccaaactca tcctcgccct tcattcctct    6720
ataccattgc tgagcacttt gttgaggatg cctctcccgt tcaatctagc ttgcatcttc    6780
cagctcgaat gtgtgcttcc ttgcaccaga gttttgttcc gtcacctgtg tgttttcata    6840
caagctggca catatctctt ctaaagccct gctgtcattg tagctgcgtc tttacaaaca    6900 ttttttttt aaattttat aaagtcaagg tctcactata ttgcccaggc tggtctcaaa    6960
ctcctgggct caagtgatcc tcctgccttg gcctcccaga gtgctgggat tataggtatg    7020
agacactgtg cccagctgta gctgctactt tatatcccag gtctatctcc aatggagccc    7080
aagcttcctg aggccacctg ttgtatcttt ctcattcatc ttgaagtcct ctgctcctgg    7140
cacagagtag gtacctaaca agagttggga ttgaattgat ggtcagtact ttgctagcct    7200
gatggtataa agatgtacaa aacatgttcc tggctcccac tctagggggg caatgatgga    7260
aacaaataga ttagcccaca ttagtaccaa tagtagaggt cactctggga gaaggccccc    7320
accacatttt gagtcatggc ctaatgaggt aatttagtat tgcctgctgc agtggctttg    7380
gaagaaaggc tggcattctt agccagtaga agctgatacc actgatttgt ttcacagaag    7440 cttaaatat aacaataaat ttgtgcttgg cctacggtga actttacagg caacttggag    7500
gtaatatgtt tgtctctcta agaattgttg aattcctctt ccctcatccc tcctgactgg    7560
ttctcacaag cctagcgggc cttttgcatgt ggttggttca taaatactt tttgattttg    7620 ggatataaaa tatagttctc cataaaataa cgactgttac caagtctttg atttttttt    7680 tcaaactata aatggtaatg acattctttg gcctttgatc agaccaccct taggggcaag    7740
agagtagttt catgttttgc ttttctagt gtcccctgtg tctgggtata gttgcagtct    7800
cagctgtcat actaacagtg ctgagtgagt cccttacttt cttttgggttt tggtttctcc    7860 cttgtaaaaa tgatcctgga ctaactgatc attaagttca ggtcaagtaa taaaaatcct    7920
taatgtactc acaaatacaa tttaatgttc ctgaataatc cttgtaaaaa ctgcagcagt    7980
tactcagttt tgtaaggtgt ggttgggtac tattaggctc aaaagtttat aggagctttg    8040
tgagtatagt taacaactca aaagaatggg gtgttttttc ccgaggggca tgaaatgttt    8100
ttgataaata gagttcattt gacttggtaa tgtggaaaat gagtagccct gacacgtacg    8160
ctatgctttt gcagtttttc tctcaagtag caattgggtg gcttttcctg taaaagatag    8220
aggaactgat tcttgagaat ttacgaaagc ttcaacccta actaggtatg caaagaatag    8280
ttgcccttta tgttgtaatt ttaggaagaa acctacatct ggtctaagtt tcatttgaat    8340
aatatgatag tttacacatc tgccatattt gagaagaaag tacctaagtc tccagcattt    8400
tagaaataat gctttacttt gtgtagaaat ggtctttaga gtttaatagc tgctgccctc    8460 tccttttca aagcagcttg acataatcat gagtatcttg ctgacagctt gtaaattttg    8520
attgtatgaa aactgaaaat aagaccattt cacatggaag attccctcct gccctgaaac    8580
agccaaagaa aactgtagcc atcaaatcta ttgatctctg ggctttggta caagtcacac    8640
tactacaaat aaaataatac caagtactta taaatgattt tcagtccttt taaagtttat    8700
```

-continued

| | | | | |
|---|---|---|---|---|
| tttttttaata | ttttttttga | gatggggtct | tgctgtgtcg | tccaggctgg agtgcagtgg | 8760 |
| cacaatcttg | gctcactgca | acctccacct | cctgggctca | agtgatcctc ccacctcagg | 8820 |
| ctcccaagta | gctgagacta | caggcatgtg | ccatcacgcc | cagctaattt ttgtatttt | 8880 |
| ttggagtaga | gatgggattt | tgctgtgttg | cccaggctgg | tcttgaactc ctgggcttaa | 8940 |
| gccatctgtc | tgcctcaggc | tcccaaagtg | ttgggattac | aggtgtgagc cactgtgccc | 9000 |
| ggcccagccc | ttttttaag | agaaaaacgt | atgacatcgt | tcgatttact gagtgcttat | 9060 |
| ggttttacta | aggcagtaag | gttttatgga | taccctatgg | taattagata gaattagtgc | 9120 |
| tctgaagtca | gctctgtaat | atggactcag | agtaaacatg | gcaaagggac acttaaggtc | 9180 |
| tgcattttct | ctgggaaata | aacgtattct | ttactactct | gaatctagtg ctgggaaatt | 9240 |
| ctaaatcctt | cttgaggatt | aaccacttga | agtaaagttt | tgggtcccaa gtaggcttgt | 9300 |
| gtccctgtct | ccttctcttt | acttttcaga | tgtttcttcc | tagagactga ggtatatttt | 9360 |
| acttttacag | atgaagaagg | aagcctcggc | tgtgtttgtg | gcttttgtgg gtgagcaaca | 9420 |
| tcacttgcaa | agataagatg | agcatagcaa | aactaggctt | tcaaaataat ttttaaaaat | 9480 |
| ttcttagtga | ttagaaaagg | aaaactcttc | ccttgtctct | gttaagaaac gttttcgac | 9540 |
| tttttccctt | tcttaatgga | tcttttattg | gcacttctct | tccttttgca gaatcttact | 9600 |
| taaaagtcac | tacgttacat | tacagcaaac | agcttagcta | atttttatcc agatgggccc | 9660 |
| cggttacagg | attgtacact | attgcgaatt | tcttacagga | aagtgaacat caagtaatta | 9720 |
| ttccaaatag | agttctctta | agaacgtgag | ttacttaaaa | atgtctaagg atgaagtcac | 9780 |
| ttctgaatat | aacttcactc | aagagaacaa | ataagcaaac | tgcatttagc ataacatggt | 9840 |
| aaattagctt | taactctcct | tgatgtttga | acatttgtcg | ctgttaacta ctgtttcact | 9900 |
| tttcaaatag | tcagggctta | gtttgcttct | gtaaggataa | agggaaaata cgccttcact | 9960 |
| gagtcataaa | tattttgtg | gctaacttt | gcacagagaa | aagaggcctc taagaaggta | 10020 |
| cccagtgaat | ttttttttcg | gggcagggag | agaatatgtc | atttttggt tgttgttgt | 10080 |
| tgttgtcatt | gttttgcttt | gttgttttta | ctctgaactg | aactgtatct tgacagcact | 10140 |
| tttgaattaa | gagcattact | cttattgttc | tctactacct | ggacgccacc tccctgttgc | 10200 |
| catagtgtta | aggatcatgc | tccgaggtgg | ggtgaggcag | aatggggcca agatcagaaa | 10260 |
| gttacattaa | gctacatcag | gtttatacaa | gcataaaacc | aaattttgg agcagtcccc | 10320 |
| agaatacaac | ctggtttagc | cacacctaaa | ggttgctctt | gaatattcct tgagaatcca | 10380 |
| catccctaga | atgctgggtt | tcaatgggcc | ctttatgtac | ctatcatggt gtcatttctg | 10440 |
| agcatttcta | atattccttt | catgtcttac | tgacagtttt | tcttgaataa atcttaggaa | 10500 |
| tattagtgcc | attatcagta | ttttgtttgg | tctgttcaca | ccacaaataa ctacccaggt | 10560 |
| ctgctacttg | cccctatttc | tctacctgct | aatgaaaatg | cttttgaaag tttgagtaac | 10620 |
| agtattggag | tgtgcacagt | ggtattggta | ggttctgtac | tcatccttaa ccacttgttt | 10680 |
| tcatcctttg | tgagcttgaa | gtttctccaa | aaaatttatc | acaaaactta tcagacatag | 10740 |
| ttaatacact | cagagagaga | atcactgaaa | aagtagatgt | agtttaacaa acccagtgcc | 10800 |
| tttttttac | ccatgaatac | atatttgtca | actaaacctc | attttgcaac ttgttccact | 10860 |
| actcgaatgg | taacaaactt | ttggtttccc | aatagatttg | gaagatgttg cttttgaaag | 10920 |
| taggaaatag | atggctttag | aagatgggaag | aatattttgt | ttgaagtggg agcgtggtat | 10980 |
| gtccttagct | gtctgtgaaa | tgcagctgaa | gatgggtgtg | ggccttcatc tgcatttccc | 11040 |
| atcttcagtt | tgaggaggta | gttaccttc | taaccactta | agaactgcat ggtacatgct | 11100 |

```
gttttattta caggcaaaa ctgtgctccc gtagtttccc tggtgcttgc cttcacgtta    11160
acacagtgtc atcgtttggc agtgtttatg tgccagggtc catgttagaa ggaggaaagg    11220
tatagcgaag ttaaagggtg cagttggcct cccacccttta gttttgtaag tgcctttaaa    11280
gtttgatttt tgtaggttga tcataaggaa gtgataagta tgttaggtta tttgtggttt    11340
gagctaattt tagtctcttt ttacagcttg cttttgtatcc tttgccatta aaacatgctt    11400
tctagaaaga caacttttga atgtaggaca cagtctatat tctatacttg gctacatttc    11460
aaaaaatatt ttctcagtac tttggaagtt ggacagttgg aagcatagtg acagtattta    11520
aaaatctttg attccggccg ggcatggtgg ctcacgcctg taatcccagc actttgggag    11580
gccgaggtgg gtggatcact tgaggtccgg agttcaggac cagcctgacc aacatggtga    11640
aaccctgtct ctactaaaaa tacaaaatta gccgagcgtg gtggtacatg cctgtaatcc    11700
cagctactca ggaggctgag gcaggagaat cgcttgaatc tgggaggcgg aggttgcatt    11760
gagccgagat cataccattg cactacagcc tggggacaa gagtgaaact ctgtctcaaa    11820
aaaaaaaaaa aaattaagtg atttctttgc tttgtgacac ttctactttt ccagcaagta    11880
aattatattc tttcatacag gtatgaaatt cttgttccaa gctagtggtt aaaaaggcac    11940
agttgatatt agaggatttg taaaagatta tgaccacgcc tgcaatgtac tgaagcaagg    12000
ctttgctggg ctgtgtatag gaaaccttcc ccagcctgtg cccttgcttg atagaacatt    12060
ttgctcctaa gggtaggtgc ctgtatctgt ctccagtact ggttagtttc acacagaaca    12120
gttgtgtttc agagctttag tctcaagctg ccctgctccc ctgaagcagc caccctgagc    12180
atgtgcactc acaggagggg acatgtgagg tcatggaaga agacgactca ggaagaagaa    12240
gacttggggt tgggttctga ctctgccttt gactgttgtg ggattttgag gagttgcata    12300
caggatctgt aaaatgtagt cattagacta gactagacag ccatatagca ttacctagat    12360
gtaactttct acaaagacat ggtcacagga gaagaccaga gggtggggtg atctttctgg    12420
aaaaattggg gcttcatgcc ttactcatgc tagatatggt agcattatat ggctgtgcct    12480 gatccccta atctaaaagt gggacagaac tttaaaattt catattaact caaattaaaa    12540
cttgaaaaaa acccattatt tccttaaaaa taataaaatg ccctgtgggg gcataagtca    12600
cattatattt taaaattcct gaatgccaca tggatgaatg tagttccttt tgaaattctt    12660
cttttgtcta aagaggaatg ttggattttg taattggact aaaaaatctt ccatttgaga    12720
gagaaacagt ctgctgcatg ttctaccctt gttcaggata aaacccacta atagctaaca    12780
tttattgaat tctgtgttgt gcctcaggca ctgtgcaaag tcctttacat gcaatgctgt    12840
ttattatata ctgtcaattg gtctataaca gcaggaaatg tttcaggagg acaatgaggt    12900
cccagaccct cagtcttctc ctgtgtcctg gattcagctt cacaatagca ctatggcagt    12960
gtggccactg cttcagcttc cacatacatg gctgtgaaga gagacagggg attgtgctaa    13020
gcctccccga tttattagga cataggagga gagagtttgt agttttttgac ctttgcctag    13080 ttttctaacc tctttcctag atgtcacaaa ttggccaccc acagtcatat tttgcttgct    13140
tcacgcaatg cttttttaaaa aagagaagag tttaatttgt gccattgttt ataaatgaat    13200
caggagaaat gacatgcaac tctggattct ggcctctctt gaaaaatctg aaaatcacac    13260
cgtctgagct tacactggca gtggtctgct ggactgaggg acacaactcc ttttggatgt    13320
acatgtgtgc gttgcagagt ttaccacagt cccacagtgg gtcacactgt ccttgtcggt    13380
gtacactacc tagcacttga gtttgcaacc cctaccccaa gctgagtttt ctcgtcaagc    13440
ttgatgttaa tgttatgtga tgcttggcct tgtaggtatt tggtatatta tcgttagata    13500
```

```
aaattgaagc aaagggctaa agggttggtg gcctgaggga gtgcccttga cagtaaagtc  13560
taggataaaa tcattggcca ggtactcctt cccttcccgc ccttcctctt ttctctttat  13620
cctcagcctc cttctgctat tttgaggaag ttagaagcca ccaccatttt ttcccacctc  13680
aggcaactga gtgtggctgt atttctgtcc catgttcagt tatttccagg aactattttt  13740
gatgaccaac ttgaagttac attgggtggg cctaatgggg gctgataaaa gaatgaggtg  13800
accaaatatg cttgcactga gacggctacg aagtaaggtt tttaatgact tgctttgtga  13860
cttggtcagg agtgatacca tttgtcatgt gtccaacttc atgactaaat ggttgctcta  13920
ccttatcctc atagctataa taaaataaaa taaatacata cattgcaggg aggaatgtat  13980
cttgttaaag gtctctccct tttagcaaca aaagtacata ttatgttgta gaacatgctt  14040
tttctttgat ccttcttgaa cacctattac tctatagagg tatgttgtgt atggcaaatt  14100
agaacaagca atagataagg atgattcttt accattataa cccagtcaag gtctttgtcc  14160
taagttttgt acctttctcc agagggaaag gtatttgtat ttatttattt attttttgagg  14220 cagagttttg ctcttgttgc ccaggctggg gtgcaatggc acgatctcag ctcactgtaa  14280
catccgcctc ccgagttcaa gtgattctcc tgcctcagcc tcccgagtag ctgggattac  14340
aggtgcctgc cacgatgccc ggctaatttt tttttttttt tttgtatttt tagtagagat  14400
ggggtttcat catgttggcc aggctggtct tgaactcctg acctcaggtg atccatccac  14460
ctcggcctcc caaagtgttg ggattacagg catcagccac tgcctccggc caggtatttg  14520 tattttagt ctctatgcct taccgtctca gatcaggagg atttggtgat ttatcgaatg  14580
tgggggaagg ggaagaagag gaaacgggag gaatgttcca gattagggaa atagctagat  14640
ggaagatgca gcccctcatc aaggtgggga cacaggaaaa ggaacgtgtg caaagaagat  14700
ggtgatctgg ttgtgaccat gttgttagag gacgtccagg gaagcatctg gtaggtggtg  14760
gggtgtttaa atatagaaca ttcggagaat gctccgaagc ttcagagaac ccttcccaaa  14820
aggacaaaac cagctcagtg ttttagcact ccgggatcat atggcatgac agcatggctg  14880
ctttatactt ttttgtgtat gtgaaattaa aaccaaccac tcaggaccaa tttctctgaa  14940 gcttttgtc aatctttcat ttgcttttct cgtctagatt gtaagctcct tgcagccagt  15000
gtctgttgat tcagtcattc aaaaaataat acatgaacag ctactaggta ccaggctctg  15060
tgctgggcag ttgggatatg tggtgaggaa gacaaacttg gtccctgccc ttaggaagtt  15120
cagtagtcca gcagacaaag tggctgaata aagataatct cagttcacag tgataagagc  15180
tcttacaggc ctaggctcca ggtgctgtgg ggatgctcag gaaaaggtat ctaattggga  15240
ttgggagcag gcaaaacaaa taaggatag tgtataaagg taatatctag ttgaagttct  15300
gaagggcaag gaggagtgag cctgtatatt ctctgagtct ctccctaatc tgggattgac  15360
ttcttgtccg tctctgttca tattaagtgt cacctaggct tgaaaggtg agatcatatt  15420 tcacttcctt cctctttggt cttaacctttt ctctgctacc ccctcacaca atgcatatgc  15480
attattctct tattgtatat attttttcctc tcttccttttt catgtttcct ctgccattac  15540
ttttaacctc gactgccata tggcctctaa acgcttccag aagggtagcc tagtggaggt  15600
tattccatca tggccttgag ctcatgcgac cagatagtga aggcatctgt gtaggtgtct  15660
tctccaggag ggtgatattt gtttcattgt aaattttgta gccctagaac accaacaaca  15720
gtgcacagta attagtaggc aggcagtaca ggattcattg aagtgaagtg ataaccttta  15780
tccaagtatg tatgcagata atctttgatt tgtacaaaaa aaattatatt ttaatatgta  15840
aagatttttt aaaagaatct tcaagtttta gccttcccac taggaatata ttgaaaacat  15900
```

```
gtgcctagtt cactgacttg cagctgccac tatgagaata aaggtctcat ttagttgttg   15960
tgaattttaa gggatatttt caatgatgtt ggctggttta tcccattatg tggtctttttt  16020
tttttttttt tttttttttt gaggtggagt ctcgctctgt cacccaggct ggagtgcagt   16080
ggcgcaatct cgactcactg caacctccgc ctcccgggtt caagcgattc tgctgtctca   16140
gcctcctaag tagctgggat tacaggcgcc tgccactacg cccagctaat ttttggtatt   16200
tttggtagag aagggtttca ccatgttggt caggctggtc tcgaactcct gacctcatga   16260
tccactcact tcagcctccc aaagtgctgg gattacaggc gtgagccacc atgcccagcc   16320
tatgtgctct tattagcaat tctcagtaca cagatagctt tgagtgattc tttcaagtca   16380
agtaccttat taaaaaactc aagtgtactg ataattatct tacttttaaa tggctaagtg   16440
ataagactga atttttaggt actgtaacac ttcagattac agattctgat attttatgg   16500
ttatttatat ttatttattt ttgagatgga gttttgctct tgctgcctag gctggagtgc   16560
aatggcacga tctcggctca ctgcaacctc cgcctcccag gttcaagcga ttctcctgcc   16620
tcagcctcct gagtagctgg gattacagtc acccgccact acagccggct aattttttgtt  16680
atttttaata gagacaatgt ttcaccatgt tggccaggt ggtctcgcac ttctgacctc    16740
tggcgatccg cccgcctcgg cctcccaaag tgctgggatt acaggcgtga gccaccgcac   16800
ctggcctggt tacttaaatt taaatacaaa aattatgttg attaattctg aatgatttcc   16860
tgattgctcc ccgtttacca ttcacacatt tattaaattc ttcgcttgcc atatagaagc   16920
agtctctctg ccatatatgc catatagata acagaactag ctgtctgcaa accactgaaa   16980
ttgtgaaaac atctccccctt ttttcctgtt tctaattcta gctatgagga ttatatacag   17040
aagtagtcct ggatttgatt tttttttttt tttgatgatt gttttttgat agttgttgac   17100
tacaaatcat ttaaacgtct gaaaggggaa aggttttcct taaaaatgga tgacaaagga    17160
gaataaaaag gtattttgac tatttttttg aatgatgagt tttttttttc tctttcttgt    17220
tttcttttgg agtcatttat gtgtcactga gtggatacca tggaacatgt ggcagaagta    17280
gatatatggg gtaaaagaac catagttcat aagctccttg acagaatcac tgaagtgtag    17340
ccgttatatg gccactgtcg cagggggagg cagcagtttt gaagaagggg atgagtaata    17400
atgagtgata aaaaggcatc ctggatagaa gaccaaactc tgcagaagac cccagtttga    17460
ttatgctttt gttttctgat ttgcggagga gagtgaaaat gcctgagggg tgcggggag     17520
cacatagggt gtatgtgtgt gtgtgtgcgc gtgcagattc tctctttcac tgtatgtatt    17580
tgtatgcatg tatgtatctt aggacttaag ctttctagtc aataaattgc catagtgggg    17640
aattgcttaa ttgcttgcct tctgttgttg tatttaattt aattttatt  ttaatgattt    17700
ttttggtggg gtacagggtc ttaactatgt tgtccaggct ggtcttgaac tcctaaactc    17760
aagtgatcct cccgcctcgg gctcccaaaa tgctgggatt acaggtgtga gccaccatgc    17820
ccagcttagt tgtattttaa atgggcctgt ttgcagcatt ccctactccc cttagtttac    17880
ctggctcaca acctgtcttt ccatatcaag gcttctgtca cccctggccc atgtcagtgc    17940
atttgggcag cccacccagc atcatcacct catgtcccag ggaacttcct gttcctctct    18000
tccagctatt tccttccctg gcagttgaga tagtctctac ctttgaccta ctgttaagct    18060
cagaccttct gctctctagt tacagcctct gtgctgccaa attccctcgc tcagttgctt    18120
tctctagttt gggttttctc ctttattcag atttccagct gtttctctcc tcccccacc    18180
gcagcctcct cacttccctc cttatgcatc tgagactgtg gtcagtcact ttagatgctg    18240
cctctccact gtacttgtgt ccatcttctt acctaccacc tctagccctg gagcaggctc   18300
```

```
ttcccctgtc tttgtcttcc tgggcccagg ctcctaagcg ctgctggaaa aaaaatcccc    18360
cagtattgag cccctagaaa tccagtcttt aatcccaaat ctgtctcccc cagcatctgg    18420
ccatcagatc taaagcttac ctgccatcct ttccacctca tttctctcac aggggaaaag    18480
gagcctttgc tcctagagtc tgcgctcctg accccttccc atctcacctg ttcaaggcat    18540
cttgcaataa ggggttggtg actctcgagg aatggatccc aggccctccc tattatcatc    18600
ttatgtatgc cagttcaacg ttctcagctt cctccagccg agacggcccc tccagccact    18660
gctttatact ctccttctct ggttgaaatt tttgaagtaa ataggtcact ctgcccatcg    18720
ttcatcttcc agtcactctg tgtgtttatc ttccagggaa gtgaggctct atgctaccaa    18780
gccactgaaa taatttttt ttttttccag actgagtctt gctctgtcac ccaggctgga    18840
gtgcagtgcc gcagtcttgg ctcactgcaa cctctgcctc ccggcttcag cgattctcc     18900 tgccccagcc tcctgagtag ctgggattac aggtgcctgt catcacgcct ggctaatttt    18960
ttgtattttt ggtagagatg gggcttcacc atgttggcca ggcttgttgg catgttgacc    19020
atgttggcca ggctagcctc aagtgatcca cccgtcagcc tcccaaagtg ctgagattac    19080
aggtgtgagc caccgcacct ggcctgaaat aattcttgac aagatctgct tccttgttac    19140
taatacagtg gatattttgc atcctaattt taatgcagtt cagtgtggta gacctgtatt    19200
tgcatattga atattccctt ccctgtttta ataactctat ttttccttt tcttttatat     19260 ctcctgcttc tctagctagt cctagacctt actcatcggt gtcttctctg tttgttcctc    19320
aacttgagga gttcctacag ggtttaccca atctgctgct tcatttagc ccttttgttc     19380 tttttgagcc atctcattca ctcacccagg atgtagcatc ggcccttgaa ttcagtgtgc    19440
acacatacac tgtgcactat gggacagcct tcagaggcac tttgttcctg aaattgtggt    19500
ggtctttgcc tctcatggag ccttgcatat gctgtttcct ctgcctggaa tatcctacct    19560
tttacttaac tgattctcgt tcttctttcc agtcacattt tgtacatttc ttctgggaag    19620 cttctctga tttccccttt ccacaggtcc aagttaactg ccttgtctag gtcctcccat     19680
ggccctctga aggcctcctt tcatagcacc atgtctgagt atactgtaat aacacgcatt    19740
gctctgtaat agcctgttta cttacctatt gccaagtaat ctatcaagtc ttataaaggg    19800
cggggctgct tttgttctag tcatttgtat ctcttagtac ccaatatagt gtttggcata    19860
tagaaaatac ccaacaaggc cagtcgcagt ggctcatacc tgtaatccga gcactttggt    19920
aggctgaggt gggcggatca cttgaggtca ggagtttgag accagcctgg ccaacatggt    19980
gaaaccctgt ctctactaaa aatacaaaaa ttagccaggc gtggtggcgg gtgcctgtag    20040
tcccagctac ttgggaggct gaggcaggag aatcacttga actggggagg tggaggttgc    20100
agtgagctga gatcactcca ctgcactcca gcctgggtga cagagtgaga ctccatctta    20160
aaaaaaaaaa agactccatc ttaaaaaaaa aaaaaagaa aaagaaaga aaatacccaa      20220 taagtagttc ctgaatgaat agatgagaat gctgtttaga aggttcatga attggaaacc    20280
gtgattgcta gggaggcttt gagttgatgg tattgtgttg aaccatgtgt tacccaggat    20340
caatttagat tttacacttt gttttctctg ttccttttta tagtaatttt ctgtatgtgg    20400
tgttttcccc ccatgagatt gtataccatt tctcagcgag aactgtgtgt aatgcttggt    20460
ggctccctca tggtgccttg catggaattg gacttcgttt cagtggatct gatcccagtt    20520
atgttaatgc tcgatggagc taagtcttat ctcgaagcag tccatgtctt catcagctgg    20580
ccctgcctca atgccctgca cagaccatgc cactctggag aggtagtttc cctgtggctt    20640
attagtctta tgttccagtg tgctggccaa gtatgagaga catcagtggt atgagagagt    20700
```

```
ctctctcatt caaacttcgt aggttttgta gctgggactg accagtgctg acaggaaata   20760
gaggcattta ttaaaagcca gagattttc aagttgcagg aagcaaagct cttgttagct    20820
atgattttgt ggtgggtttg gtagtccaat ataaaagtaa aaactggatg acaatgggag   20880
gagcatgctt gggtctccaa agttagatca ttttcctaa gtaatttgtc tttaaacttt    20940
tactggtttg gaatttcctg agatttgat cttgccagaa agtttatagc aaaagttctg    21000
agcagatgac acttttgcgt ctgaaaccaa atcattgttt ttgttttaa ctttttcttt    21060 aatatattat ccttagttca gccctgaaga ttattctgtt atttgtggat ctcaactttc   21120
cccccatctc ctggatcttt gtgaaatgaa tggtattaat tgaatagaga aggaagatat   21180
aaacataaac ttagtcaaaa acttgttctt gactaggcaa gttgggcttt atagctttga   21240
gctgatgaca tgtctattct tgtgaaaaag ggattttag tgttggtttg gcttcttgtt    21300
atatttgatt tattattatt atcattatca ttatttttga gacagagtct tgctctgtcg   21360
cccaggctgg agtgcagtgg ctcaatctcg gctcagtgca acctccgcct cccaggttca   21420
agcgattctc gtgcctcagc ctctggagta gctgggatta caggcgggtg ccactacacc   21480
tggctaatat ttgtattttt agtagagaca ggtttcacca tgttggctag ctggtcttg    21540 aactcctgac ctcaggtgat ccacctgcct tggcctccca agtgctggg attacaggcc    21600 ttagccactg tgcctggctg attttttttt ttttttttt tttaggtttg ttttaactgg    21660
aactttacgt gaatgtaatt gaatttagaa taaaagcact taatttcaca gtgtgcagtg   21720
aactttctgt tacttatttt aacagtaaaa cccttgcag taaatgactt ggagcaaaga    21780 ttgcttttt aaaaaatgtt ttaatttgtt tttcttttct tgagatggag tcttgctctg    21840
tcaccaggct ggagtatggt ggcgcgatct tggctcactg cagccccc gcctcctagg     21900 ttcaagcgaa tctcctgcct cagcctcctg agtagctggg actacaggca catgccacca   21960
tgcccagcta attttgtat ttttagtaga cacagggttt caccatgttg gtcaggatgg     22020
tcttgatctc ttgacccgt gatccaccct cctcggcctc ccaaagtgct gggattacaa    22080
ctgctgggat tacaagtgct gggattacaa gcgtgagcca ccacgcctgg ccaatttttt   22140
tttttttttt cttttgaga cagagtttca ctctgtcacc caggctggag tgcagtgtca    22200
cagtcaaaac tcactggcag ccttaacctc ctgggctcga atgatcctcc tgcctcagcc   22260
tcccaagtaa ctgagactac aggcatgtac cactgtgccc agctaattgt ttttttattt   22320 tttattttt gtagggacag ggtctcgcta ttttgcccag gctagtctac aactcttggg    22380
ctcaagcagt cctcctgcct tgacctccca aaatgttggg attacaggga caagccactg   22440
cacctggcca aggattgttt tttaagtgaa ctgagaccca gccttattag tggtcccaga   22500
gcagacctgg gacctgaagg gaacccttt cttctggtcc agcgtctttc ctctgatggg    22560
ctactttcct ggagcctttg attgcctgtc atcagagtaa ctgagtttga acagagtagg   22620
tagttcctct ccagaccacc acactcacca gctttcattc tgcttctctc gtttagactg   22680
tggttctgaa tcctcagttc tatttactga gtgttttaa acataaaaat gccttttaat    22740
gagattgaag gccagaggtg ggacagttga ggacaaagta gaaataaaac cttcaaggcg   22800
gggttgttgg tgggagtctt ttttgttg tttgtttttt gagactgagt ctcgctctgt     22860
cacccaggct ggagtgcagt ggcacaatct cagctcactg caacctccgc ctcccgagtt   22920
caagctattc tcctgcctca gcctccttag tagctgggat ttcaggctcc gccaccatg    22980 cccagctaat ttttgtattt ttggtagaaa cggggtttca ccatgttggc caggctggtc   23040
tcaaactcct gacctcaggt gatctgtctg cctcagcctc ccaaagtgct gggattacag   23100
```

```
gcgtgagcca ctgtgcctgg cagggagtct tatagaagct gtcgtggaca atgtgggaag   23160
tagtgagcct ttgtattcca gtatgctggg ctccactgtg cttgctctgg cccccggtcg   23220
ctctctgtgt gttattgagt ccccatccac ggccatactc ttcgtcctgc ttctctcctt   23280
accatcctct ccccgctagt ggtaccacgg ctaccactag caattactga catgtgggat   23340
cttagggcta cttccctata aggctgcagg gcatgtggtg ttggctacgc gcatggtaac   23400
catggtagcc ctgtggttct ccacatgtgc gccttgtgac ctgggattgg ctgcagacta   23460
gtaataaact gcgtcttctg gtatggaatc tgtctgtagt tgtactttct acctctgtat   23520
ttaaggggag atctgtaacc taccaatgcc agttgaagag gatggatgat agagatgtta   23580
acaaacagct gaaaaactaa ctacaatggc ctgcaaaata gaacagcagg tttttgtggc   23640
aaaactttgt gtccatgagt ttgttttta aatatcctca tataatctgt tttaaatcga   23700
gaggctttgg gtaaaagcca tggctagtct tacatgtcat ggagtaccta gcttgtgagg   23760
ttcacagttt attatttaca gagtgtcccc ttaaatcttc tttgggtcgg ttcagcgaat   23820
gttgctcaga tggactttt tggctgacat agagtcaaaa tggtaatcaa gcatgaaagt   23880
acagacagtc cttaacgcac aaatgtgtca tgcttgaaaa gttggaaagt tggttctctg   23940
gagctctgat tgtattgtcc tgtagaatcc gtgttgtgaa tggtggttaa atcccaaatg   24000
agtccgtaga acctatataa tctgcaatat acctgcagta ttccaattaa tatgtaattc   24060
ccccatagaa ctatgttaat gatttgtatg tatggtattt aatattatac ataataatga   24120
ttgtatgaat aaaaaacatt ctgggctcca tgtggatgat ggggtgtgtg tgtgtgtctg   24180
tctatgtgtg ggtgggtgtg tgttcataga tccctttttcc tgcaatcctg gcactggaat   24240
tggttttatc atttccaatt aagtttcatt cccatgaatt ttggagtaca gactgggtcc   24300
aggtatgcag ggcatagatt agagccctga gaaataggat taggctggaa ttgctgggtt   24360
ggagatcagt agcttccagg aacactttt gggcctggct gtcttcatta tccccttttg   24420
ttttctcctg gggtctgcag gtattgccct gttttgttcc tctaatatca cttttttttt   24480
ttttctgctt ttgaccaggg ttttgcctc tggtctacaa ctgaatatcc tatcagactc   24540
tcctgatttt gaaataaata tatagttttt ttgaggtgtt ctagcgaatt tctaaatcta   24600
aatgttgtgg cagagttatt acatactaat tttgctatga gaggttgtag atcccagat   24660 gactaatctt gtaaaccata cacgcatttc catctaattc tccattgtat atcatgttgc   24720
agaaaataac agcctctaga gtttacattg cctcctttga ctatatttct tatttaagat   24780
tagttttcag ataagacctt ttcatggcag tacataactg tacagagggc ttccaacttg   24840
tcttgggagc tctcatctct gggagacatc acattaccca ctgcccctg ccccccgccc   24900 ccagcctgga tgcactcagc ctgtaccca tttctgtcct cagccaaaca ctgctgaaat   24960
gcaagagctt tcaattgcta gccagtgaag atgcagacta agggattcc atgtagaagc   25020 ccgctctttt cagctggctc gtcgagagct ggaggcccct tgcttgttca catgaggctt   25080
tttgtccctg acttggtggc tgctgtttca cttctcagca gaaagggaca cccttgcccc   25140
cccccagaaa ggaagatttg atgtaccact tccgaaaggt tcagtcgggc atcactgtaa   25200
ccaagaagat aggtcaggtg aggctggagg tggaacaggg ctgctcgcta gaactccaga   25260
ttgttccaca agtgccttct ggcagagaat gatggaagct tccgtgattt ttttttctcc   25320
ttaatagtta tgagcacaga agaggagcag attgtctggc tatagaagct gtcttatttt   25380 ttattttgt ttttgagatg gagtctttct ctcttgccca ggctaaagtg caatggcgcg   25440
atctcggctc actgcaacct ccgcctcccg agttcaagcg attctcctgc ctcagcctcc   25500
```

```
tgagtagctg ggaattacag gcatgcgcca ccatgccaga ctgattttg tattagagac   25560 agggtttcac catgttggtc agtctggttt cgaactcctg acctcaagat ctgcccacct   25620
cagcctccca aagtgttggg attacaggtg ttagccactg cacccggccg aagctgtcat   25680
attaaatagc actttctgct tttagcaaat ttaatccaaa tgagacttta gattttcttg   25740
ctctgactta ccagcagttc cttgaaacac atttaattat ttttgccaga aaatcactca   25800
agcacttacg ccatttttt accgtgaaaa tatgctgcat tattttaaaa tatattagaa   25860
gtcagtaacc ataagatttt atatgttttc taatgtattc tgtaagcttt ctgctgcttt   25920
tgtttggaag gtgtattttg taacgtagag gactgcttta tctgcttgta agcttgattt   25980 ttgttttac tgtaattttt ttttcttttg ctgtattgag aaatacattg agtaattata   26040
aagtcagtgg catgtttata agttaatatt tgtatctatt ccttagttac tctaactcaa   26100
aacctaaagt aatcttcaac tctaatttac tctgacatcc agttgactgc caagtcctcc   26160
aacttaatcc ttatcctttt tttttaaag agatgcagtc ttgctttgtc acccaggctg   26220
gagtgcagtg gtgcaatcat agcttactgt aacctcaaat tcctgggctc aaatgatcct   26280
cccacgtcag cctctggagt agctgggct acaggtctt gctaccatgc ccagctaact   26340 ttttatttt atttttata gagacagagt ctcactgttg ctcaggctgg ccttgaactc   26400
ctgccttcag gcggaactcc tgccttcagg cggtcctcct gcattggcct cccaaagtgc   26460
tggaattaca ggcccaattt tattcttggg atgtatgtct gaaactcttt ccttcacttc   26520
cttcccaagc cttagttcag gcccttctca tctgtggtct tcaaagtcgc cttcagctgg   26580
ttcaggtcct tcctttctgc tgtatctttc atgggaggac atgttatgta tcactgtcct   26640
acttgaaaac ttccattccc cattgatgag ggtgttacct ccagattcct aacacaggtg   26700
ctgaaggcat gcctggataa aggcactccc ttgatctcct ggccaggtcc ccgtacacct   26760
gcagcgcatg ctccacattc tgtctttact gatgctgtgt cttctgcctg cggagccacc   26820
caccattcta ttcacagccc ctgcctcagc ggagcacgtg cctccctctt cctacactga   26880
gctgtccttt ctattgaatc ccctcttttt tgtagtatgg gaaatatttt attatgaata   26940
ctcttttctc tgttgcctcc gtgaccacgt taactttgcc ctaattcgcc ttaggactcc   27000
atctgcttag gggaaagtta ggatttggtt acagaaagca agctgctaga aagaacagtg   27060
tttagcttct gacaggcaaa ataggatttt gcaacatgct tttccttttt aatgcttaga   27120
cattttatat gaattaatat ttttatttgg ttgcttatac attactttct ttttagctag   27180
aatgtgaacc ctataggaac atggggattg cctttcacat cttttgtatcc tcagtaccta   27240 atgttcagtc accctgtggt cttgtgtcgt atatacattt agccttcctt aattaaacca   27300
tatgtactgg tccccgtccc ccacccccaa atagagagaa agaaattcct tgaatactac   27360
attgccagta tcaaaccaca ccttgatatc ctctggggaa agggaggtat cagttgaaaa   27420
gagaaaagag gttaaaatct aggcattaaa atgtgtaagg cttagatgct ggcaatttaa   27480
ggtatgtttt cctgaggtta attttgattg tgtgcaaatt ttacctcata tctaactgta   27540
ggatttagtc accacataag atgggatacc tccataaatc cttcagaaat gtttgtgaaa   27600
ttaaataaag ccttattgaa gactcagctc ttgagagtca tctacctacc taacagttat   27660
tcttgaacag aagagtctta ctttttcccta taaggcagtg tgatagccat ctgtatattc   27720
atataattta tgttggcgct tacttcattt aaaaatgtat tccgtgaatg cagttgccag   27780
gcggtgtgct gatcagaaac gtgtaccaat ggcctctttt ataattataa gaggaagacc   27840
aacctgaaac agtcacacaa atgattaatt ttaattgtgg aggagtgctg ggaaagaaaa   27900
```

```
ataaaagatg caatgcaagt gtttacaaag gagctttgag cttgtttgaa gtggtccttg   27960
ggcacttaag caaggcttaa agaatgatgt gattagaagt ggcttagcaa ttctaaagaa   28020
cacagggaag gcgtgtggcc agaacattgg tccctagagc acatcgcctc ctgacatacc   28080
atttccttaa gttaatgttt taccactata cataggccct ccccttttgtt tacccagatt   28140 tttttaattt taaggatgtt tttaataact tagaatcctg taatttgttg aacagtcctg   28200
tattcccttt acttatattc cttgagattt tataaaatat tttttacatg tcccaagtct   28260
tgattatatc tttttacctc ttgttaagaa atacttactt ttctattttt atgctatatt   28320
tcatgtttac tgtagaaaac aaaaaaagta aattttttct ttattcctat cactgcagct   28380
tataagcact ctaaacattt tgatctatat tttgccaatc atatatttta gttaaaattg   28440
ttgttgacat aattgtagat tcctgtgcag ttgaaagaaa taatacagag ctgagcgcgg   28500
tggctcacgc ctgtaatccc agcactttgg gaggccgagg caggcagatc atgaggtcag   28560
gagtttgaga ccagactggc caacatggcg aaaccctgtc tctactaaaa atacaaaaat   28620
tagctgggtg tggtggcggg cacctgtaat cccagctagt tgggaggctg aggcaggaga   28680
atcgtttgaa ctccggaggc agaggttgca gtgagccgag atggtaccat tccactccag   28740
cctgggcaac aagagcaaga ctgcatctca aaaataataa taataataat aaataaactt   28800
taaaataaaa acagagagat cccatgtgcg ctttgcctag ttcccccatc cactgcccat   28860
aacattttgc agaactgcag tacagtatca caaccacaat actgacattg atacagtctg   28920
ctcatcttat tcatatttcc ccagtgttac tcgtatccac gtgtgtatgc attgtgtttt   28980
caatactctt ttattataaa gctgttttta atgtgattca attctaggtt gttttgttct   29040
gccctcaaaa agcattccct ctcctaatca tatctccgtc ataccttgt atgttttctt   29100 taaacctgtt ttaagaaagc agctacctgt aagagaaatg agattgaaaa cagaattgcc   29160
aatctgcttg tactttataa gcctgttgat tgtttagata cggtttagcc agtttatagt   29220
taccctgggt gctgaaaggt atgctggatg atacctaacc aacagagaac cattgaatgc   29280
cgttcaaaat ggactgaagc atcagcaatg tctgaaaaag gcctgacagt aatgtacatg   29340
tcaaatggcc cgtaatttaa gcagagtaga gtaagtagaa gaataaacat ggggaaagtt   29400
ccagcaacag aggaggcttt gagcttttgc tcttcatctt gagtggatgt tgttctcagg   29460
tggtaatagg ccatcgagct ttctccactg gctgcctctc tggggaacaa ataaccgaaa   29520
agatactcag caccctggtt ggtacatagg tggtcagttg atttatactt cctggttttc   29580
agtgttgctt gaattttcta aatggaaaca cagtaccttt ataatcagaa aacaatcccg   29640
agttttgatt tgagggtgtt gtaaaaagtt aaaaaaaaaa aaacagaaat gtgaaaagga   29700
agttgtgtta gagtatttgg agttgagaaa gcatgaaaag gacagaagag aagctggttg   29760
tcaggttgca tggggtagct acaagcacac tgaccagaaa gtcagctgga aaaaaaatgt   29820
agaaacagga gataaaacgg ccaagggct atacaagcaa acagcaagga cctgagaaga   29880
aaaactagtt aggtgtgact gtcagagtga tgtgtacagt gtgatccttt ctgtgtaaaa   29940
acaagcagta agaattcgct gtttacgttt gcgtgtgttt ggagaagagt ggggaagagt   30000
aggcactgcc agactgtgaa cactggttag gttattgtta tatctttgta ttatatacac   30060
tggacatgtt atttgtataa tatgagaaga aattttataa atcattaaat cttttggcat   30120
ttaggaacat ttgtgttttc taatagttgc ttctatacta ttatctttat tatatgccct   30180
tcatcttctc agtgtttggc tgttgttgtg attccctttt gtgagcagtg ttgaagttag   30240
ctaatattca tttcttctcc cttctttcac cctcctccag agtctgattt gaagtattcc   30300
```

```
tagctgctac ctataaaagc aataagcaag attgttttac ttttcacaaa ctcgtcctgt   30360
tctgtgcctc tgcctcggac atagctgtag tatagagtgt tgtctcccctt acatccttct   30420 atcttagacc tactagtaaa tattaatgct cactctaagt tcttctcaat tcttttttt    30480 tttttttttt ttttttttga gaaagagttt cgctcttgtt gcccaggctg gagtgcaacg   30540
gcacgattct ggctcaccgc aacctccacc ttctgggttt aagcgactct cctgcctcag   30600
cctcctgagt agctgggatt acagtcacgt gccaccaccc ctggcaaatt ttgtattttt   30660
agtagagaca aggtttcttc catgttggcc aggctggtct caaactcccg acctcaggtg   30720
atccacctgc ctcagccttc caaagtgctg ggattccagg cgtgagccac cgcgcccagc   30780
ctcttctctc aattcttcct gaagctcttt ctgcactaga ttcctcagga agggcttgtg   30840
ggaacaatct tctgtgaatc aacagtacat attcataata gtttgtcagc agcctattat   30900
tttaaggcca tttggtctgt atataaaaat gtttggatca cattttcttt ctttaaggta   30960
aatatgttat tctgttgtct tctggtataa agcattgctg taaatgtttg acagtctaat   31020
tatcttttgc ttataagtga cttagggttt tttgtctatg tgcccaaagg attttttccc   31080
tctttctctc ttttttttt ttttttttt ttttaaaca gacaggatct cacccctgttg   31140 cccaggcttt agtgcagtga ggcagtcaga gcttactgaa gttttgaact cctgggcttg   31200
aggaacaaag gattttttta accttttaat tcaaagtctc atcatttatg caaccatgtc   31260
ttggtgttgg ctgttttggg ttgttctccc tcaaaaatcc atgtgctctt tcaatatgta   31320
gttttaaatc ttttttttt aatttcagga aaatcttgaa ttagagtttt ccgttttcg    31380 tctggtacat tgcttgggtt tccttcttca ggaactcagc ctgttatgtg tatgtttgat   31440
cttctttgcc tgtcgtctgt ttctttcact tcctctcact tttttaaact tcatttatta   31500
aaaaaaaatt tttttttcga gacagagttt cgctcttgtt gcccaggctg gagtgcaatg   31560
gcgtgatctc ggctcactgc aacctccgcc tcccaggttc aagtgattct cctgcctcag   31620
tctcccaagt agctgggatt acaggcatgc gccaccacgc ccagctaatt ttttgtattt   31680
ttagtagaga cagggtttct ccatgttggt caggctggtc ttgaactcct gacctcgtga   31740
tctgcccgcc tcagcctccc aaagtgctgg gattacaggc gtgagccact gtgcccagcc   31800
ttattaaaaa tttaaaaac atacatttaa acttaacaga aaaattatga gagagaaggg   31860
ggtggtgcca ggctttttta aacaaccagc tcttacatga actcatagag tgataactca   31920
ttaccatgag gacggcatca agccgttcat gaaggatctg gccccgtgac ccagacacct   31980
cctactaggt ccatttttaa cattggggat cacatttcaa cgtgagattt ggagggggca   32040
aaactacaaa ccatgtcact cagggattgg aggagcaagt accacctata ctttggactc   32100
aggtagaaag gcaaaatatc caggaaataa gctgctaccg tccagggttc agcagaggtg   32160
cccatcagcc tgccaagtac tcaagagtcc agcctctagg gagctaatca tcatggtgag   32220
ctcttcgagg cacagggagc tgggaagaca gtgcttgcca cccctgcctg aatagtgttt   32280
gcacagagag ttctgttgtg tcttgattgg gtcctcctgc cactgggaat gctgtggatt   32340
atactaggtc tctatctggc ttgtttcagg ctccatgtg aaaaccttct tgatatccta    32400
gccatccacc tgctcagtcc ctagtttgca aggaggctgt ggggagccta gattctgtgt   32460
cagatagaat gtactacatt ccgtctcagg aatgtaccac atcagaaaac agtgcgacct   32520
gcaggagaag tagaggtgaa gaggcacatt cttccgagaa atgtttctct caacacccag   32580
cattccctgg atatcagcag gaaattactc actgctagaa aatgccccat gagccttctg   32640
ttaaggaggt caagggagag aacagagaaa gttctcaaag ttgacttggt cactggtact   32700
```

```
ttcttatgcg gttcttattt tgtttgccat cgtcatcatc atgctatgtc tattttctca   32760
atccaaatcc actgctttca ccttggttct ttctgaccgg tttggcacac tcattcagta   32820
aatccttatg gagagcccaa tgtctgcata attgtgctgt gctgatgacc aagctagacc   32880
tacgagtgtc ggctcctttg agatgtacgg gacagctctt ctgtcatctc ttctgggaag   32940
cctctccagg cttggtgaac agtggcaaga tgtttaacag ttgtacatgt gtcccatgtt   33000
cctttctaag agcctgggca aaccagaccc ggtcgcaggt catcgtagta tggcgtgagc   33060
ttcctctctc ctttctgacc tttttgtgtga tggcaagaac ctgcagagtg acacaagcag   33120
caggcttctg aggttgctct agcctcagaa tggccgtccc ttctccaccc tggccctcat   33180
tgctgaggtt tcctttgaag caacagtgcc ggaacagact aggggaagca gcttggacat   33240
agctgtatga tttattacca cccattgagg ccaaccaaag tcggcaagga gaggtagcag   33300
gtcagtggtg cctggaagct tcctctttcc tttgcaccag atgtgactgc tctgcaatta   33360
ctcctaaatt tgctactctc gttttttacta gccaaccttg atgtttttcc cttcttcctg   33420
tagaatagac ttcccctctg atcagtactt tctactcaac actatttgtg gccacagtgg   33480
gaactcattg aggacaggga ccatgacatt actacctgac ccatcaacac ttggcataac   33540
ttgaaatgca aggacaaaaa ttggctgcaa gtacaatgtg gtcttcactc tgaaggtgat   33600
ccttaaaact tggcttttggc atcatattgc cttaatatac ctaggggatt gggtaaaacc   33660
agttacttta aaagagtttt acaattctgg ccttctagct atcttgtctt cttaaacaag   33720
agcacaagat gaatgtatct tagtgaaatt ttatatggtt tgctttgagt aatcttgcga   33780
agattgattt ttagcacagt aggaaagaca cattctaata gtgattttt tccccgagtt   33840
tatgtactgc tgttgcatga aaatctgact agatttaatg ttcctaaagt tctttgttca   33900
tcctgatttt tgcaggtcct agggaaagct ttgttttcct cttaacctaa cttagatgtt   33960
gtcatttcat gagctttgga ggaagagtgt atagccaatt gtgtaatgtc tttaaaggat   34020
attatctctg caatagttgt ttataaggcc taagttattc atgtaataat agtggccccg   34080
gatctgtttc tagcaatagg tatatggatt ttggttccta tatagttgta gttgtggctt   34140
tgagatattg agcaagccct tttaagaaag gatttggcat ccctcagcct tcaaaagctt   34200
ctcaaaattg atcatatgtt attagcaaag gtttactgcc tgcttccatt gtatagacaa   34260
tttatttttt atgtattccg ttctaagaag gcagatgacc aaaagatctt gcatctgttg   34320
cccaaggctt gtgactagag aggaaagaga taagaatact ttttttaaaat cccatttttac   34380
taaatatgtt gaggaagtgg taagatatat taatttgttg agatttttct gttatgccta   34440
ttatatgaaa taggtactct gaacatggct tcttaattaa atatatttga taaaatacaa   34500
cttgcttccc ctggagttta gaagtcagat aactgccatg gagagctatg ctttctttgt   34560
tttaaagatc tgcttatgaa catgataaac aggaacaatt taatgttttc aatattttct   34620
tgtattttac tgcaagttta tacacaacat aaatatgggg gaaggggggaa atgtttatac   34680
cagagccatc ctgcccattc tttccttaca gaaggacaaa ggagcagtat ttatttttaac   34740
tacaaaaata ctattgtagg ttttaaaaat tccgtatatt ttgatatctt gtgttcctct   34800
tgacctttaa tttgctaaat agttgcaaag aatgaaggta acctgcatca tcttcttaaa   34860
aaccaactct atctaattat aatagttgt ctatctctga aaaatagtga tgtgttcatt   34920
ctgaaatcag aactaccgga tgcagctgca ttttgttact atttgaattt cgggagaggg   34980
aggaggatgc agcctttcga gctgctgaaa tacacaaaca caagaagac accaagcata   35040
gtagaactgt gttaagctga ccaagccaga agaagcacct attctcagca tagtatgaga   35100
```

```
cgtaaaggca atataatggg catagttgaa gatggtagaa ggaaaataga ctctgatggt    35160
ttaatgttaa atgctttttt taaaaaagtg gtattccaat atcgaagaag aagactttct    35220
acttttagaa gcaataaagg aaattgcaga ggaaagggtc aataggttgg aatacataaa    35280
aattaaaaac ttttaaactt ttttttttg agacagagtc tcactctgtc acccaggctg    35340
gagtgcaatg gtgcaatctc ggctcgctac aacctccgct tcctgagttc aagcaattct    35400
cctgcctcag cctcccgagt agctgggatt acaggcatgg gccaccactc ctggctaata    35460
tttgtatttt tagtagagac agggtttcac catgttgtcc aggctgatct caaactcctg    35520
acctcgtgat ccgcctgcct cggcctccca aagtgctggg attacaggca tgagccaccg    35580
cgcctggact aaattgtttc agtattaatt ttttttaaaa caagatctta ctgttgccca    35640
ggctgaagta cagtggccca atcatggcta actgcagcct tgacttctgg gcctcaaggg    35700
atcctcccac ctcagcgtcc cgagtagctg ggaccacaga catgtaccac cacacccagc    35760
tacttgtttt atttttattt ttgtagagat gaggtttcac catgttgccc aggctggtct    35820
cgaactcctg ggcccaagca atcctcctcc cttggcctcc caaagtgctg gtattacagg    35880
tgtaagccat tgcgccctgc ctgatttttt aaatgtgcaa acagataagt tggaaaagtg    35940
atttccaata aagataaaga gttgatggtt ttaaaatacg taaagagctt atatgaatga    36000
gaaaaacact aacattccaa aagattagaa ggcaaaggac agaaagaaac aaatcactat    36060
gtctgggaag ggacatgaag gagcaggttc ccactgggcc agcggggctc aaacccactg    36120
gggacgtccg agagactgca agggccatgc cttcacattg ccgtacctga aagcaagga    36180 gctggggtat ttatctcttt cacactttgg gaggctgagg tgggcggatc acctgaggtc    36240
aggagttcga gactagcctg gccaacacag tgaaaccccg tctctactaa aactagaaat    36300
aattagctgg gtgtggtggc acacacctgt aatcccagct acttggaagg ctgaggcatg    36360
agaattgctt gagcccagga ggtagaggct gcagtgagca taaattgcac cactgcactc    36420
cagcctgggt gaaactctgt ctcaaaaagt aataataatc atgataaata aaataacatt    36480
agattgttag cagaagtagc cacaggtttc tcccacctct ctgcaagttg ctgagtgtga    36540
ttcccatcaa gaggtacaat gtcttttat ttttattta tttattttat ttatattgcc    36600
tatgttgtct aggctggttc caaactcctg agctcaagtg atccttctac gtcagccccc    36660
caaagtgttg ggattacagg catcagccac tgcacctggc ccagatactt tttcttgagt    36720
aggaatttcg agtcaccctg aacattgcat gccttcgtag tggggaagac aataggaaac    36780
cacaggctgt aggctaaaat gggttgtgtt tcttgtaacg tcatgacaag gcataaccca    36840
tcttggcata gtaaatagta agcactcact gaactgatga ttttaaatct tgctgtttta    36900
ttcagcaata tcctaaatta gcgctatgtt agtggagttg catctccctc atggattagt    36960
ctgaaaaaga tgagaaatct gtatgtagac caagttatcc ttaaactgct cataatgtat    37020
gatgcacgtg gttttacgtg tacagcctgg taccattgtt cttaggcaca tttcagtgcc    37080
agaactctta atacccagga agaagcaaaa agaaagatgg aggtgcagct agaggttgtg    37140
gcctttgaac gattcattct gccttaataa gagtggtctg gctgagctcg gtggctcaca    37200
cctgtaatcc cagcactttg ggaggccaag gcaggcagat cgcttgagcc caggagttca    37260
agaccagccc aggcagcata gcgagacccc cctcccccc gtctctacaa aaaatagaa    37320 acaatgagcc aggcatggtg gaacgtagtg cgtggtgcct gtagtctcag ctacccagtt    37380
ggctgaggtg gaggatcac ctgagcccta gaagtcgagg cttcagtgag cccttattgt    37440
gccactgcac tccactctag gtgacagagc gagacaggtc ctgtctcgaa aagaaagaag    37500
```

```
aagaattaaa aaaagtgatt agatcccttg tgtttgggac acttgttggc agcagggatg    37560
gtagcgttta tgagggttgc atgtaacatc gcctagctca gacatctgtt tgactgtctt    37620 ccccctgaa gcgcaggctc tgtgagggca ggtcttttgt ctttcttgtt aatcttcata    37680
tgcttagtgc ttgccacata gttgatgctc agtcgatatt tggatgaatt gaagggatta    37740
atgcattgaa tctgaacctt gctttcttaa tgcatatggg gagttctttg gaaagccaca    37800
cagaggagct tggttgcctg cttcctctct tccccagatt gtcttttat tgttgtggct    37860 tcactgaagc actctcactt caaataattt tgggcattgg tcgtatttta ttctttgttc    37920
cttcttcatc cttacccctc agatggtatg tagaaaagta cactacatct agaaagtact    37980
ttataaactc atttggttga taataataca tatgcctttt ccttggtcct ggtagcagaa    38040
tcttgtgcca ctcttggaat acaaacgaaa ttcttaacca aagccagttt cattttgatg    38100
ttctattttc ctcccattca cactccaaat tgtgcaccaa agtatcatcc tagttttgtg    38160
aggatggttc tccatacttc agggtaggag tatcatgtgg attcctatga taccttctc    38220 cctgggacca tggagggcag cagctggtga ttgatagtct gattcccggt gaggaaagct    38280
gtgagccttc cacttgcaga tgtctgccaa ctacatgtgt ccttagtcaa ctgtaccact    38340
gtcctccggc aaacagcaga agcccagggc ctgaagttct taagctgtca ttatggaaag    38400
cagaaggtaa acaaaacaga agtgaaagta gatttaattt tttagactgt tctcttacag    38460
gaatggtttt gtggttctca gcattttaaa aaaaatagtg gttccaatat gttttattga    38520
catcaattac tgtaagtctg attcatttc tgcctattga tttctaccca aggtgaaatt    38580
catgacattt aacagaaagc ataagtgatt ttttaaaagc agacactatt agggacggta    38640
aaaataagat ttaaagtcgg gacacttgaa aaagcaattt ttataccttt ggtaacgatt    38700
ctattctgat tctttgtata aataatataa acaaaggctc tagaagctta ctataatgaa    38760
gttggtgtgc tgtttctaaa ttctggttta aggcccaaat tcattttatc tgcattaact    38820
tttttttttt tgagagtctc gctctgtcac ccaggctaga gtgcaatggt atgatctcgg    38880
ctcactgcaa cctctgcctc ccgggttcaa gcgattctcc tgcctcagcc tcccgagtag    38940
ctgggattat aggtgtgcgc caccacgccc ggctaatttt tgtattttta gtagagacgg    39000
ggtttcacta tgctggtcag gctggtctca aactcctgac cttgtgatcc gcctgcctcg    39060
gcctcccaaa gtgctgggat tacaggcgtg agccactgca cccggccgtg ttaaaatttt    39120
tcagtggtag accactatgt caatatgttg ctttcactga caacagtatt ttcttaaaga    39180
taggataccc catttctaga tgaatctcat tctagctgga aaataatttt tcagttctga    39240
aactacatca ggcctcaggg aatcaaaact agctattagc cacacacata taaagtggct    39300
ttgctttata aacgatttag ggtcaccatc aatgacaatg gtcccttttt attgtatttt    39360
taagagtttc ttatcttaaa tggctgcata actgtagagt tttaaaaaaa ttaagtaaat    39420
gaccatgtta atgctctatt aagcttccaa acaatattgt aatttacttt gaagattttt    39480
ttttattctc aacatcctgc agcttgaccg tttgcctccg tgtctcagtg ctgcttattt    39540
tgaggtgtgg actggagtcc atctgtcccc cttgcctctg aactgctccg ttttgtgttt    39600
cgtaattctt catgctgcat cctgggcgca tttctctgta gtagctttca atttgctcat    39660
gctttgactg ggcttagtct agcgtttatc ctatctctta aggttttta aaaaattttc    39720 atgattattc atttatttcc aggatttctc atttcttcag tcacatctcc ttgttctggt    39780
tttacttctt cctgttttta ttcataacat ctttttata cacgattcct tcatgtattt    39840
ctaatcttaa gtatatttaa ttgcttattt gattcttttt ttttttatt gagacagggt    39900
```

```
cttactctgc caccaggccg gagtgcagtg acatagtcat agctcactgc agcctcaact   39960
acttggactc aagcgacctt cccacctcag cctcccaggt agctaggaat acaggtgtga   40020
gagccgccac acccagctga tttgtcttac tatgttgccc aggctggtct tgaattcctg   40080
ggctcatgtg atctgccctt cttggcctcc tgaagtgctg agattatagg tgtgaaccac   40140
tgcacctggc caagtatgtt tatttattta ttctaatttg agagggagtc tcgctctgtc   40200
gtgcccaggc tgtagtgcag tggcacaatc ccagctcact gcaacctctg cctcctgggt   40260
tcatgcgatt ctcttgcctc agcctcctga gtacctgggg ttacagttgc gtgccaccac   40320
acctagctaa tttttgtgtt tttagtacag gcggggtttt accctgttgg ccaggctggt   40380
cttgaacttg tgacctgaag tgatccgccc gccttggcct cccaaagtgc tgggattaca   40440
ggcatgagcc accacgcttg gcccaagtat gtttattttt aaagtcccca acaagctata   40500
caataaattg catatggaat ggattttttgt tctagttgat tgttggtta tcatttgtag   40560 aactaactag ttgtcttctg tgtttgatac cttgcttcta ggtcattttg agttgggagc   40620
cttttgtttt gttttttattc tcatgctgtt tttgagccta gctgtgcctt tatggttttc   40680
tctaaattta attgaccatt gttttatatt tggagcagtg ggtgtacatc agagtgtgaa   40740
agcagcccca ccctctccac cagaaggtct ccatgccagt ttcacgaagc atttttcatg   40800
ccctcattcc tgcccttatc ccttgatttg tggggagttt gtaaagcagt tgattgtttt   40860
ttttccacgt agttttccaa gtgcacataa ttgttctgtt agtgacttgt agctccatta   40920
tctattaacc ttgccccaga ccactgtaca agcggaccca acgcttcctc cagctgtggc   40980
agggacagtt acttggtatc ctgctgcctt ttcaatgctg accagttttg ccccttcctc   41040
ccctcaaccc ctgtctcttca ttcaactatc accaaaccaa aagattctgg tttgcttttt   41100
agtatgtgtt cttattcagt acatagtcat tttaaaattt aaaccaaaac agacttggta   41160
ctgattagct taattttaag ctttttcttt attattaaac agtgtagttt atcttagcat   41220
ttcatattaa gtatatgatt tatttcatat tgcttatatg aatgtacaca taaatataat   41280
aaaaatattt tcctaaggtt tttgtagtaa attatatcgt ttcattaact ttcatatata   41340
gcattgcttt tgacctggaa gacattgaac ctctgatgat ttgtatattc ctcggagtat   41400
actttgttac atagaaattt tctcatttat aatgagattt gtgattaaca aaatttgttc   41460
aacatgcatt actttgaaga tctggtttct aaaatttat gctagttacc ccacccccc    41520 ttctatatat atctccctat tcagcgacta ctgcaagagt tccaggaaat gtacactgtg   41580
tgttcactta ctgcattta aatcattgcc tttactatat ttctgcattt cccttcaatc    41640
tagctctgtc tgtacatttc tgaaagccag tagcttccct gaagaaccag gtaacaaccc   41700
gaacaatcaa attagataac catttgtaga atggaggttc cgggagatct tagaagatgt   41760
gatgggtgct aagggacttt gtagttccct gaagttccag tgagtaaaag gtacccttgg   41820
aattttttat tccttcagac ttttaaaaca gagatcactt tcaaaaatta ctctttctgc   41880
tttgaatcca tgttttagta actattttga cactgtttgg tcagaaggct gtgtgggtca   41940
actgcaaata aataaaataa atgtgatttc agtaatttcc atttttgtaac aagtaattga   42000 gaaaatagga ttggatcaga tatttgctta tacacattcc ctttcaggag cacttctgtt   42060
ctataaagaa tgttggtata ttgttaagga cacttcaagc tttgggaacc tttgaagtat   42120
ccattgattc agttaacaaa attatgttga gtgcctaccc tgggcctggg cctgtgttag   42180
gaggggacac taagatgaga gtccaaagca cttcttctca gactcctggc tgctaatggg   42240
ttgctgcctc tacttcttca cttagcagat agctttaaaa tgagtaatgc attttaccat   42300
```

```
ggagcccgta agagacattc acccagttgt ggaccgagga aagggtgtt aaacccagat   42360 tgtgatgttt cacttgatga agtgcttaat ataaacatgg aaatatttcc gcaaggataa   42420
actggctttt atgcctgtgt gttttcagga gaaatagaaa tctctaatca aatattgcca   42480
gcttttcacc caagtttgac ttttttgccta attgagtttg ggaggtgtct gaataatgga   42540
taatgagctt tcctgaataa atataaaaat taattaactc caggctctaa ttcattctgt   42600
taccagagtt ttgtaagcat gttacccctt tgtgttcatt gggagatcat ctgttacctt   42660
cttaaatgag tggggaagga tgggaaatga ggaagagcta taaaaactat tcaggtgaag   42720
aaggtttctg cccctccttg cccctttaa aatctccagc tcagcagatg ctttgtttaa   42780
acttgatcaa gtgcttgtga atcttcctag cctagctaaa tcataacttt ggaaggactt   42840 gctttttct ctcatgacaa tggtttacca cagaaatgat tcagatcact ttgtgtgcct   42900
gatgcctatg taaaatgata cagtgaaatg gaaaccattt acctgtaagc tttgggcaca   42960
cccaagcctg cttcaggagc acatgatcag gcgtgcactc tgggagagcc gtacacattt   43020
gacatctatg atgtgtggcg ttttattcta tcacatttct gaaatctaca ctaagagaaa   43080
ggaggctctt aaaaaaccac tgaggtgtgg actgggggaa ggagagatcc gtaaagaacc   43140
tgtttgttac ctgttgatac tatttcccat tggtaaaatt tctaatttag tgtgatccag   43200
ccctgaaatg ctgaggcaca cactgaatga ctcctgacat ctttagtgtt tttgttcagg   43260
ggactcttct gggaatctgt ttcatggcaa gtttattatt cccttttggt ttggctcatc   43320
agtttaccca gcagtcatct taatcggttt taaaggcttt tattttattt tgttttctct   43380
gtggaaattt tacacattca gtagattaga agtagttatt taatctttgg ttagcataat   43440
aaaagatctt ctagggacat tttttgcttg cagtggaagg ctagttaaat gtgttcatta   43500
gtcatgaatc tgcttttctt atagctgttg gaaacgtagc tcccctgtga tacagttgta   43560
gaatacagaa atctcgtttt gctgttacgg tacggtagtc tacttacttt cttccaaacc   43620
attaatgtta tagttaccct taattgcgta ggtcctatca cccctcaatt ttaagactct   43680
aagcctggca ttttatctta caaaatgaaa tataaagact tgtactcaga gtatgtgtgt   43740
gttttccata taccattcta aagtagagaa agatgaggga ttcgccagaa actgatttct   43800
aataaattat ccagaaactg accccttctc acctcttctg ttactgtcac tgtggtttca   43860
gccacagcat cctttgctgc attgttacct tagtttcctg actgtatcct tccttacacc   43920
attgatccct gcaatcccat ctgcgcgtag cagccagaag ggatccactt actgctgtga   43980
tcagaaatcc tcagccaggt gcagtggctc atgcctgtaa tctcagcact atgggaggct   44040
gagactggag aattatttga gcccaggagt ttgagaccag cctcaaactg ggtaatataa   44100
tgagacctca tctctacaaa caggaaaaaa aaaattttt ttttttttt aactagccag   44160 gtatagtgct aatatacctg ttctgggatc cagcatgctc tccctgacct gcagcttcat   44220
ctccaccact ttgcccctca ctcccaccac aatggctttc ttctcttcct cagacatgcc   44280
gtgcgtcctc ctacctggaa tattcccctc caaacattcc catggctcac tccctcacct   44340
tcatcagatc tctgttccag tgtcactttt actggaaggt cttttgtgac catcctactt   44400
attataaaaa aataatctgc ccaaccttct ccttttattt cctctacttg atttttcaat   44460
ttagtactta tcagctgaca tatattttgt ctctctgtct ctctctgtct ctcatagaag   44520
gtaaattcta taaaggaagg aattttatg tttggttctt tgctgtagct ccaatattca   44580
aaacagtgcc tgcacacag taggccctt atatttgttg aataaatgtt gacactctga   44640
tatctaattt ttgtctggtg actaatacga aaactataga gtgataataa aagcattacc   44700
```

```
ttagtagact ggaaagggat gagcgctagg atgaactttc tgcctggcga tcttgctgaa    44760
tttaggaggc agattggggt tcaaaggagg ctgaaatggc taggatttgc agagcagggt    44820
actaaggatg agcaggctat gacagaaaga actccagaaa tctgcaaagg gatcaccttg    44880
agtctggctg gatacagtgt acactttgta gggtgtctct tcatgagctt ggataaagaa    44940
caactgttgg ggagtggata attcccagca ctcattcaag cttgcatcgg ccagaacgga    45000
gagagacaga cctctgtaat acgtaggata tttggtagaa acattcaacc gaaaaccatc    45060
agatatgcaa aaagtaataa taataagtaa acaatgtgat gcatagctag aagaaaaatc    45120
agacattaga agcaagccca gaaatgacag atgataaatt agcagataag gacattaaaa    45180
cagctattat aaataactta gcagatttaa agaaaaacaa cataatgagg ataatggaag    45240
aaaaacaacc gaataccatt tctaaagaag aaaaatacaa tatctgaaat gagaatttag    45300
ctggatagga ttaatagttt aggcactgca gaagaaaaaa acagcatcta tatgagaata    45360
tacccaaggg aagtacagag aggaaaaaaa tgtggattgg ggggtgcctc agtgacatat    45420
ggaacaatat taaacaagtc tgcccccaaa atacttgaag gataaggtt caagtttttt    45480 ccaggtttaa tgaaaactat aagcctacag attcaagcat ttcaacaaac cttcagcaaa    45540
ataaacaaaa ccacagtagg cctggcacac tgtctcatgc ctgcaatccc agcactttgg    45600
gagcctgagt caggaggatt gcttgagatc tgcttgggca acatagccag accctgtctc    45660
tacaaaaaat aaaatgaaat aaattagctg gatgtggagg tccacacctg taactctagc    45720
tagcctggag gctaagaagg gaggattgcc tgagcccagt agttcaaggc tggagtgagc    45780
taggactgca tcactgcact ccagcctagg caacagcaag accacatctc tctctctctc    45840
tctctctctc tctcaaaagg cagtgaaata acgacttatt tggggaaaaa ataaaggcag    45900
agaatttgtt gccagcagac tagcataaaa aaaaggaagt ccttgaaaca gaagagaaat    45960
gataaaagat ggaaatttgg atatatacta aagaatgagg attgctaaaa gtgacataca    46020
tagataaata tgaaatatat ttttatttta aaatttattt aaagcaaaaa taaaaataca    46080
tcatatttat aacatagaaa taaaaaatgt atgataatag cataaaggat aagtggacaa    46140
atgctgttgt cgtattttg gtaaaatgca ctattatttg aaagtagacc atcgtgaatt    46200
cgatgcatat tgtaaaccaa atagaacact aaaaaatgaa aataaagaga tatggctaat    46260
gtgccaatgg tggagataag atagatgcaa aaaagaaaa acattcaaaa gaaggcagag    46320
acagaggaaa aaaggaccaa agatcaaatg agtcaaatag aaagcagcta aactagcaat    46380
atggcagatt taaatctagc catgtcaata gttatattaa atgtaaatgt tctaaatacc    46440
tgaattaaag gatgaagatt gtcagattag attgaaaaag catgacccaa ctacatgctg    46500
tctgtaagaa attagaaaaa gaacaaatta aatccaaagt aagaagaaag gaaatagagt    46560
agaagttagt gaagtataaa acaaagagca aagaaaatca attaaatgaa aagctggttc    46620
tttgtaaaga tcagtaaaat tgataaattt ctagctaaac tggccaagaa aaaagaaaag    46680
acatacaaat taacagtatc aggaagaaaa acagagaatt caaggagtg taatgcaaac    46740 tttatgctag taaatgcaat aagttagatg gtatggaaaa aaatgtgaac aatacaaagc    46800
agactgtggt tgcctttggt ggcagtagcg gggtgggagt ggaaggttga attgactgga    46860
accagaagca caagtgaact ttttgggtg atggaaatgt tttgtatctt ggttgcattg    46920
atagttaaat ggttgtagac attgcttaaa actcactgaa cacttaagtg ggtatgtttt    46980
attatttgta aaatataccct caaaagcagt tttaaaaatg tattcaagta catacttaag    47040
atctttgcat tttactctga gtataccttaa attttaaaat ctgttttttta aaaagtatta    47100
```

```
tgtagatacc ttttattttc ccaatgtctt tattaaatga catctccacg ttttgcttct   47160
tacctctatt tttttttttt tatttctctg tctctcaggc atgcacacac acacaccaaa   47220
aaaagtacat atgcataatc cttttggctg aataaaatca gttgcaactg ttatttcggc   47280
ccttatttgc tccgggtaaa tattcgttag ctgagtggtt tatctgtatc agatatttct   47340
tacatcttca tccagtcaca ccagctggac tgaccagatt gttttcact tcaagggcag   47400 aatttgtact cactgctgaa tgcttccaaa tgatacgtag aataacaaat ttaagactta   47460
gatttttact ttttcaggtc tttttttttt tttctgtgct gtatagcatt tccctgaaag   47520
cttaatctca tctgtaagtg atgcagtgga tgtgttacta ttggattaat ttatttactc   47580
ttaggtaggt ttgtaatctg tcatcatgct gttgttttt tgtgtgggtt tgttttggt   47640 tttgagacag ggtctcactc tgctgcccag gctggagagg ctagagtgca gtgatgtgtt   47700
tatgggtcac tgcagattca atctcctggg ctcaagtgat cttcctgcct caacccttg   47760 tgtagatgga agcacaggtg cacgccacca cacccggcta ttttttaaa tgtattgtag   47820 agacgaggca tcatttttt gcccaaggct gatcttgaac tcctgggctc aaacaatcct   47880
cccacctcgg ctcccaaagt gctgggatta cagatgtgaa ccaccactcg agctccatca   47940
ttctgttatt agttgttctc tagtatgagt caaaaactct tacctgccct tttacagttt   48000
tataaataag taagcagaat agcagaatgt ggacatttt taaatccaaa ttgaatatgc   48060
acatgactca aggagtcaaa tagtaccgta atcggtttat gataaaatcc agtggtttgg   48120
ctgggtgtcg tggctcacac ttgtaatccc agcaccttgg gaggctgagg caggtggatc   48180
acctgaagtc aggagtttga gaccagtctg acctacatgg tgaaactact aaaatacaaa   48240
attagctggg catggtggtg catgcctgta atcccagcta cttgggaggc tgaggcagga   48300
gaattgcttc aacccgggag gcagaggttg tggtgagccg atatcgcatt atttcagaac   48360 aatttttccac aagatcagtg agtgctgtcc aatagacata taatacaacc cacatacatg   48420
actttacatt ttcttgtagc catagtagaa aaggtcaaaa gaagcagatg aaattaatag   48480
cctgggcaac aagagcaaaa ccccatcttt taaaaaataa aataaaatat ggtggtttgc   48540
tgtccccacc tcagaccatt tctctggtct ttctcattga ccaccactcc caatctttgt   48600
tctgctgatt gattacagct tgtatatatc tccatatttc taagcaaaat gtttatcttt   48660
tttaaattta taaattcttt ttattattt tcagagacag ggtcttaact ctgtcgccca   48720
ggctggagta cagtggcacc atcgtagctc actgtagcct cgaactcctg ggctcaagca   48780
gtcttcctgc ctccgcctct caggtagctg agactacgct acaggcacat accaccatgc   48840
ccagctcaaa atgtttatct tttgatacat tattcgagac cattattaag gtggatgatt   48900
tagttttctt aaacagccat cccctttctt ttcctcccct ctgcttcacc gccccatt   48960 tcccaatgtt ttaccttttg gttaaatcag tactcattgt ttacattatt tgcctctgca   49020
catagtcaca gatagtattg tactgtactg tactgtgttt cttttttaaa cattatttct   49080
gttgttaata attgactttt taatttttt cctattttgt tttttaaaga gatgggtct   49140 tactatattg cccaggctag agttcagtgg ctcttcgcgg gcatgatccc actgctgatc   49200
agtacaggaa tttccacctg ctccatttcc aacctggacc agttcacccc ttcttaggca   49260
acctggtggt ccccattcc cgggaggtca gcatattgat gccaaactta gtgcggacac   49320
ccgatcggca taacgcatgc agcccaggac tcctgggctc aagcagtcct cccgggctca   49380
agcagtcctc ccacctaagc ctcccgcgta gctgagacta cagacacttg ccaccacacc   49440
aggttaattt ttgtgttttt tgtagaggtg gggttttgcc atgttgtcca gactcatctc   49500
```

```
aaacttctca gctcaagtga gcctcctgcc tcagcttccc aagtagctgg gattatagac   49560
gcatgccacc acaccccatg ataattgcct tttttttttaa tttgcataat tttctttgta   49620
gcttttgcta atgttcccat atcttcttat agccttacag aatgattttc cacaagatca   49680
gtgagtgctg tccagtagac atataataca acccacatac atgattttac cttttttttgt   49740 agccatagta aaaaggtca aaagaagcag atgaaattaa tagtatcttt tacttaaccc   49800
agttcattca aaatgttatt tcaataaatg gtcaatattt aaaatacttg agatattttg   49860 cttttatta tttcttttgt tactaagtct tcaaaatcca atgtgtattt tacacttaca   49920
gaacatctct tttagactg gccacatgta gctcagggtt actgtattgg acagagtggt   49980
ttcagtttca agttttttcct tggagacatc ctacttgaaa tttccattct ccatgtatct   50040
gggtggttgg tctatagact tgccactcac agctgtcatc ttgagacttt ctttgctttt   50100
cttctctatt ggatattcag tttcctggat ttcaggtctt ctcattttcc tctagtagtt   50160
ttgttaggtc atggttggta tggcatggtt gggatagcgt gttcacacag ctatctcgtg   50220
agtcatactc ctccaatcca gcctgctcgc ttcccgtgtc tgtcatgtag ttgtcaccct   50280
gctatctctc cctccagttt ttgcagaaat ttcctttgtc ttcactcttg gtcttcctct   50340
cccatccccc atgtatccta tatctttctc tttcttggtt tatttcatca ctcaggtgga   50400
aaagatgctc cagtggatta ctgggaaaag ggggagcatg gatgataaag gtattgagac   50460
cttacacgtc agggaatttt ttttttttt tttttttgag acggagtttt gctcttgtcc   50520
aggttggagt gcagtggcgc caactcggct cactgcaacc tccacctcct gggttcaagt   50580
gattctcctg cctcagcctc ctgagtagct gggattacag gtgcccgcca ccacgcccag   50640 ctaattttt gtattttttaa tagagacgag gtttcactgt gttggccagg ctggtcttga   50700
actcctactt caggcaatcc acccacctcg gaatgttttt attgtcccctt tcatttcat   50760 gactgctggg ctaggtatag aattccagaa tcattgttct tagaatctcg aaggcattgc   50820
ttcattgctg gccagctttc agtgttcttg caaagtctga agctgtgcta atcacctcat   50880
cctttgaaag tgaactgttt tttcttccca gaaacttaca gaacattctc tttgtccgca   50940
gaattctggg attgcaatta ctgtgcctta gaatgggtct gttttttatca ttatgaagag   51000 tactggatgg gtcgggaggt tttcttgaat tacttcttga tgttttcttt ccttgtattt   51060
ttttgtttgc taatttttcta ttttttttttc ttggtttact ttcttgggca gggggatttc   51120
ttctacttat atttgattct tcagttgagc ttgtcatttt tgctatcttg ttttaagtt   51180 tcgagagaca tctttgtttt atataacatt ctgttcttaa tacatagatg caagatcttt   51240 tcttttctgag tatattaata tgtatttgaa atctttctat tctctgcagt ttgtttcccc   51300
caagggtttt ttttttttttc tggttttttgt ttttgtttt tatgttagag actttcctgt   51360
tatatctggt catcagtggt acctgcatgt ggtggagagt aggggcttat tggagtatga   51420
gaaccttgag caggtgtaag gagcctgtca acactgcgct ggcctcaggg cctctaggga   51480
ggctgccagt tgtgcattct gaggataacct tttggttgtg cctttttgtct ggtcagatta   51540 tctagagatg ctctgcctcc tacctggagg agaagggtct agctgccagc ggtgtgagtg   51600
tctcttgggg aaaaggactc gagttcctgg tgtttggctt tgtgatggcc gcttaccca   51660 tttttggtgg agcgctcaca tcttccactg tgccaacagt cttgctgcag ttcatagacc   51720
ttctggttta cattttttcca gaaagtatgt ctttagattt ctgcagaagt ctgaggagca   51780
tggaaggagc ttgggaatg agatggcaat ccaggtcttc ccagatggct ctaccttat   51840 cccctgcagg gaatcccact cctccttcct gactgggagc acagccagag cctgggagg   51900
```

```
aatctggagt ggaaatctcg ggcggtctgg ctttcttact gttcacttgt aattttgctt   51960
tctcacaact gccaaccact aatcagcctg atttccagct tccagaattc tattgctgtt   52020
gtctgctctc ctattcccac cgtagggat ggggctgtct tttttttttt ttttaatttt    52080
ggtaaaacat acaaaacata aagtgttcca ttttagccat ttttaggtac acagttcagt   52140
ggcagtaagt acattcacgt tgtgtgtatt tgttttttta gtaataaaca atataaaatt   52200
ttttaagtaa taaaacacaa ataaaagatt gtttaatgtg attatcgtgg aattttaggt   52260
gtgatcagga gccatggtgt agtcttctgt tgaaacaggg tgataggatt tgtttaccac   52320
ctcctaggaa agcagttgga tagtttgttg gcataaaagt acattttatc tatttttaat   52380
aatcgtagct ttatagaaat tgcagttgga actcccaggc ctggcattca aggctctctg   52440
agatctgggc tacccaccca tgtcctccag ccgtctgtcg cacctcctac tgcccactca   52500
ctgttcctgg catgagatgt gatctccagc ccccatgcct ttgctgtgca gggtgttcca   52560
gagtgaattg tccctcctgt ctgtctctct gccctcttcc tcgtctttcc atcttcctgc   52620
cccacatcac tgcctcctac ccaaggcctg tgctcattcc tcctcggttt tcccccatgg   52680
cctggtacat acctctgaat tatcaccttg catttcccat attgcccggc tctctttgat   52740
gtctgtttct ttgctgggtc ttcctcagtg tctgacggtc agttaaatgt ctttattctt   52800
ttttgtagga tatccgacat gaagccagtg acttcccatg tagagtggcc aagcttccta   52860
agaacaaaaa ccgaaatagg tacagagacg tcagtccctg taagtatcca cgtggccggt   52920
accagtcttg ctcttccttt gctgcaggcc ttttttagtca agactccttt cgcctcaggg   52980
tttagtataa taataaatca atgtagcaga ggtttatgac gcgattgttt cctatagtaa   53040
aggcattaga gacttatagt aatagctcat ttttccacca ttatagaagg gctcaggttt   53100
cagtttctgg aaaattcagt gaagttcaaa gcacttttct taagctttga ctgttttttgt  53160 gatgaatcat tttcctacca gctgaagcag agtatagcag gcataataaa accttttctg   53220
gatgactcag cagcagcgtc attagggcat gagcactgtg ttccgctgta atgaagcccc   53280
gcacaggcat tcggggtggg cactgtcgtc ccctgcgctg aatatgcaag gcagctctgt   53340
ctggagtccc caccgcctcc accccgcca acctcatcat ttttctccct ctttcctgct    53400
gttagttctt cctaggattg tcagtgtgcc tgctggcctg tggcagccct gtccgccttc   53460
tgagtgattg gctgtcagtc tgccggtagc tgaaaagtaa ataacttaac atgttagaat   53520
ttgcataaag taaggaaaac tggagctgag tacaggactt gaactgcgcc atctcctcta   53580
ggccacagag gccttttga ccccttcca ggtctttaga cattgtcagg cagtgagggg     53640
tcgtagctgc cagtgtctcc atggtagcgt gctctgccag ggatgcagaa gattctccag   53700
tcattcctcc agtgggcact tcctgcaggt cctgtgccca tggctgggag tggtggctgt   53760
cattgttctc tgccagaagg gttagcagtg catcctgacc tgacttatgt ggcgcccaga   53820
ttcctggaag gggtctaaaa atggacctag acttggtgta gaacgtgtgc ctcttggcct   53880
gccaccatgg ttccctgcct ggttttgtgt gtcagctctg ccgcttaaga actgagtggc   53940
ttcgggcaag ttgttctctc tcataggagt gtgtgaagat gaagcaacat aagctgctta   54000
gcccagcgcc cagtacctca cgcagacata agtgctcagt aaatgttgtc tgtggtgggg   54060
atggttgtca ccaacatctg aagtgcactt ctaggtcatc aggtgacatg attggcgcca   54120
acacatggta ctcttgattt agcacatctc agctgaggca cctcattgat atttgtttaa   54180
aaacaaaaac aaaaaaccttt ggtgattctg ctgtgaagtc ctggcagaa acctccagac   54240 cgctgatcaa cacgcaacag aaccatcacc gttcacctct ttgacatggt gccaggatac   54300
```

```
cctggatctc tagcttttgc tatagttgct ctaattaggg aataatcttg tctttaatat   54360
tcctttgcta catttttaa catttcttat ctaaatggtt ttatgaatca gttttacaga   54420 gaaaaaaac cagtatttaa aatattcttc caggggctgg tccaagtaca gtagtgttta   54480
caactatgtg atcacaacca gttacagatt tctttgttcc ttctccatcc ccactgcttt   54540
acttgactag ccaaaaaaaa aaaaaaaaaa agttattcca gggaaacaat tctccaactt   54600
tttcactccc aatctcactc ctcttatctt cctcccgtac tcctatcctc ctcccgtact   54660
cctatcctcc tccctactc ctatcctcca gtagaaacag tcatttgctg tgaaggttat   54720
gggggagaat gagtcaaggt agaaggtcac ctgctgccca gctcacagtg ctgctggtga   54780
tgacagcagt ccacagttac aggcacttgc tgaacgaggg gctctgtata cacctcagct   54840
cattgactct tcccacaacc ctcttgtcac ctaccattta gcaaatgaaa aaaccaaggc   54900
tctgaggtga gttgtttgcc cagagtcacc cagtgctgtt tgaacccact cacataacca   54960
accaatacca ttatgtaatt tttgaggtct tttatctctg tgatccactt aaaaattatc   55020
caagtatctt tatttgtact aagcctccat aatgagaaac agtgttccag atggtggcta   55080
gttttcaaag acatctctct ttggaattct tctttagaac aaaaagcccc agaccactta   55140
tccccattca tatccccttt ggacctaggg agaaggtact atttataggt gatcacctga   55200
gtttattgtc ccttgtgctg tgccagaaat aaaggtcccc acctgctctt attagctcta   55260
ctaacaggat aaggaaagtg gccctcagag agctactgct tttgtgacaa acaaatgata   55320
caagaaaaaa aaagtggctt tttaatttta gtgacctggg gcaggacttc caaatgaaag   55380
tttatttcta aaaactaaaa ggtaaattta atatactttc agtgtttggg cttaaattct   55440
ctttcaagtg tctttgtgat atgctctgaa ttttaaaaat ttagaatcat tgaagttcat   55500
tatacttgaa ctttaaaaaa aaaaacaaa aacctcgtat aaaggtcaag gtatgacttc   55560
atgctgctgt gtacttaggt catttaatct tcaaaccact ggatagaggt taggttgaag   55620
ttcgatctta aatcctacct actgtagctc attgtaccag caacagctgt agggactagg   55680
tggaattcat ggtgggtttt gttccctttt aaagattgaa gccaccatat tttctgccct   55740
ctaaaagttt atgtcagcca ggcatgggtg gctcacactt gtaatcccag cactttgggg   55800
aggctgaggt gggtggatca cttgaggcca ggagttcgag accagcctgg ccaacatggt   55860
gaaaccccat ctctactaaa aatagaaaaa ttaggtgagc atggtggcct gcgcctgtaa   55920
tcccagctac tcgggaggct gaggcaggag aaacatttga atccgggaga tggaggctgc   55980
agtgagctga gaacatgcca ctgcactcca gcctgggtga cagagtgaga ctcttgactc   56040
aaaaaaaaaa gttatgcatc agagaacaga tcctttgatg ccctcctctg ccctgaaagg   56100
tttttggggg agagtaataa gtatcacaac aagatatgac ctgagaacag atttcccaga   56160
taggacatga tccatgtttt aatatggctt actgctgttg cttcatagtg tgaagcttca   56220
gacacttctg aaaacccttt cagaaaatcc cagtcgcccc atactgatga ctaatctcaa   56280
ctaaaacagg gcttcagcca gtgtgaatgc cactaatgcc accaactcac ctttgctttt   56340
ctgtagggtg tgcacctgta tgtacacatt cagcttttcc gggattaacc tctgagttct   56400
ggtttgtctt tcagttgacc atagtcggat taaactacat caagaagata atgactatat   56460
caacgctagt ttgataaaaa tggaagaagc ccaaggagt tacattctta cccaggtaag   56520
cagattgtct gaattttcta tttaatgtca atttaagagt ttgagagtgc tgttatccac   56580
acctcaaata aaatctgcca catccttag aaggtcagga tttcagcata ccaaaaagca   56640
gcaaggaagg gggaaaaatc atccttcaaa ggttcagttt ggttataagg aacgctaatc   56700
```

```
tttctggga agcataagat gacattgctg gaaatgagag cttatagaaa acaacattaa    56760
aatgccagag ttgcctgtgt ggtctgttgg cagagacagc agagccatgg ctggaggagg    56820
gtctgtacct gtgttgcttc cagaagtatt tgtcgtagag cacttgtgat ggcaaatcta    56880
agaacgttag cagtagacca ggaatctctg tccagagcca ttcagagtag ctcagcatgg    56940
ttctcattct ttggccagaa gaaaggcatc attggatcat gtgaacaagc atgaaaaatg    57000
acttaaaatt tctgttggct tttggcatct ttatggaaac aaaatcctga aagtggttta    57060
ataattgagc ctcttgtaaa acactcagtg gcatgtgacc aaaagggtat ctgggaaaga    57120
ggataaaaag agtttctttt taattaatct tctcaagtct taacttgtta cctgtaagtt    57180
ggtctaaaaa gactgggttt cttattttgt ttttcatcat aattttttgtt tctcattcca    57240 tgtcagcttt cagtcttata tggctttagg ccacagggcg attttgaaca tttgtaattt    57300
tgcttaataa ttaggaaatt aaaattctgg ggaagacaga atgctctatg aagaaaggct    57360
gctttgagca aggagctagg tcagggcgcg ttcaactgag gcctttcttc actgcctttt    57420
tgtcttgtcc cagttcctcc ccatttatga ctaaaatcag cccagatgct tctcgtcatc    57480
tgggatgcag agcatcagcc cagctgtgtt cagtcctatg gggccattga gtaagttctt    57540
ggtgcatgga tacagggcag gcctttacca ggccctgagc ccctggtcct cccagcacct    57600
ctggggtatt taggggaggc tgatggggga gggggttgat aaggcgggag atgtctgggg    57660
atgaggttga ggcaaaagtg acttcttgag gactttgctt tttggagaag tcaaatttcc    57720
tacttcttga tttcagccct tcaactctgg tatggagtca ggaagccctt taaatacctg    57780
ttgtcgggtg tatcatgtca agtgttgcat tagcaaatga ccatgtatcc ttgtgctact    57840
gtcctgccta ccccgcatcc tagcgcttcc ttgggacatg agaagctctg tctggtttgt    57900
gaggtggcac tggggatgtt gagaaactgt ttacacagtt tcccttttgcc ctggggattt    57960 actaaaggag tcgaggcagc ctgaccccaa agcatcaccc ctggacacta tgaccgaaac    58020
atttccccag tgcccaaacc aagaacaccc ttcccatttt tttttcagtg gtgttcatta    58080
tgtaataata caagtctctc ttctcatttt ttaaaagtca gaagtacaga agagcagaga    58140
ataatgtcca aggggccctc cttcacctcc cccgtgcagt gtcagctaag tgtggtgcgt    58200
gtccttgcag atcttagggg attgtgatcc ttcagaccat tctaaactgg ggtggtgctg    58260
ggagttaggg aaggcatgaa gggagtagtg gagagctgca gtgactgggg tcttcatgcc    58320
agggtggaga atgcaaggcc caggtggcca gccatgtgcc acgggatttc tggctgccaa    58380 gagctgtttta tctgttcact ggggagggaa gagttaaatg tggtctgctt ttctccgagt    58440
cccttcagca cagggagtgc tgacttgtct tgttcaggta gtaagttcaa gatgagctca    58500
ggaaagaaag tgagaggaca ctgagggcta gtggttgagc caagtgtgat gggacttaaa    58560
gggagaagat ttaaagaata aggagcttat gggccgggga cggtggctta cgcctgtaat    58620
cccagcactt tgggaggctg aagcaggtgg atcacttggg tcaggagttc gaggccagcc    58680
tggccaacat ggtgaaaccc cgtctctact aaaaatacag aaattagctg ggtgtggtag    58740
tgtgcacctg taatcccagc tacttgggag gctgagacag gagaatcgct tgagcccagg    58800
aggcagaggt tgcagtgagc caggattgcg cccctgtact ccagcctggg tgatggagcg    58860
agactctgcc tcaaaaaaaa ttaaaaaaaa ataaagaggt taggtgaaaa tagatgagaa    58920
tggaaaccat gagaagaagt gatgctggcc aaggacatga caggttctga tgtgaggtg    58980 ataggcaatg tctcttccag ccactgctaa taattgagac aaaactcaagg cattcatacc    59040 ctgtgtccag taaacatctg tgcccattgc caggtgagct ggattgaaat gggccagctg    59100
```

```
ctcagcagac accctcatgc cccagtgact ctgttccct tgggccacct cattgaccat    59160
ttatgtttct acatctccta agtttgttgg gccaaggatg gaggctgtct gccgtcaggg    59220
tcctcattgc tgatggtagg aatagttgct gatgtttcat tggatgttgc tgtattctag    59280
ggactgtgct aagtacttta tagaaatgaa catacttcat tttcacagtt ttatgaatag    59340
ggactattat tagtcaagta agcgatgggg aaactggggc agggagcgat gaagtgactt    59400
gcgcaaggtc acaagatgat gtgattggaa ccaagagaag tgttgtggtt ggccacgccc    59460
ccacactgcc tctcatctgc accaaggagt tttgtcccat agcccaaggg ccttggggac    59520
gaatctcagt ggaggcccct agcgggcctg cctgagccag aaagcagaat cggcattttt    59580
ctgtccttgg ttggcccagc cctgaactga gatgcgaaaa tcgcctttcg ctgcctggta    59640
gaaaatggag ctgcagttac tgaccaccag gcagagagag gtgggtccct gtcccagcct    59700
cagccaccac tctgcctaag ctgtggggac tgagggcgct gtcgttagct gactgcagaa    59760
ggtgagcaca cgctgtagca tgttatgttt cagatgtcac atgttgtgtt attgtgtctt    59820
tgcagggccc tttgcctaac acatgcggtc acttttggga gatggtgtgg gagcagaaaa    59880
gcaggggtgt cgtcatgctc aacagagtga tggagaaagg ttcggtaagt ctcggcttca    59940
tttgctgtgt atgtgatcat gcataccact ccatatagtt accattttcg tccagatttt    60000
taaattattt ttcttgcctt tgtatttcct ttacgtagta ttttattta aaaaaattaa    60060 aacagcagca tataaatgca tgttggttgt caaccagtta atgaagtgaa taaaagggag    60120
gaggcggaag aactgcacgg aacctcttcgc ccccgccttc tcctgtgtgg tgcgtgtggc    60180
gctccgccca cctgtgctgc ctgtgcggct ctcatcacag tgtggagttg tgtgtggagt    60240
tatggagacc tgcttttatc ttgaaaagca agttcttagt gcatcttcat ggtgtctgat    60300
tttttggctg gtgagagtgt ggctacctct gcggagctgt gggagcggct gactagatga    60360
gatttgcctc cattcagtac ctagactctt gccctgccac acctcttcgg agtgagcatt    60420
gacttcagga tgtgtgtcat tctaagttcc tgcaacttttt caaacacccc tcgggctagc    60480
gtgtggctgc acggtgtcca tttgtgcagg ccaccactcc tcttgcatct gggtctagcc    60540
acctctcctt cttgacttac catagttcat tttgtaccat gctttcagaa tgagctttct    60600
caaatccaag tctcaccacg gttcttccca gctgaaaacc cttgtgcggt tcccttttgcc   60660 tcacaggata atacatggtg tggcttacgg aaccctgcag gtctggccct aggcccctgg    60720
acacagacct ctcaccactc ttggaacttt agccaggaca aagttttctg ttttttagttt   60780 cttaccatgt tctctgggcc gaggagtccc agtgcccacg ttcatcccac ttgcaggcac    60840
ccctggacgg ctgcccccag ctccccaact gcctgcattc tcccctgccc tcctcactct    60900
gttggaatag ctgagaatag ccgatttctg ggcagccggc ctcctgtgta gactgtcctg    60960
tgtagactgt cctgtgtaga ttgtctgtgt agactgtcct gtgtagattg tctgtgtaga    61020
ctgtcctgtg tagactgtcc atgtaaactg tcctgtgtag attgtctgtg tagactgtcc    61080
tgtgtagact gtcctgtgta gattgtctgt gtagactgtc tctgtagacc gtcgtgtata    61140
gactgtcctg tgtagactgt ctctgtagac cgtcgtgtat agactgtcct gtgtagactg    61200
tctctgtaga ccgtcctgtg tagattgtct gtgtagacca tcctgtgtag accatcccat    61260
ttagaccatc tgcctgtgca ggcgcaggcc agtgttcagc agggccacag gctcctcggc    61320
ctccctgccc tcgctgctcc ccaacactgc caaccctgct gcggggtcca ggaggagatg    61380
ggctgaggat cgtggagacc agcaggagcg tgtggcccag gagcagggaa ctgggtgtcc    61440
ttgggccttg ccaggtccag gctcagctag gacacggctc tcacagctgt cctggttgcc    61500
```

```
tccggccaca gaagaaggtg agggctccag agaggccacc tttccaaaaa aagcacagtc   61560
atggccctag aatgtaaaaa atccaagtgt taagaaggaa cacatcaaag gaaacttcag   61620
cagtgaaaac ttgaagcatt aaccacgaag cctctgcctc caccacacac aaagaaacgg   61680
ctttagttac tcgcagaaag tcttcctctt aggacagcgc gtgtttaaaa tcatagggt    61740 ttggtttgtt ttgttttggg gttgggqttt tttgggggtt ttttacccct gcctactttt   61800
taaaaaatga aagtgtttat ttgcccaaca ataacagaca gggagcttgc ctaagtgttc   61860
tgttgatgat ataatgtatc ttgtcttaga aaaaaacttt ttcagtgaaa ggtggttttt   61920
aaattttttc ttccctcctt agtagcttga ttagtaaaat gtgaagttac aaatgtgaag   61980
caaaccccca cccttcacca ctagtcagca attttgagta aagaaacaaa gcatcaggtg   62040
ctcacagcac acactgtctt agagggaagg ggaagcctgg tggcctgtgg aagccttcag   62100
catagctcca tctgcaggct tctgaccctc agcactactg acacttgggc tggatcattg   62160
tctgctaggg atccgggcag ggagtggctg tgctgggcgc tgtaggaagt ttagcagcat   62220
ctctggcctc tatccaccag atgccagtag caccccctcc ccagatgtgg cagtcagatg   62280
tgtttctgtc tagactccag actttgtcca acgtcccctg gtaggccaaa ttgccccgg    62340 ttgagaacca ccgctctaga tggtattgag ggttgggaat tttaaatcaa gacatttatt   62400
cagaaattac cagatatagt agcatttgct tcttatttat ttctttgttg ctaagtgttt   62460
ggcaaaacct ctttgctgtg agcacaaggt ttgctttagc aattgttgtc acattacagc   62520
aaggagtggt gtccagcgct gtagttatgt atttgagcag tgtccagtgc tgtagttatg   62580
tgttccagcc tcaccaggcc ctgtgcttca ttgtctccca ctcaagactg accacaaatg   62640
gcccacagat ccactgtgac aacctttccc tttgggttac tgtggtggca tcgagaacat   62700
ggctggttgg ctttgctgta gtttactgtg ataactgtgc cagcagtccc tgctttcctt   62760
tgttaagtat cccattccac tggaggatta cttgggcgtg cagattggca tgaaaagcaa   62820
tgtatggttt gagattgtta aagtttcttt gggatcaaca ttttcaattc tgtatcagca   62880
ttatccctcc cagagggctg gctgggagaa atcatgagaa gttacagtat cttatttgct   62940
cagctaatct aattataaat gatccacaca gcttgtggta aaaccagctt tggggagtt    63000 ttcatttaat gcatacttgt cttctgattt ccttccttca ccaaatagtg taggatgctc   63060
cctcttattt ttggcaaaca tgcctgttat cttttgggac cctgggcttc ctggaaacca   63120
gttatgcaga agatgattgt gtgtgttaga ctggggtcat ccagatggct agagttctca   63180
ctggttctgt ttaaggattg actttagaca cctcagtgta ggctgcacca tggcgtaagg   63240
gttgggattg ttgtttagaa gggggaagta agcaaggtga gtttaattgg ccattgcaga   63300
atctcacccg tatctccctc ctgaaatcct cactaaagct gccgtttgct ttcaggtgct   63360
ttcatgcaca agacactgca ttttgtatca cagggtccat ataattcatt tttctctcgt   63420
acttagttct ctgtgttaag aattacttac ttagttctct gtgttaataa tttttggcga   63480
aaccaaatta cccgtcacag ggttactgta gatgtctttc ataggttttc caaacaccac   63540
ttgcccactt gtttgggaag gccccaagga ctgtttaaca tctgccttca tggtggaaac   63600
agcaactatg agagatgcta gcatgttggc actgccatgt tcctctggta ccagcccaag   63660
ataggactca atttgaggcc tggtgaagta ctgtgttcta ataaaaatcc atctactttt   63720
catggccgta tatatcaatg taatagggta actggaaatg tgatcttgtg ccttttaaaa   63780
attttgtgtg tttaaaacaa aaatttctat tggaaatgac agagcatagc ttgttgctgt   63840
agacacctga gagtccttaa aaataaatat tgggttattg acacttagtt gcatgacaga   63900
```

```
attcctcact tgtacagttc caaagtctta gtctttaccc agattacaga gggttattaa    63960
gcattaggtt tggttttgaa agtgagtgct tgctgtctgg aggtgagctt taagactcgt    64020
ctgccctgct tatgagatga ggaagggtgg cctcttcctc ctgcatttct gttcttcgct    64080
tccttctctg tctgctcact ctgtggaatg cccaccccag cacgggtggg gtggaacctg    64140
tcagatcagt ctcttgtttc tggggtcttg aggcattata agatctagtt gttagaagtg    64200
tgggattaat tcatcttttc acattcttct aagttcctgc ttttagctgc cacacccact    64260
ttggctaagt gggggtcttg ccatgtaatt agcgcctcca tgccaagtgg cagaattgct    64320
tcaatggtga cagattgtcc ccattcaaga gttcactttt ggcaactcat cattgatcca    64380
ggaaggtgac atggatgaaa ctggctaaga cttcagacag gcttgtgtcc agactcttga    64440
gaaagctctg ttggcttctg gtctggcact gtgaagtttg ctgtgatgct ggcaccacaa    64500
cctggtgttt cctaatttgt ttctcccaca ttttgctttg gttttgtctt ttgggcagct    64560
tccagctcca gtagagcagg accaataggc atttgtggtt ctatattcac cctcctcacg    64620
tgcttcctgg ctcctcattg cccccagatg atgccacagg tccctgggcc tgctgccagt    64680
cgtctgtgat ctgggcctct gctggcccct tctccagctg ctcttttcag cctcttattt    64740
gcagtcactg cctaggaaat cctagtcatc cttcaaaacc tgcctcttgc acagagcttt    64800
ctctgatctc tcttttctgt aaccttggct gacctgaaac atttccctct tctgaattcc    64860
tgctgcatgt ccgtagcatt tcccctcag ccctccccca tagtccacct tgtcactgct    64920
gggcacagca gtgtcttctg acagacagct ggccctgaag tggttccctt cacccacacc    64980
atcctttgcc ccagaggagg tattgagtgg gtcagtgcac gtgaactgcc agtgtcattt    65040
gccaaagagc tgttgacaca cgctgacatt tcttttgctg aaaatcataa gggctttgag    65100
cttccctctg tccaggcaca tggtcaggct gacccggtag ctctgcccct gctgacctgc    65160
catttttgtc cacaacagtt atccatgagc agaaacattt gtgtaactga ggcagaaact    65220
tagttcaagt aaaatgtcac taaattcgag tcagtttttg tcttagaccc taaatgaaac    65280
caaattttca taaatttttct tgttttaaag aaaaatttaa tgagctacat ttaaactgag    65340
aacatcagat agtgtctgag attatcaaaa tagaacatca aaagtatttt tctgaatgaa    65400
ctgaaccaaa ccagaatgaa agggcaagcc ctggggagcc tgtctccaag ccttctctga    65460
aagggagtct gtatttggtg ataactgctc agcctctcca aagggcctca cctgctgtct    65520
ctcccagttt tattttaat tgcctgtgag ttttctgtgc agggtaaggc acctacattc    65580
tatgccagca gcctgatcag gtcctgggta atgtttgaaa tggctacaca gaggagtttc    65640
aaagcctttt gttcaatctg gcttcacctc gtagacggtg agaaagcgtc agagccctgc    65700
aggatcccgt tgccacgttt gaccggggag ccgatgggtt tggaagtctg agccctgtct    65760
gcacaacctg ccccggtcag cagcttcgtg ccccccacccc catctcccca tgaggcaggc    65820
atctgtgctg accatggctt ccatgttcag aaaccccag gcctttgagt tatcatgaag    65880
cttgtgggat gtgctccaag cctcctgcca tagaaaaact gccatattgc tcacaataat    65940
tcactattat ttgtttcccc agttaaaatg cgcacaatac tggccacaaa aagaagaaaa    66000
agagatgatc tttgaagaca caaatttgaa attaacattg atctctgaag atatcaagtc    66060
atattataca gtgcgacagc tagaattgga aaaccttaca gtgagtatag cacacacttc    66120
agcacttcag gcggctactg gttcacatgc ctcttccttt atcccttggg tgatattacc    66180
taatgtcagt gttcctggct tttgtatacc ccgagcaaga tgtggtttgg gcactgtggt    66240
gagcggagct tacttgtgta cctaccaagt gcccagggag ggtggaggcc acagtgctct    66300
```

```
ctctgacctt taacaacagt taacaccagt tcttagggaa aggagagttt cttacccaaa   66360
agactggttc ctgcttgtgc agctgcagag ggactggagc ggcagcctgc aagtcccagt   66420
gaagcatgct gccttctttg tggtcctcag tcttcgagtc tgaagagagg gaagaagggg   66480
tataggggct cactccagtt tcatagctag tgaaagtttt ctgggccagg tcttgggttt   66540
ttttgttgtg ggaagagttt ataacaccag ctacttgctt ggtaaaagtt ggtcttggaa   66600
catggcaagg cattgtggca agcagcactg ccgctgaacg cgctgctcct ggggctttgg   66660
aataattccc ctggatccgt aacttggggg tgttcatgtc attctgggga acagtggagg   66720
gagtgcgcgg cagcacctgg gggcaccagt gaagagtggc cagccaccaa cctctagaac   66780
ctaactgggg tcgaatcctg gccccacctt actagctcat cacagtgtct ccgtttcctc   66840
ttctgtcaaa ctcaggtttt gcgagggttc tgggaggtcc tatacgggaa gggttagcag   66900
ttaccatggg tgtgtagcac gggctttatc tgaagggaag gtggagccgt agggagacca   66960
tgtggagtgg ggctccaggg ctgtgtggt ggggagggat ctgcttctgg gttacccat   67020 gcctcccctt ctcaagtact actttttaat catcatggct cctgccattc atttcatagt   67080
tgatgtaagc caggtgcggt ggctcacgtc tttaatccca gcacttgggg aggctgaggc   67140
caggaggatc actcgaggcc aggagttcaa gaccagcttg gcaacatag tgaga cccc   67200 gtctctacaa aaaacaaaa acagttagtc agacatcgtg gtgctcccct atagtccagc   67260
tactcaggag gctgaggcag gaggattgct tgtgcccggg agttcaaggc tgcagtgagc   67320
tatgcttgca ccactgcact ctagcctggg tgacagagca agaccctgtc tcaaaaataa   67380
ataaataaaa aaaatagtag aagtaagatc tagaatgtag cacaggttac caggacgtag   67440
gcaaggggtt cgggctgcct ggctcttgag gatggtagca gtgcagctga tgtgagtgct   67500
ttctgccctc tggtggtgac cgcgccggag tcaccagccc tgccatagcc ctgatggggc   67560
agagggttct gagtacggtg gatggagtg ctttctggaa gattctcagg agtaacatgg   67620
gcagtgtgtt ggaatgtgct agaggattta tgcagtagcc ttttaaaaga atgcttttta   67680
gcatttgcaa gcctgacatt aagagtgact tctgggaaac tatttgcttg ttgagggaaa   67740
ctgaatttca acagagcaga agagctgtgc gcttttgct tggcagagtg aatacagcca   67800
gctcagaggt tttgatgtta ggatctgttt gctccaacag actttgtttt taaaaggctt   67860
ttctcagcca tagctgtctg ttctagcaca aggctggaat gagttccttg tgaaagaggt   67920
gagcaggtgt gagggagggt gtcagtgggc ggtaacccac accttcaagg attaaaggaa   67980
aacttgcatt tggcatgctt gcttcttatt caattttaaa atacatttta acggccgggc   68040
acggtggcta acacctgtaa tcccagcact ttgggggct gaggtgggtg gttcacgagg   68100
ccaggggttc aagaccagcc tggccaagat ggtgaaaccc catctctact aaaaatacaa   68160 aaaaaaaaa aattagccgg gcgtggtggc gggcacctgt aatcccagct actcgggagg   68220
ctgaggcaga gaattgcttg aacccaggag gcggaggttg cattgagccg agatcatgcc   68280
actgcattcc agcctgggcg gcagagcaag actctgtctc aaaataataa taataatttt   68340
ttaaaaatac atttaagtc ctttctcttcc ccacctgcct ccacccacca aatagaagag   68400
gtatttcttc ttctttaatg tcattaaggt tatatggata ccattttcta gagaggaaag   68460
aatgatggaa ttgcctagtg tgagtctagc aattatccta acatacacaa atttctcctt   68520
gttctgtgcc aagatactgt atttaatatt taatgaacat taaatattat ttactagtgt   68580
atttaatggc tgaggcaggg ttaaatatgt attattttca tcccagcaga gttggggag   68640 gtcctagtaa ctatgccatg agctctgtga gggtgaggtg gtgtctttgc cccgcctcc   68700
```

```
ctggcacagt gactggcaca tgattggcat agtgtggaca ttcgtcaagt gaaggaaggc  68760
atcatgagca gatctctggc ctgaatcctt ctgccatcag ctgctcgcca ggtggccctg  68820
gcactgggcc acagggaaac tctccaggct ggtatggttc ctgtctgtgg ctgtcttccc  68880
gggcccatgt taggagactt tcacttccag agccctttcc ctctcagggc cttgcttacc  68940
aagtgactgg ttcccattta ctaggagctc ttaggtcatt gaagatgttg cgtactcccc  69000
ccagtgaggg ctgccttttg atcacagccg ccagaagcct caaggaagga gcagagctgg  69060
aaacagacgc caggccattg cttctgttcc tctggggcag acccagccac ggaagagaca  69120
ttctgggaca agggctgggg tccacctttc aaacgtgtct gcagcaggct ctcagcatgg  69180
actctctgcc tccaaacatc cacctcctca tcggaaaatg gatgggagtg cctgcctgga  69240
gcagctggtg ggagagcgca gcgccagcac gtaggacaca ctcggttcat gggctgatgc  69300
cgttcgcatt gactgcctct tcagctgggt gttgagccac accttggagt caccagtctt  69360
tggagaccaa gtctgctact tttttctcta aagtgacaat cctctgaaac ctccagatca  69420
tcttgaagcc cccgtctgaa agttgcccag agccagtgcc tcacctgctg ttccttgttc  69480 acttttttcac ggggaggcctt gcagggcttt atgacaagat tttatgggtg ctgcccagc  69540 atcattgtga ctcgtgagac agagagaaac cagttgtaac catgtagaca gtggaagtga  69600
tagggagaaa agaggtgagg ggactcttca atccgaaggg aaatgaagtc taagcaggcg  69660
caccctgcag gttcagtgtc aagcccaggg cctggcccca gggtgtggta tttgttgact  69720
gggtgtgtgg accctgggag aaagtctgag aatgaatgtt cctcttagag gtagagagtg  69780
gaaggtgact ctgtgtgtac ttggaattag tgatttctgt acagatgatt cttttagaat  69840
catcatgagt atttttctct ttcagaccca agaaactcga gagatcttac atttccacta  69900
taccacatgg cctgactttg gagtccctga atcaccagcc tcattcttga actttctttt  69960
caaagtccga gagtcagggt cactcagccc ggagcacggg cccgttgtgg tgcactgcag  70020
tgcaggcatc ggcaggtctg gaaccttctg tctggctgat acctgcctct gctggtaag  70080 gaggccctcg cgggtgccct ggggagctcc tctacctgct ctgctgtgat gttttttcct  70140
aagtagaaac tgaagcgctc ctcttccaaa atacagagac tcactgtgtt agtctgtttt  70200
tgcgttacta ataaaggcgt acctgagact cggtaatttg taaagaaaag aggtttaact  70260
ggctcccggt tctgcaggct gtacaagcat ggcaccagca tctgctcggc tcctggggag  70320
gcctcaggga gcttccagtc atggtggaag gtgaagggga gcaggagcaa gagatggggg  70380
aggtcccaga ctcttaacca gctctcttgt gaatgcattg cctcagggag ggcaccaagc  70440 cttttcatgag ggacctgtcc ccctgaccca gacacctccc acccagcccc acctccaaca  70500
ctagggatca catttcagca tgagattggg aggggacaga catctaacgg tgttattaac  70560
gttgcccttg agaattggac ctggctgact tatatctcct ctctggcttt cagatggaca  70620
agaggaaaga cccttcttcc gttgatatca agaaagtgct gttagaaatg aggaagtttc  70680
ggatggggct gatccagaca gccgaccagc tgcgcttctc ctacctggct gtgatcgaag  70740
gtgccaaatt catcatgggg gactcttccg tgcaggtcag cattgccttt gtttgaatcc  70800
aggtgtgacc attttaactt ttttgtcttt gaaggaggct gtcagttgta aaagttcaaa  70860
caccgtctgg tgtcagggga aatagctacc cttcatgttt aaaatagcta gaaagttgtc  70920
aaaatgttca ccatgttgca ctttgtgcct ttgaagtgct cacatagaga gcattgatag  70980
gaagacgaga ctttatttt caaaagatttc atcttccaag tacatggctg cagccctgag  71040
aggccgagag cccctcgcca agccgtcacc tctgctcatg caaagggatt tcctgacaaa  71100
```

```
ccagccgaag tgaacactaa taggacttcc tcttgctgct ctttcaagga tcagtggaag   71160
gagctttccc acgaggacct ggagccccca cccgagcata tcccccccacc tccccggcca   71220 cccaaacgaa tcctggagcc acacaatggg aaatgcaggg agttcttccc aaatcaccag   71280
tgggtgaagg aagagaccca ggaggataaa gactgcccca tcaaggaaga aaaggaagc    71340 cccttaaatg ccgcacccta cggcatcgaa aggtaatatg attgggtccc agcttgttgg   71400
ggtgagggga aatgactttc tgttctagaa acacacgctg gtactgaaac cctgtggatg   71460
cagcctcctg ttggcaagca gcgcttccgc atccttgggg aacagggcgc gtggaccaca   71520
gccactccac tcctggctgc tggaggtccg gtattgggca caggtggcc  gcaggacatg   71580 agccacttct gtgggcttct agtgccacct tgtggtgctt gttggaatga ggggctcgga   71640
gccaccgagt agggttttc  tgcccccccct gacgacagcg ccctccccca ggtttccgga   71700
cagtcctgaa atgtgatgtc caggcttgag tgccctcagt ccccacagtg gtcctttggg   71760
gaatgtaacc tttttatgt  ggtcttgatt aaatcccatt ttacttcctt gcaggttaac   71820
aaccattatt gagtacctat tgatatgtgt ggtgtactga gttaactaga acatgtcccc   71880
tggtctgtgt tctagaccat cttgctggga aaaaggcaga cccaaagcat attttggtgg   71940
gggcccatgg acagtgatgt gatagaggtg tccgctgagg tggtcaggga aggctgcttg   72000
cagtaggtgg ccgtgcacgg aaagtttgca gaatgagcag gtgttagttc cagctggaga   72060
tgactgccgg ctgtgcccctt ggtacctgct ttctggaggg aagttttaag acgtgtgcat   72120
acttgaccca gcagttgtat acatggagaa atttactttg cagcaactct caaaacaagc   72180
gtgtaaagat gtgtataggt agttgtgttt gttgtggcat tgtttgtagt agtgaaaaat   72240
tagagacagg ccaatgatat aaccagggac ctgatcaatt atgttctctc ccggtgttgg   72300
gatattctgt agctcttaaa gaatgagatc tgggtgtact gatgtggcca gacattgcaa   72360
ttgcagtaca tgagaaggca aatcatacag tagtgtgtac accagtgagt cctccagcca   72420
gataaatcct cacagtgacc agtcgcccag gcaccttgtg aaccctaccc tgggtgtggg   72480
tgctatctga agtacctggg ggagggggtg acaagtggac ttcaggctga tgtgggccct   72540
ggcctggccc tccctccaag cagaggggggc tggctcgctg gaaggttaac atcatccaac   72600
tctgtctaca cgtggcttgt tttttcctag aattcctgcc acaatagcag catccttgcc   72660
attcattttc tccaaagtga gtaacccatc tctgccctct gattcctcag catgagtcaa   72720
gacactgaag ttagaagtcg ggtcgtgggg ggaagtcttc gaggtgccca ggctgcctcc   72780
ccagccaaag gggagccgtc actgcccgag aaggacgagg accatgcact gagttactgg   72840
aagcccttcc tggtcaacat gtgcgtggct acggtcctca cggccggcgc ttacctctgc   72900
tacagggtat gtttccactg acagacgcgc tggcgagatg ctcgtgtgca gagagcactg   72960
gccgctagcc cgatggtagg attcagttct gtggtgcatc tgagccagtc tcagaagaaa   73020
cagatcaaag gttttttaaag tctggaactg tggaagggct aacaagagaa ttaaggatcg   73080
atgcactggg gttttaagga gccctctggt cccaagaata taagagtcta atctcagggc   73140
cttaacctat tcaggagtaa gtagagaaaa tgccaaatac gtctgtttct ctctctcttt   73200 tttttttttat tcctttgttt ttggaaaaaa atagagttac aacacattgt tgtttttaac   73260
ctttataaaa agcagctttt tgttatttct ggaacaaaaa aaaacaaagt aggcacttat   73320
gaaactttct catacccctta ggtgatgtaa tcagccatat aatttatatt tgatttccca   73380
gggaaggaat cccaaacttt tacgaatgta aactcccttg gagaagaggg ttaggacgct   73440
gttgcgctca agccccctc  agctgtgtgc acactgagcc aggacagggt ctttgagctt   73500
```

```
tcccactata agaagaacag caacaaaagg ccgtctagaa aaacagaacc tgcctctgct   73560
tctgctcagg gtgtccccgc tgggtttcca ttgtcctttc tccattgctc cctcctgtga   73620
cagccatctt gctcatgtac cagccctcat cacccatcc ccataaatgg gtgtcctcga    73680
ggcctctgcc tgggggtcag aggtcaccac agggtggcca ttggcatgtc aacccgctgt   73740
taattcagag aagtgggctc cacctcattg ggagaagtgc catttcagca gaaattcaca   73800
cgttagacgt gtgttgctgt taagtaaggg gaagagagag gactagcctc agagctctgg   73860
ccatggaaat gacctcctaa gacttttcg tggttttaaa tattttacct ctttccaggt    73920
ggcatctgag tacatcagat ggttttgcaa aatgcaaaca atttttcct tggggatgat    73980 ttttggggag aggggctac tgtaaaaaat aaaaccaaaa ccccctttgc tccctcggag    74040
gttgaagttg ccggggggtg tggccggggt catgcatgag gcgacagctc tgcaggtgcg   74100
ggtctgggct catctgaact gtttggtttc attccagttc ctgttcaaca gcaacacata   74160
gcctgaccct cctccactcc acctccaccc actgtccgcc tctgcccgca gagcccacgc   74220
ccgactagca ggcatgccgc ggtaggtaag ggccgccgga ccgcgtagag agccgggccc   74280
cggacggacg ttggttctgc actaaaaccc atcttccccg gatgtgtgtc tcacccctca   74340
tccttttact ttttgcccct tccactttga gtaccaaatc cacaagccat tttttgagga   74400
gagtgaaaga gagtaccatg ctggcggcgc agagggaagg ggcctacacc cgtcttgggg   74460
ctcgccccac ccagggctcc ctcctggagc atcccaggcg ggcggcacgc caacagcccc   74520
ccccttgaat ctgcagggag caactctcca ctccatattt atttaaacaa ttttttcccc   74580
aaaggcatcc atagtgcact agcatttct tgaaccaata atgtattaaa atttttgat    74640 gtcagccttg catcaagggc tttatcaaaa agtacaataa taaatcctca ggtagtactg   74700
ggaatggaag gctttgccat gggcctgctg cgtcagacca gtactgggaa ggaggacggt   74760
tgtaagcagt tgttatttag tgatattgtg ggtaacgtga gaagatagaa caatgctata   74820
atatataatg aacacgtggg tatttaataa gaaacatgat gtgagattac tttgtcccgc   74880
ttattctcct ccctgttatc tgctagatct agttctcaat cactgctccc ccgtgtgtat   74940
tagaatgcat gtaaggtctt cttgtgtcct gatgaaaaat atgtgcttga aatgagaaac   75000
tttgatctct gcttactaat gtgccccatg tccaagtcca acctgcctgt gcatgacctg   75060
atcattacat ggctgtggtt cctaagcctg ttgctgaagt cattgtcgct cagcaatagg   75120
gtgcagtttt ccaggaatag gcatttgcct aattcctggc atgacactct agtgacttcc   75180
tggtgaggcc cagcctgtcc tggtacagca gggtcttgct gtaactcaga cattccaagg   75240
gtatgggaag ccatattcac acctcacgct ctggacatga tttagggaag cagggacacc   75300
ccccgccccc cacctttggg atcagcctcc gccattccaa gtcaacactc ttcttgagca   75360
gaccgtgatt tggaagagag gcacctgctg gaaaccacac ttcttgaaac agcctgggtg   75420
acggtccttt aggcagcctg ccgccgtctc tgtcccggtt caccttgccg agagaggcgc   75480
gtctgcccca ccctcaaacc ctgtggggcc tgatggtgct cacgactctt cctgcaaagg   75540
gaactgaaga cctccacatt aagtggcttt ttaacatgaa aaacacggca gctgtagctc   75600
ccgagctact ctcttgccag catttttcaca ttttgccttt ctcgtggtag aagccagtac   75660
agagaaattc tgtggtggga acattcgagg tgtcaccctg cagagctatg gtgaggtgtg   75720
gataaggctt aggtgccagg ctgtaagcat tctgagctgg gcttgttgtt tttaagtcct   75780
gtatatgtat gtagtagttt gggtgtgtat atatagtagc atttcaaaat ggacgtactg   75840
gtttaacctc ctatccttgg agagcagctg gctctccacc ttgttacaca ttatgttaga   75900
```

```
gaggtagcga gctgctctgc tatatgcctt aagccaatat ttactcatca ggtcattatt    75960
ttttacaatg ccatggaat aaaccatttt tacaaaaata aaaacaaaaa aagcaaggtg      76020
ttttggtata atacctttc aggtgtgtgt ggatacgtgg ctgcatgacc gggtgggtgg      76080
gggggagtgt ctcagggtct tctgtgacct cacagaactg tcagactgta cagttttcca    76140
acttgccata ttcatgatgg gtttgcattt tagctgcaac aataaaattt ttttctaaag    76200
aacatgaatt tggggtgctt cccattttt tctttgctta atagagctaa accaggatga     76260
gtaactcctg tttctttcta tccctgctga tgtgaaacag atgttgtcaa tcagctgggg    76320
ttagagtttt ccacttctaa gaattaacct cagcatccct gcattgccag caccctcagg    76380
ctggagcgct ttccttgact gtgagcttgt tgaacacctt aggcctcagc ccatttcctt    76440
cccaaattga cgctttgcct gtgtagggcc ctcagataac ttaacaaact taccagtgtt   76500
gtttgaagaa cagtgttttg agttgtaatc tcaaaaccat atcccttacc caattacctg    76560
taagacacaa tggttaccac atctcagtac gtaaagtcca cttgatatag aattgactta    76620 gaataagac agattagtat agttttcat ttgtgtacaa aattaaacaa tgtaaattcc      76680
ccccaaagtg atttttttga cttttgaag taattttgga cttgcaaaat gttgccaaaa     76740
tagtacgaag agttccccag taccctcgaa gtttcctcga ctgtttcaaa gctggctgca    76800
ggcccaggct catgagactg ggaagaggac aggctgtggt catgtggacc cacaggggcc    76860
tggggctgca gaagtcagtg tggcttccac catttcaggt ataaaaaagg gcatctaagc    76920
tttcaagaag agggaggatg ctctagggca gcggtcccca accttttctg gcaccaggaa    76980
ccggttccat ggaagacaat tttttcacag gcctgggggt ggtgagggat ggttttggga    77040
tagaaacttc cacctcagat catcaggcat cagattctca taaggagctt gcaacctgat    77100
ctcttgcaca cattcagttc acaatagggt tcacgctcct aagagaacct gatgctgcag    77160
ctgatctaac aggagatgga gctcaggtgg tcatgctcag tcgctcgcca ctcacctcct    77220
gccatgcagt ccagttccta acaggcctca gaccagtacc ggtctgtggc ctgggggttg    77280
aggacccctg ctctaggctg gtactgctga tgcttaaaaa gagagggttt gccagaaatc    77340
agatgggaca aaagggcaaa ggccgtgcca cagagtgccc atataggggga gagcacgcct   77400 ggagccttcg agagcatgca gagaagcctg gagactgcat ttaccggagc tgctgcctga    77460
ggccaccctc caagtgtccc cacagcgcac cacaagacca caggagtgac ctcctcactg    77520 gcaggtatt ggggaaacaa ctgctgtcta ctcttttggg taaaaagtga acaccaata      77580 gtttaattga aatttcagaa aattgaacat atgaacaagg caaataaata ctaagtaagt   77640 taaaacaca aaatatgtcc aggaagtatc gatgagaatg ttcaagttaa agttctccaa    77700
tgccattgct acagcaacct caaaccctag gttctctctg cactattaac acagacatct   77760
caggacatgg tttgcttttt tttaagactt aaataggaaa ctaattttt tttctttaaa    77820 gcaattgcgt tcttcagtga actctttctt taggccagtt gatggcttct tagcagttta    77880
ttgacgagat cctagggtag cttccgaagc tgggttgatt gattgcattt gggtgcggat    77940
ggccaaagtg agtggcccta ctgcctgtgc tgctcagggc tcctgggctg atgtggtggc    78000
t                                                                    78001
```

<210> SEQ ID NO 3
<211> LENGTH: 4522
<212> TYPE: DNA
<213> ORGANISM: Macaca mulatta

<400> SEQUENCE: 3

```
gcggtgcgta gttccggctg ccggttgaca tgaagaagcc gcggcggcta gggcggcggt      60
agcggcagga gtcggtgctt gctgcggacc tcagggctaa gagcgcgacg cggcctagag     120
cggcggactg cgcagtgggc cgagaaggag gcgcagcagc cgccctggcc cgtcatggag     180
atggaaaagg agttcgagca gatcgacaag tccgggagct gggcggccat ttaccaggat     240
atccgacacg aagccagtga cttcccatgt agagtggcca agcttcctaa gaacaaaaac     300
cgaaataggt acagagacgt cagtcccttt gaccatagtc ggattaaact acatcaagaa     360
gataacgact atatcaacgc tagtttgata aaaatggaag aagcccaaag gagttacatc     420
cttacccagg gccctttgcc taacacatgc ggtcactttt gggagatggt gtgggaacag     480
aaaagcaggg gtgtcgtcat gctcaacaga gtgatggaga aggttcgtt aaaatgcgca     540
cagtactggc cacaaaaaga agaaaaagaa atgatctttg aagacacaaa cttgaaatta     600
acattgatct ctgaagatat caaatcatat tatacagtgc gacagctaga attggaaaac     660
cttacaaccc aagaaactcg agagatctta catttccact ataccacatg gcctgacttt     720
ggagtccccg aatcgccagc ctcattcttg aactttcttt tcaaagtccg agagtcaggg     780
tcactcagcc cggagcatgg gcccgtcgtg gtgcactgca gtgcgggtat cggcaggtct     840
gggaccttct gtctggctga tacctgcctc ttgctgatgg acaagaggaa agaccttct     900
tccgttgata tcaagaaagt gctattagaa atgaggaagt tcggatggg gctgatccag    960
acagcagacc agctgcgctt ctcctacttg gctgtgatcg aaggtgccaa attcatcatg    1020
ggggactcct ctgtgcagga tcagtggaag gagctttccc acgaggacct ggagccccca    1080
cccgagcacg tcccccacc tccccggcca cccaaacgaa tcctggagcc acacaatggg    1140
aaatgcaggg agttcttccc aaatcaccag tgggtgaagg atgagaccca ggaggataaa    1200
gactgcccca tcaaggaaga aacaggaagc cccttaaatg ccgcacccta cagcatggaa    1260
agcatgagtc aagacactga agttagaagt cgggtcgtgg ggggaagtct tcgaggtgcc    1320
caggctgcct ccctagccaa aggggagccg tcaccgccta agaaggagga ggaccatgca    1380
ctgagtcact ggaagccctt cctggtcaac atgtgtgtgg ctacggtcct cacggccggc    1440
gcgtacctct gctacagggt atgtttccac tgacagacgc gctggcgaga tgctcgtgtg    1500
cagagagcac tggccgctag cccgatggta ggattcagtt ctgtggcgca tctgagccag    1560
tctcagaaga aacagatcaa aggttttttaa agtctggaac tgtggaaggg ctaacgagaa    1620
ttaaggatcg atgcactggg gttttaagga gccctctggt cccaagaata taagagtcta    1680
atctcagggc cttaacctat tcaggagtaa gtagagaaaa tgccaaatac gtctgtctct    1740
ctctctctct cttttttta ttcctttgtt tttggaaaaa aatagaatta caacacattg    1800
ttgttttaa cctttataaa aagcagcttt ttgttatttc tggaaaaaaa acaaactagg    1860
cacttaatga aactttctcg tacccttagg tgatgtaatt agctatataa tttatatttg    1920
atttcccagg gaaggaatcc caaactttta cgaatgtaaa ctcccttgga gaagagggtt    1980
aggacgctct tgcgctcaag ccccctcag ctgtgtgcac actgagccag gacagggtct    2040
ttgagctttc ccactgtaag aacagcaaca caaggccgtc tagagaaaca gaacctgcct    2100
ctgcttctgc tcagggtgtc cgttgtcctt tctccattgc tccctcctgt gacagccatc    2160
ttgctcatgt accagccctc atcaccccat tcccataaaa gagtgtcctc gaggcctctc    2220
cctgggggtc agaggtcacc acagggtggc cctcagcatg tcagccctct gttaattcag    2280
aggagtgggc tccacctcat tgggagaagt gccatttcag cagaaatcca cacgttagac    2340
gtgtgttgct gttaagtaag gggaagagag gactagcctc agagctctgg ccatggaaat    2400
```

```
gacctcctga gacttttca tcgttttaaa tattttacct cttttcaggt ggccatctga    2460
gtacatcaga tggttttgca aaatgcaaac aattttttcc ttgggggtga ttttggggga    2520 gaagggcta ctgtaaaaaa taaaaccaaa accccctttg ctccctcgga ggttgaagtt    2580 gccgggggt gtggccgggg tcgtgcatga ggcgacagct ctgcgggtgc gggtctgggc    2640
tcatctgaac tgtttggttt cattccagtt cctgttcaac agcaacacat agcctgaccc    2700
tcctccactc cacctccacc cactgtccgc ctctgcccgc agagcccacg cccgactagc    2760
aggcatgccg cggtaggtaa gggccgccgg accgcgtaga gagccgggcc ccggacggac    2820
gttggttctg cactaaaacc catcttcccc ggatgtgtgt ctcacccctc atcctttac    2880 tttttgcccc ttccactttg agtaccaaat ccacaagcca ttttttgagg agagtgaaag    2940
agtaccatgc tggcggcgca gagggagggg gcctgcacct gtctggaggc tcgccccacc    3000
cagggctccc tcctggagca tcccaggcag gtggtacacc aacagccccc ttgactcgca    3060
gggagcaact ctccactcca tatttattta aacaatttt ccccaaaggt gtccatagtg    3120
cactagcatt tcttgaacc aataatgtat taaaatttt tgatgtcagc cttgcatcaa    3180
gggctttatc aaaaagtaca ataataaatc ctcaggtagt actgggaatg gaagactttg    3240
ccatgggcct gctgcgtcag accagtactg ggaaggagga cggttgtaag gcagtcgtta    3300
tttagtgata ttgtgggtaa cgtgagaaga tagaacaatg ctataatata taatgaacac    3360
gtgggtattt aataagaaac atgatgtgag attactttgt cccgcttatt ctcctccctg    3420
ttatctgcta gatctagttc tcaaatcact gctcccccgt gtgtactaga atgcatgtaa    3480
ggtcttcttg tgtcctgatg aaaaatatgt gcttgaaatg agaaactttg atctctgctt    3540
actaatgtgc cccatgtcca agtccaacct gcctgtgcat gacctgatca ttacatggct    3600
gtggttccta agcctgttgc tgaagtcgtt gtcactcagc aatagggtgc agttttccag    3660
gaataggcat ttgcctcatt cctggcctga cactctagtg acttcctggt gagacccggc    3720
ctgtcctggt gcagcagggt ctcgctgtaa ctcagacatt ccagggtat gggaagccat    3780 attcacacct cacgctctgg acattattta ggcaagcagg acaccccccc gccccccacc    3840
tttgggatca gcctctgcca ttccaagtca gcactcttct tgagcagact gtgatttgga    3900
agagaggcaa ctgctggaaa ccacacttct gaaacagcc tgggtgacgg tcctttaggc    3960
agcctgccgc cgtctccgtc tgggttcacc ttgccgagag aggcgcgtct gccccaccct    4020
cgaaccctgt ggggcctgat ggtgctcacg actcttcctg caagggaac tgaagacctc    4080 cacattaagt ggcttttaa caagaaaaac acggcagctg tagctcccga gctactctct    4140
tgccagcatt ttcacatttt gcctttctcg tggtagaagc cagtacagag aaattctgtc    4200
gtgggaacat tcgaggcatc accccataga gctgtggtga ggtgtggata aggcttaggt    4260
gccaggctgt aagcattctg agctgggctt gttgtttta agtcctgtat atgtatgtag    4320
tagtttgggt gtgtatatat agtagcattt caaaatggac gtactggttt aacctcctat    4380
cctcggagag cagctggctc tccaccttgt tacacgtatg ttagagaggt agcgagctgc    4440
tctgctatat gccttaagcc aatatttact catcaggtca ttattttta caatggccat    4500 ggaataaacc attttacaa aa                                             4522
```

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide -continued

<400> SEQUENCE: 4
ttgtcgatct gctcgaactc                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
gacttgtcga tctgctcgaa                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
cccggacttg tcgatctgct                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gctcccggac ttgtcgatct                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ccagctcccg gacttgtcga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ggcaccttcg atcacagcca                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gctccttcca ctgatcctgc                                              20

<210> SEQ ID NO 11
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 11
ggtcatgcac aggcaggttg                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
aggtcatgca caggcaggtt                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gatcaggtca tgcacaggca                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tgatcaggtc atgcacaggc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
acccttggaa tgtctgagtt                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
cccatacccT tggaatgtct                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tcccataccc ttggaatgtc                                              20
```

-continued

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
ttcccatacc cttggaatgt                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
tattccatgg ccattgtaaa                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
ttattccatg gccattgtaa                                           20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tttattccat ggccattgta                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
gtttattcca tggccattgt                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ggtttattcc atggccattg                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide -continued

<400> SEQUENCE: 24
tggtttattc catggccatt                                           20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
atggtttatt ccatggccat                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
aatggtttat tccatggcca                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
aaatggttta ttccatggcc                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
aaaatggttt attccatggc                                           20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
aaaaatggtt tattccatgg                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
aggaggtcat ttccatggcc                                           20

<210> SEQ ID NO 31
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 31
ggtcatttcc atggccagag                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ggaggtcatt tccatggcca                                              20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
ctggtttaac ctcctatcct tgga                                         24

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
cagagcagct cgctacctct ct                                           22

<210> SEQ ID NO 35
<211> LENGTH: 32
<212> TYPE: DNA
<213> ORGANISM: Artificial Sequence
<220> FEATURE:
<223> OTHER INFORMATION: Probe

<400> SEQUENCE: 35
cagctggctc tccaccttgt tacacattat gt                                32

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ggagttcgag cagatcgaca a                                            21

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ggccactcta catgggaagt c                                            21
```

<210> SEQ ID NO 38
<211> LENGTH: 24
<212> TYPE: DNA
<213> ORGANISM: Artificial Sequence
<220> FEATURE:
<223> OTHER INFORMATION: Probe

<400> SEQUENCE: 38
agctgggcgg ccatttacca ggat                                              24

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39
tattccatgg ccattgta                                                     18

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 40
ttattccatg gccattgt                                                     18

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
tttattccat ggccattg                                                     18

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 42
gtttattcca tggccatt                                                     18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
ggtttattcc atggccat                                                     18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

```
<400> SEQUENCE: 44
tggtttattc catggcca                                              18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 45
atggtttatt ccatggcc                                              18

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46
aatggtttat tccatggc                                              18

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 47
aaatggttta ttccatgg                                              18

<210> SEQ ID NO 48
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 48
atggtttatt ccatgg                                                16

<210> SEQ ID NO 49
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 49
tttattccat ggccat                                                16

<210> SEQ ID NO 50
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 50
gcgtttgctc ttcttcttgc gttttttt                                   27

<210> SEQ ID NO 51
<211> LENGTH: 20
```

```
<212> TYPE: DNA
<213> ORGANISM: Artificial Sequence
<220> FEATURE:
<223> OTHER INFORMATION: Primer

<400> SEQUENCE: 51
gaccagctgc gcttctccta                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic Primer

<400> SEQUENCE: 52
cagaggagtc ccccatgatg                                              20

<210> SEQ ID NO 53
<211> LENGTH: 24
<212> TYPE: DNA
<213> ORGANISM: Artificial Sequence
<220> FEATURE:
<223> OTHER INFORMATION: Probe

<400> SEQUENCE: 53
ttggctgtga tcgaaggtgc caaa                                         24

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
gggccctttg cctaacaca                                               19

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
cgacacccct gcttttctg                                               19

<210> SEQ ID NO 56
<211> LENGTH: 25
<212> TYPE: DNA
<213> ORGANISM: Artificial Sequence
<220> FEATURE:
<223> OTHER INFORMATION: Probe

<400> SEQUENCE: 56
cggtcacttt tgggagatgg tgtgg                                        25
```